US008191187B2

(12) United States Patent
Brykalski et al.

(10) Patent No.: US 8,191,187 B2

(45) Date of Patent: Jun. 5, 2012

(54) ENVIRONMENTALLY-CONDITIONED TOPPER MEMBER FOR BEDS

(75) Inventors: Michael J. Brykalski, Monrovia, CA (US); David Marquette, Farmington Hills, MI (US); John Terech, Milan, MI (US); Robert Vidojevski, Brownstown, MI (US)

(73) Assignee: Amerigon Incorporated, Northville, MI (US)

( * ) Notice: Subject to any disclaimer, the term of this patent is extended or adjusted under 35 U.S.C. 154(b) by 0 days.

(21) Appl. No.: 13/183,313

(22) Filed: Jul. 14, 2011

(65) Prior Publication Data

US 2011/0258778 A1 Oct. 27, 2011

Related U.S. Application Data

(63) Continuation of application No. 12/856,482, filed on Aug. 13, 2010.

(60) Provisional application No. 61/238,655, filed on Aug. 31, 2009.

(51) Int. Cl.

| | |
|---|---|
| *A47C 21/04* | (2006.01) |
| *A61G 7/057* | (2006.01) |
| *A61F 7/00* | (2006.01) |

(52) U.S. Cl. ...... 5/423; 5/691; 5/726; 5/652.1; 607/104; 297/180.13

(58) Field of Classification Search .............. 5/691, 724, 5/726, 652.1, 652.2, 284; 297/180.1, 180.11, 297/180.12, 180.13; 607/104
See application file for complete search history.

(56) References Cited

U.S. PATENT DOCUMENTS

| | | | |
|---|---|---|---|
| 96,989 | A | 11/1869 | Somes |
| 771,461 | A | 10/1904 | Clifford |
| 2,461,432 | A | 2/1949 | Mitchell |

(Continued)

FOREIGN PATENT DOCUMENTS

| | | |
|---|---|---|
| DE | 10238552 | 8/2001 |

(Continued)

OTHER PUBLICATIONS

International Search Report and Written Opinion for Application No. PCT/US2010/047173 (the PCT counterpart of the parent application, U.S. Appl. No. 12/856,482) dated Oct. 7, 2010.

(Continued)

*Primary Examiner* — Michael Trettel

(74) *Attorney, Agent, or Firm* — Knobbe, Martens, Olson & Bear, LLP

(57) ABSTRACT

According to certain arrangements, a conditioner mat for use with a bed assembly includes an upper layer comprising a plurality of openings, a lower layer being substantially fluid impermeable, at least one interior chamber defined by the upper layer and the lower layer and a spacer material positioned within the interior chamber. In one embodiment, the spacer material is configured to maintain a shape of the interior chamber and to help with the passage of fluids within a portion of interior chamber. The conditioner mat additionally includes an inlet in fluid communication with the interior chamber, at least one fluid module comprising a fluid transfer device and a conduit placing an outlet of the at least one fluid module in fluid communication with the inlet. In some arrangements, the fluid module selectively delivers fluids to the interior chamber through the conduit and the inlet. In one embodiment, fluids entering the chamber through the inlet are generally distributed within the chamber by the spacer material before exiting through the plurality of openings along the upper layer. The conditioner mat can be configured to releasably secure to a top of a bed assembly.

20 Claims, 41 Drawing Sheets

U.S. PATENT DOCUMENTS 2,462,984 A 3/1949 Maddison
2,493,067 A 1/1950 Goldsmith
2,512,559 A 6/1950 Williams
2,782,834 A 2/1957 Vigo
2,791,956 A 5/1957 Guest
2,931,286 A 4/1960 Fry, Sr. et al.
2,976,700 A 3/1961 Jackson
3,030,145 A 4/1962 Kottemann
3,039,817 A 6/1962 Taylor
3,136,577 A 6/1964 Richard
3,137,523 A 6/1964 Karner
3,209,380 A 10/1965 Watsky
3,266,064 A 8/1966 Figman
3,529,310 A 9/1970 Olmo
3,550,523 A 12/1970 Segal
3,928,876 A 12/1975 Starr
4,413,857 A 11/1983 Hayashi
4,423,308 A 12/1983 Callaway et al.
4,563,387 A 1/1986 Takagi et al.
4,671,567 A 6/1987 Frobose
4,685,727 A 8/1987 Cremer et al.
4,712,832 A 12/1987 Antolini et al.
4,777,802 A 10/1988 Feher
4,793,651 A 12/1988 Inagaki et al.
4,825,488 A 5/1989 Bedford
4,853,992 A 8/1989 Yu
4,905,475 A 3/1990 Tuomi
4,923,248 A 5/1990 Feher
4,981,324 A 1/1991 Law
4,997,230 A 3/1991 Spitalnick
5,002,336 A 3/1991 Feher
5,016,304 A 5/1991 Ryhiner
5,102,189 A 4/1992 Saito et al.
5,106,161 A 4/1992 Meiller
5,117,638 A 6/1992 Feher
5,125,238 A 6/1992 Ragan et al.
5,265,599 A 11/1993 Stephenson et al.
5,335,381 A 8/1994 Chang
5,367,728 A 11/1994 Chang
5,372,402 A 12/1994 Kuo
5,382,075 A 1/1995 Shih
5,385,382 A 1/1995 Single, II et al.
5,416,935 A 5/1995 Nieh
5,419,489 A 5/1995 Burd
5,433,741 A 7/1995 Truglio
5,448,788 A 9/1995 Wu
5,473,783 A 12/1995 Allen
5,493,742 A 2/1996 Klearman
5,584,084 A 12/1996 Klearman et al.
5,597,200 A 1/1997 Gregory et al.
5,613,729 A 3/1997 Summer, Jr.
5,613,730 A 3/1997 Buie et al.
5,626,021 A 5/1997 Karunasiri et al.
5,626,386 A 5/1997 Lush
5,640,728 A 6/1997 Graebe
5,642,539 A 7/1997 Kuo
5,645,314 A 7/1997 Liou
5,675,852 A 10/1997 Watkins
5,692,952 A 12/1997 Chih-Hung
5,715,695 A 2/1998 Lord
5,871,151 A 2/1999 Fiedrich
5,887,304 A 3/1999 von der Heyde
5,902,014 A 5/1999 Dinkel et al.
5,921,314 A 7/1999 Schuller et al.
5,921,858 A 7/1999 Kawai et al.
5,924,766 A 7/1999 Esaki et al.
5,924,767 A 7/1999 Pietryga
5,927,817 A 7/1999 Ekman et al.
5,934,748 A 8/1999 Faust et al.
5,963,997 A 10/1999 Hagopian
6,003,950 A 12/1999 Larsson
6,006,524 A 12/1999 Park
6,019,420 A 2/2000 Faust et al.
6,052,853 A 4/2000 Schmid
6,059,018 A 5/2000 Yoshinori et al.
6,062,641 A 5/2000 Suzuki et al.
6,073,998 A 6/2000 Siarkowski et al.
6,079,485 A 6/2000 Esaki et al.
6,085,369 A 7/2000 Feher
6,109,688 A 8/2000 Wurz et al.
6,119,463 A 9/2000 Bell
6,145,925 A 11/2000 Eksin et al.
6,148,457 A 11/2000 Sul
6,161,241 A 12/2000 Zysman
6,186,592 B1 2/2001 Orizakis et al.
6,189,966 B1 2/2001 Faust et al.
6,189,967 B1 2/2001 Short
6,196,627 B1 3/2001 Faust et al.
6,206,465 B1 3/2001 Faust et al.
6,223,539 B1 5/2001 Bell
6,263,530 B1 7/2001 Feher
6,291,803 B1 9/2001 Fourrey
6,336,237 B1 1/2002 Schmid
6,341,395 B1 1/2002 Chao
6,425,527 B1 7/2002 Smole
6,487,739 B1 12/2002 Harker
6,493,888 B1 12/2002 Salvatini et al.
6,493,889 B2 12/2002 Kocurek
6,511,125 B1 1/2003 Gendron
6,541,737 B1 4/2003 Eksin et al.
6,546,576 B1 4/2003 Lin
RE38,128 E 6/2003 Gallup et al.
6,581,225 B1 6/2003 Imai
6,596,018 B2 7/2003 Endo et al.
6,598,251 B2 7/2003 Habboub et al.
6,604,785 B2 8/2003 Bargheer et al.
6,606,754 B1 8/2003 Flick
6,606,866 B2 8/2003 Bell
6,619,736 B2 9/2003 Stowe et al.
6,626,488 B2 9/2003 Pfahler
6,629,724 B2 10/2003 Ekern et al.
6,644,735 B2 11/2003 Bargheer et al.
6,676,207 B2 1/2004 Rauh et al.
6,684,437 B2 2/2004 Koenig
6,687,937 B2 2/2004 Harker
6,700,052 B2 3/2004 Bell
6,708,352 B2 3/2004 Salvatini et al.
6,711,767 B2 3/2004 Klamm
6,730,115 B1 5/2004 Heaton
6,761,399 B2 7/2004 Bargheer et al.
6,764,502 B2 7/2004 Bieberich
6,772,825 B2 8/2004 Lachenbruch et al.
6,782,574 B2 * 8/2004 Totton et al. ...................... 5/713
6,786,541 B2 9/2004 Haupt et al.
6,786,545 B2 9/2004 Bargheer et al.
6,808,230 B2 10/2004 Buss et al.
6,828,528 B2 12/2004 Stowe et al.
6,840,576 B2 1/2005 Ekern et al.
6,855,158 B2 2/2005 Stolpmann
6,857,697 B2 2/2005 Brennan et al.
6,857,954 B2 2/2005 Luedtke
6,871,365 B2 3/2005 Flick et al.
6,893,086 B2 5/2005 Bajic et al.
6,904,629 B2 6/2005 Wu
6,907,739 B2 6/2005 Bell
6,967,309 B2 11/2005 Wyatt et al.
6,976,734 B2 12/2005 Stoewe
6,977,360 B2 12/2005 Weiss
6,990,701 B1 1/2006 Litvak
7,036,163 B2 5/2006 Schmid
7,040,710 B2 5/2006 White et al.
7,052,091 B2 5/2006 Bajic et al.
7,063,163 B2 6/2006 Steele et al.
7,070,231 B1 7/2006 Wong
7,070,232 B2 7/2006 Minegishi et al.
7,100,978 B2 9/2006 Ekern et al.
7,108,319 B2 9/2006 Hartwich et al.
7,114,771 B2 10/2006 Lofy et al.
7,134,715 B1 11/2006 Fristedt et al.
7,178,344 B2 2/2007 Bell
7,181,786 B2 2/2007 Schoettle
7,201,441 B2 4/2007 Stoewe et al.
7,272,936 B2 9/2007 Feher
7,296,315 B2 * 11/2007 Totton et al. ...................... 5/737
7,338,117 B2 3/2008 Iqbal et al.
7,356,912 B2 4/2008 Iqbal et al.
7,370,911 B2 5/2008 Bajic et al.

| | | | |
|---|---|---|---|
| 7,425,034 | B2 | 9/2008 | Bajie et al. |
| 7,469,432 | B2 | 12/2008 | Chambers |
| 7,475,464 | B2 | 1/2009 | Lofy et al. |
| 7,478,869 | B2 | 1/2009 | Lazanja et al. |
| 7,480,950 | B2 | 1/2009 | Feher |
| 7,555,792 | B2 | 7/2009 | Heaton |
| 7,587,901 | B2 | 9/2009 | Petrovski |
| 7,591,507 | B2 | 9/2009 | Giffin et al. |
| 7,640,754 | B2 | 1/2010 | Wolas |
| 7,665,803 | B2 | 2/2010 | Wolas |
| 7,708,338 | B2 | 5/2010 | Wolas |
| RE41,765 | E | 9/2010 | Gregory et al. |
| 7,827,805 | B2 | 11/2010 | Comiskey et al. |
| 7,877,827 | B2 | 2/2011 | Marquette et al. |
| 7,892,271 | B2 | 2/2011 | Schock et al. |
| 7,914,611 | B2 * | 3/2011 | Vrzalik et al. .................... 96/11 |
| 2002/0100121 | A1 | 8/2002 | Kocurek |
| 2003/0019044 | A1 | 1/2003 | Larsson et al. |
| 2003/0070235 | A1 | 4/2003 | Suzuki et al. |
| 2003/0084511 | A1 | 5/2003 | Salvatini et al. |
| 2003/0145380 | A1 | 8/2003 | Schmid |
| 2003/0150060 | A1 | 8/2003 | Huang |
| 2003/0160479 | A1 | 8/2003 | Minuth et al. |
| 2003/0188382 | A1 | 10/2003 | Klamm et al. |
| 2003/0234247 | A1 | 12/2003 | Stern |
| 2004/0090093 | A1 | 5/2004 | Kamiya et al. |
| 2004/0177622 | A1 | 9/2004 | Harvie |
| 2005/0011009 | A1 | 1/2005 | Wu |
| 2005/0086739 | A1 | 4/2005 | Wu |
| 2005/0173950 | A1 | 8/2005 | Bajic et al. |
| 2005/0278863 | A1 | 12/2005 | Bahash et al. |
| 2005/0285438 | A1 | 12/2005 | Ishima et al. |
| 2005/0288749 | A1 | 12/2005 | Lachenbruch |
| 2006/0087160 | A1 | 4/2006 | Dong et al. |
| 2006/0130490 | A1 | 6/2006 | Petrovski |
| 2006/0137099 | A1 | 6/2006 | Feher |
| 2006/0158011 | A1 | 7/2006 | Marlovits et al. |
| 2006/0162074 | A1 | 7/2006 | Bader |
| 2006/0197363 | A1 | 9/2006 | Lofy et al. |
| 2006/0214480 | A1 | 9/2006 | Terech |
| 2006/0273646 | A1 | 12/2006 | Comiskey et al. |
| 2007/0035162 | A1 | 2/2007 | Bier et al. |
| 2007/0040421 | A1 | 2/2007 | Zuzga et al. |
| 2007/0069554 | A1 | 3/2007 | Comiskey et al. |
| 2007/0138844 | A1 | 6/2007 | Kim |
| 2007/0158981 | A1 | 7/2007 | Almasi et al. |
| 2007/0200398 | A1 | 8/2007 | Wolas et al. |
| 2007/0204629 | A1 | 9/2007 | Lofy |
| 2007/0251016 | A1 | 11/2007 | Feher |
| 2007/0262621 | A1 | 11/2007 | Dong et al. |
| 2007/0277313 | A1 | 12/2007 | Terech |
| 2007/0296251 | A1 | 12/2007 | Krobok et al. |
| 2008/0000025 | A1 | 1/2008 | Feher |
| 2008/0028536 | A1 | 2/2008 | Hadden-Cook |
| 2008/0047598 | A1 | 2/2008 | Lofy |
| 2008/0087316 | A1 | 4/2008 | Inaba et al. |
| 2008/0100101 | A1 | 5/2008 | Wolas |
| 2008/0143152 | A1 | 6/2008 | Wolas |
| 2008/0148481 | A1 | 6/2008 | Brykalski et al. |
| 2008/0164733 | A1 | 7/2008 | Giffin et al. |
| 2008/0166224 | A1 | 7/2008 | Giffin et al. |
| 2008/0173022 | A1 | 7/2008 | Petrovski |
| 2008/0223841 | A1 | 9/2008 | Lofy |
| 2008/0263776 | A1 | 10/2008 | O'Reagan |
| 2009/0000031 | A1 | 1/2009 | Feher |
| 2009/0025770 | A1 | 1/2009 | Lofy |
| 2009/0026813 | A1 | 1/2009 | Lofy |
| 2009/0033130 | A1 | 2/2009 | Marquette et al. |
| 2009/0064411 | A1 | 3/2009 | Marquette |
| 2009/0106907 | A1 | 4/2009 | Chambers |
| 2009/0126109 | A1 * | 5/2009 | Lee .................................. 5/421 |
| 2009/0193814 | A1 | 8/2009 | Lofy |
| 2009/0218855 | A1 | 9/2009 | Wolas |
| 2010/0001558 | A1 | 1/2010 | Petrovski |
| 2010/0011502 | A1 | 1/2010 | Brykalski et al. |
| 2010/0146700 | A1 | 6/2010 | Wolas |
| 2010/0193498 | A1 | 8/2010 | Walsh |
| 2010/0235991 | A1 * | 9/2010 | Ward et al. ........................ 5/423 |
| 2011/0048033 | A1 | 3/2011 | Comiskey et al. |
| 2011/0107514 | A1 | 5/2011 | Brykalski et al. |
| 2011/0115635 | A1 | 5/2011 | Petrovski et al. |

FOREIGN PATENT DOCUMENTS

| | | |
|---|---|---|
| DE | 10115242 | 10/2002 |
| EP | 0 617 946 | 3/1994 |
| EP | 0 621 026 | 10/1994 |
| EP | 0 862 901 | 9/1998 |
| FR | 1 327 862 | 5/1963 |
| FR | 2 893 826 | 6/2007 |
| GB | 2 251 352 | 12/2000 |
| RU | 2297207 | 4/2007 |
| WO | WO 97/17930 | 5/1997 |
| WO | WO 02/11968 | 2/2002 |
| WO | WO 02/058165 | 7/2002 |
| WO | WO 03/051666 | 6/2003 |
| WO | WO 2005/120295 | 12/2005 |
| WO | WO 2007/060371 | 5/2007 |

OTHER PUBLICATIONS

Feher, Steve, Thermoelectric Air Conditioned Variable Temperature Seat (VTS) & Effect Upon Vehicle Occupant Comfort, Vehicle Energy Efficiency, and Vehicle Environment Compatibility, SAE Technical Paper, Apr. 1993, pp. 341-349.

Feher, Steve, Stirling Air Conditioned Variable Temperature Seat (SVTS) and Comparison with Thermoelectric Air Conditioned Variable Temperature Seat (VTS), SAE Technical Paper Series, International Congress and Exposition, No. 980661, Feb. 23-26, 1998, pp. 1-9.

Lofy, J. et al., Thermoelectrics for Environmental Control in Automobiles, Proceeding of Twenty-First International Conference on Thermoelectrics (ICT 2002), published 2002, pp. 471-476.

Okamoto et. al., The Effects of a Newly Designed Air Mattress upon Sleep and Bed Climate, Applied Human Science, vol. 16 (1997), No. 4 pp. 161-166.

Winder et al., Heat-retaining Mattress for Temperature Control in Surgery, Br Med J, Jan. 17, 1970 1:168.

I-CAR Advantage Online: The Climate Control Seat System, online article dated Aug. 27, 2001.

Product information for a "*Thermo-Electric Cooling 2008 & Heating Seat Cushion*"; retrieved on May 12, 2008 from http://www.coolorheat.com/.

Product information retrieved on Jan. 30, 2007 from http://store.yahoo.co.jp/maruhachi/28tbe20567.html (no English translation available).

Product information for "Kuchofuku's air conditioned bed, clothing line," retrieved on Oct. 11, 2007 from http://www.engadget.com/2007/06/29/kuchofukus-air-conditioned-bed-clothing-line/.

Product information for "SleepDeep™," retrieved on or about Jun. 2008 from http://www.sleepdeep.se.

* cited by examiner

ENVIRONMENTALLY-CONDITIONED TOPPER MEMBER FOR BEDS

CROSS REFERENCE TO RELATED APPLICATIONS

This application is a continuation application of U.S. patent application Ser. No. 12/856,482, filed Aug. 13, 2010, which claims the priority benefit under 35 U.S.C. §119(e) of U.S. Provisional Patent Application No. 61/238,655, filed Aug. 31, 2009, the entire contents of both of which are hereby incorporated by reference herein.

BACKGROUND

1. Field

This application relates to climate control, and more specifically, to climate control of medical beds, hospital beds, other types of beds and similar devices.

2. Description of the Related Art

Pressure ulcers, which are also commonly referred as decubitus ulcers or bed sores, are lesions that form on the body as a result of prolonged contact with a bed or other surface. Bed sores typically result from exposure to one or more factors, such as, for example, unrelieved pressure, friction or other shearing forces, humidity (e.g., moisture caused by perspiration, incontinence, exudate, etc.), elevated temperatures, age and/or the like. Although such ulcers may occur to any part of the body, they normally affect bony and cartilaginous areas (e.g., the sacrum, elbows, knees, ankles, etc.).

One known method of preventing decubitus ulcers for patients who are confined to beds or other seating assemblies for prolonged time periods includes pressure redistribution or pressure reduction. Pressure redistribution generally involves spreading the forces created by an occupant's presence on a bed over a larger area of the occupant-bed interface. Thus, in order to accomplish pressure redistribution, a bed or other support structure can be designed with certain immersion and envelopment characteristics. For example, a desired depth of penetration (e.g., sinking level) can be provided along the upper surface of the bed when an occupant is situated thereon. Relatedly, an upper portion of a bed can be adapted to generally conform to the various irregularities of the occupant's body.

In order to help prevent the occurrence of decubitus ulcers, one or more other factors may also be targeted, either in addition to or in lieu of pressure redistribution. For example, lower shear materials can be used at the occupant-bed interface. Further, temperature and moisture levels along certain areas of an occupant's body can be reduced. In addition, the control of certain factors, such as high pressure, temperature, friction, moisture and/or the like, may improve the general comfort level of an occupant, even where decubitus ulcers are not a concern. Accordingly, a need exists to provide a conditioner mat or topper member for a bed (e.g., hospital or other medical bed) or other seating assembly that provides certain climate-control features to help prevent bed sores and/or help enhance comfort.

SUMMARY

According to some embodiments, a conditioner mat for use with a bed assembly comprises an upper layer having a plurality of openings and a lower layer being substantially fluid impermeable. In some embodiments, the upper layer is attached to the lower layer along a periphery of the conditioner mat. The mat further comprises an interior chamber defined between the upper layer and the lower layer and a spacer material positioned within the interior chamber, wherein the spacer material is configured to maintain a shape of the interior chamber and configured to help with the passage of fluids within at least a portion of the interior chamber. In some embodiments, the conditioner mat further includes one or more inlets in fluid communication with the interior chamber and one or more fluid modules comprising a fluid transfer device. In some embodiments, the mat additionally includes a conduit connecting an outlet of the fluid module with the inlet, and at least one fluid impermeable member positioned within the interior chamber, wherein the fluid impermeable member generally forms a non-fluid zone. In some embodiments, the conditioner mat includes a control module for regulating at least one operational parameter of the at least one fluid module and a user input device configured to receive at least one climate control setting of the bed assembly. Further, the mat includes at least one power supply adapted to selectively provide electrical power to the at least one fluid module. In some embodiments, the fluid module selectively delivers fluids to the interior chamber through the conduit and the inlet. In some embodiments, fluids entering the interior chamber through the inlet are generally distributed by the spacer material before exiting through the plurality of openings along the upper layer. In one embodiment, fluids entering the interior chamber are generally not permitted to flow through the non-fluid zone(s). In some embodiments, a thickness of the conditioner mat along the non-fluid zone is generally equal to a thickness of the conditioner mat along a portion of the conditioner mat that comprises a spacer material, and the conditioner mat is configured to be removably placed on top of a bed assembly to selectively deliver fluids to an occupant positioned thereon.

According to some embodiments, the upper layer and the lower layer comprise a unitary structure. In other embodiments, the upper layer and the lower layer comprise separate members. In one embodiment, the fluid impermeable member comprises foam. In some embodiments, the non-fluid zone generally separates at least two areas of the conditioner mat that comprise spacer material. In several embodiments, the fluid module is configured to thermally condition fluid being transferred from the fluid transfer device to the interior chamber of the conditioner mat. In some embodiments, the fluid module comprises a thermoelectric device configured to selectively heat or cool fluid being transferred to the interior chamber of the conditioner mat. In one embodiment, the mat further includes at least one securement device for securing the conditioner mat to the bed assembly. In some embodiments, the mat additionally comprises one or more moisture sensors configured to detect a presence of liquid on or within the conditioner mat and/or any other type of sensor (e.g., temperature sensor, pressure sensor, etc.). In one embodiment, the mat further includes at least one fluid distribution member positioned on top of the upper layer, wherein such a fluid distribution member is configured to help distribute fluid flow exiting the plurality of openings of the upper layer.

According to certain embodiments, a topper member for use with a bed (e.g., a medical or hospital bed, a conventional bed, a wheelchair, a seat or other seating assembly, etc.) includes an enclosure defining at least one interior chamber and having substantially fluid impermeable upper and lower layers; wherein the upper layer include a plurality of openings through which fluid from the at least one fluidly-distinct interior chamber can exit. The topper member further includes at least one fluid passage formed within the enclosure by selectively attaching the upper layer to the lower layer and at least two fluid zones formed within the enclosure. In some embodiments, at least one of the fluid zones is in fluid communication with the fluid passage. The topper member includes at least one non-fluid zone within the enclosure, wherein the non-fluid zone includes at least one fluid impermeable member and wherein the fluid impermeable member is configured to generally prevent fluid flow through the non-fluid zone. The topper member further includes a spacer material positioned within the enclosure of each of the fluid zones, said spacer material configured to maintain a desired separation between the upper and lower layers and to help distribute fluid within the at least one interior chamber. In one embodiment, the topper member comprises at least one fluid module having a fluid transfer device (e.g., a blower or fan), a thermoelectric device, a convective heater or other thermal conditioning device, a housing, a controller, one or more sensors and/or the like). The topper member further includes a conduit connecting an outlet of at least one fluid module in fluid communication with at least one fluid passage. In some embodiments, the fluid module selectively delivers fluid to at least one of the two fluid zones through the conduit and the passage. In some embodiments, fluids entering the fluid zones are generally distributed within the interior chamber by the spacer material before exiting through the plurality of openings along the upper layer. In some embodiments, the non-fluid zone is positioned generally between the at least two fluid zones. In one embodiment, a thickness of the topper member along the non-fluid zone is generally equal to a thickness of the topper member along portions of the topper member that comprise a spacer material.

According to some embodiments, the at least two fluid zones comprise a first fluid zone and a second fluid zone, wherein the first and second fluid zones are configured to receive fluid from the same fluid module. In one embodiment, the at least two fluid zones comprise a first fluid zone and a second fluid zone, wherein the first fluid zone is configured to selectively receive fluid from a first fluid module and wherein the second fluid zone is configured to selectively receive fluid from a second fluid module. In some embodiments, the upper and lower layers comprise a unitary structure. In other embodiments, the upper and lower layers are separate members that are permanently or removably attached to each other. In one embodiment, the fluid impermeable member comprises foam or another flow blocking device or member. In one embodiment, the fluid module comprises a thermoelectric device configured to selectively heat or cool fluid being delivered to the topper member. In some embodiments, the topper member further includes one or more moisture sensors configured to detect a presence of liquid on or within the topper member. In some embodiments, the topper member comprises one or more other types of sensors (e.g., temperature sensor, pressure sensor, humidity sensor, occupant detection sensor, noise sensor, etc.), either in addition to or in lieu of a moisture sensor. In some embodiments, the topper member further includes at least one fluid distribution member positioned on top of the upper layer, wherein the fluid distribution member is configured to help distribute fluid flow exiting the plurality of openings of the upper layer and/or to improve the comfort level of an occupant situated on top of the topper member. In one embodiment, the first fluid zone is configured to receive fluid having a first temperature, and the second fluid zone is configured to receive fluid having a second temperature, wherein the first temperature is greater than the second temperature.

According to some embodiments, a conditioner mat or topper member for use with a bed assembly (e.g., hospital or medical bed, conventional bed, other type of bed, other seating assembly, etc.) comprises an upper layer having a plurality of openings and a lower layer. In some embodiments, the upper layer and/or the lower layer are substantially or partially fluid impermeable. The mat or topper member additionally includes at least one interior chamber defined between the upper layer and the lower layer and at least one spacer material positioned within the at least one interior chamber. In some embodiments, the spacer material (e.g., spacer fabric, honeycomb or other air permeable structure, at least partially air permeable foam member, etc.) is configured to maintain a shape of the interior chamber(s) and to help with the passage of fluids within at least a portion of the interior chamber(s). The mat or topper member further comprises an inlet in fluid communication with one or more of the interior chambers, and one or more fluid modules. In one embodiment, the fluid module comprises a blower, fan or other fluid transfer device, a thermoelectric device (e.g., a Peltier circuit), a convective heater, other thermal conditioning devices, sensors, controller, a housing and/or the like. In some embodiments, the mat or topper member also includes a conduit that places an outlet of one or more fluid modules in fluid communication with the inlet. In some arrangements, one or more fluid modules selectively deliver fluid to at least one interior chamber through the conduit and the inlet. In some embodiments, fluid entering the interior chamber through the inlet is generally distributed within said at least one interior chamber by the at least one spacer material before exiting through the plurality of openings along the upper layer. In one embodiment, the conditioner mat is configured to releasably (e.g., using straps, hook-and-loop connections, buttons, zippers, other fasteners, etc.) or permanently secure to a top of a bed assembly.

According to some embodiments, the upper and lower layers comprise a plastic (e.g., vinyl), a fabric and/or any other material. In some embodiments, a fluid module comprises at least one thermoelectric device for thermally or environmentally conditioning (e.g., heating, cooling, dehumidifying, etc.) a fluid being delivered to one or more of the interior chambers. In one embodiment, a spacer material comprises spacer fabric. In some embodiments, the upper and lower layers are configured to form at least one fluid boundary, which fluidly separates a first chamber from one or more other chambers (e.g., a second chamber). In some embodiments, the fluid boundary is generally away from a periphery of the conditioner mat (e.g., toward the middle of the mat or topper member, along the sides but not at the edges, etc.). In some embodiments, the first chamber comprises a spacer material and the second chamber comprises a generally fluid impermeable member, wherein the second chamber being configured to not receive fluid from a fluid module. In certain arrangements, the generally fluid impermeable member comprises a foam pad or other member that provides a continuous feel to an occupant situated on the mat or topper member. In one embodiment, the mat or topper member additionally includes a third chamber, wherein such a third chamber includes a spacer material and is configured to receive fluid (e.g., it is a fluid zone). In one embodiment, the second chamber is generally positioned between the first and third chambers, and wherein the generally fluid impermeable member in the second chamber provides thermal insulation and/or general fluid flow blocking between the first and third chambers. In some embodiments, both the first and second chambers comprise a spacer material, and the both the first and second chambers are configured to receive fluid. In one embodiment, a first fluid module is in fluid communication with the first chamber and a second fluid module is in fluid communication with the second chamber.

According to some embodiments, the conditioner mat comprises a skirt portion configured to releasably secure to a mattress or other support structure of a bed like a fitted sheet. In one embodiment, at least one fluid module is at least partially contained within a fluid box, wherein such a fluid box is configured for attachment to a bed assembly (e.g., at, along or near the headboard, footboard, guiderail, etc.). In another embodiment, at least one fluid module is configured to hang along a side and below of the conditioner mat. In other embodiments, one or more fluid conduits of the mat or topper member are insulated to reduce the likelihood of thermal losses. In some embodiments, the spacer material is generally positioned in locations that are likely to be adjacent to targeted high pressure contact areas with an occupant. In some arrangements, the conditioner mat is configured to be positioned on top of a mattress, pad or other support member of a bed assembly, wherein such a mattress, pad or other support member comprises softness and structural characteristics that facilitate pressure redistribution for an occupant positioned thereon. In one embodiment, the mattress, pad or support member comprises foam, gel, fluid-filled chambers and/or any other material, component, device or feature. In some embodiments, the mat or topper member comprises at least one sensor (e.g., humidity, condensation, temperature, pressure, etc.). In some embodiments, such sensors are configured to provide a signal to a controller to regulate the operation of a fluid module and/or any other electronic device or component. In some embodiments, one or more fluid conduits are at least partially incorporated within a guard rail of a bed assembly. In some embodiments, the conditioner mat is configured to be secured on top of a medical bed, a hospital bed, another type of bed, a wheelchair and/or any other type of seating assembly.

According to some embodiments, a topper member for use with a medical bed includes an enclosure defining at least one fluidly-distinct interior chamber and having substantially fluid impermeable upper and lower layers. In one embodiment, the upper layer includes a plurality of openings through which fluid from the fluidly-distinct interior chamber(s) can exit. The topper member additionally includes one or more securement devices (e.g., straps, elastic bands, buttons, zippers, clip or other fasteners, etc.) for at least temporarily securing the topper member to a medical bed. The topper member further comprises one or more spacer materials positioned within the fluidly-distinct interior chamber(s), wherein such spacer materials are configured to maintain a desired separation between the upper and lower layers and to help distribute fluid within the fluidly-distinct chambers. The topper member also includes at least one fluid module comprising a fluid transfer device (e.g., a blower, fan), a thermoelectric device, convective heater or other thermal conditioning device and/or the like. In some embodiments, the topper member comprises one or more conduits that place an outlet of a fluid module in fluid communication with at least one fluidly-distinct interior chamber. In some embodiments, the fluid module selectively delivers fluids to one or more fluidly-distinct interior chambers through one or more conduits. In some embodiments, fluids entering the interior chambers are generally distributed within such chambers by using at least one spacer material (e.g., spacer fabric, lattice member, honeycomb structure, air permeable foam member, other fluid distribution device, etc.) before exiting through the plurality of openings along the upper layer of the topper member.

According to some embodiments, the enclosure defines a first fluidly-distinct chamber and at least a second fluidly-distinct chamber, such that the first fluidly-distinct chamber is configured to receive fluid having a first temperature from a first fluid module and the second fluidly-distinct chamber is configured to receive fluid having a second temperature from a second fluid module. In some embodiments, at least one property or characteristic of the fluid entering the first chamber is different than a corresponding property or characteristic of the fluid entering the second chamber (e.g., temperature, fluid flow rate, humidity, additives, etc.).

According to some embodiments, a method of preventing or reducing the likelihood of bed sores to an occupant of a bed includes providing a climate controlled topper member. In some embodiments, the topper member includes an enclosure defining at least one fluidly-distinct interior chamber and having substantially fluid impermeable upper and lower layers. In one embodiment, the upper layer includes a plurality of openings through which fluid from the fluidly-distinct interior chamber(s) can exit. The topper member further includes one or more securement devices for at least temporarily securing the topper member to a bed (e.g., a hospital or medical bed, a conventional bed, a wheelchair, other seating assembly, etc.). In some embodiments, a spacer material is positioned within a fluidly-distinct interior chamber, wherein the spacer material is configured to maintain a desired separation between the upper and lower layers and to help distribute fluid within one or more of the fluidly-distinct chambers. The topper member further comprises at least one fluid module (e.g., a fluid transfer device, a thermoelectric device, heat transfer members, controller, etc.) and a conduit placing an outlet of the fluid module in fluid communication with one or more fluidly-distinct interior chambers. In some embodiments, the fluid module selectively delivers fluids to one or more interior chambers through the conduit. In some embodiments, fluids entering the fluidly-distinct interior chambers are generally distributed within said chambers by the spacer material before exiting through the plurality of openings along the upper layer of the topper member. The method additionally includes positioning the topper member on a mattress or support pad of a bed and securing the topper member to the mattress or support pad. In some embodiments, the method comprises activating at least one fluid module to selectively transfer fluids to a bed occupant through the interior chambers. In some embodiments, the method further comprises removing the topper member from the mattress or support pad for cleaning or replacing said topper member or for any other purpose. In one embodiment, cleaning the topper member comprises cleaning exterior surfaces of the upper and lower layers (e.g., wiping it down with a cleansing solution or member).

According to certain arrangements, a conditioner mat for use with a bed assembly includes an upper layer comprising a plurality of openings, a lower layer being substantially fluid impermeable, at least one interior chamber defined by the upper layer and the lower layer and a spacer material positioned within the interior chamber. In one embodiment, the spacer material is configured to maintain a shape of the interior chamber and to help with the passage of fluids within a portion of interior chamber. The conditioner mat additionally includes an inlet in fluid communication with the interior chamber, at least one fluid module comprising a fluid transfer device and a conduit placing an outlet of the at least one fluid module in fluid communication with the inlet. In some arrangements, the fluid module selectively delivers fluids to the interior chamber through the conduit and the inlet. In one embodiment, fluids entering the chamber through the inlet are generally distributed within the chamber by the spacer material before exiting through the plurality of openings along the upper layer. The conditioner mat can be configured to releasably secure to a top of a bed assembly.

According to some arrangements, the upper and lower layers comprise a plastic (e.g., vinyl), fabric (e.g., tight-woven fabric, a sheet, etc.) and/or the like. In one embodiment, the fluid module comprises at least one thermoelectric device for thermally conditioning a fluid being delivered to the chamber. In other arrangements, the spacer material comprises spacer fabric, open-cell foam, other porous foam or material and/or the like. In certain embodiments, the upper and lower layers are configured to form at least one fluid boundary that generally separates a first chamber from a second chamber. In some arrangements, the first chamber comprises a spacer material and the second chamber comprises a generally fluid impermeable member (e.g., foam pad), such that the second chamber is configured to not receive fluid from a fluid module. In other arrangements, the mat additionally includes a third chamber, such that the second chamber is generally positioned between the first and third chambers. The generally fluid impermeable member in the second chamber provides thermal insulation between the first and third chambers.

According to certain embodiments, both the first and second chambers comprise a spacer material, wherein both the first and second chambers are configured to receive fluid, and wherein the upper layer in each of the first and second chambers comprises a plurality of openings. In other arrangements, a system includes a first fluid module and at least a second fluid module, such that the first fluid module is in fluid communication with the first chamber and the second fluid module is in fluid communication with the second chamber. In one embodiment, the conditioner mat comprises a skirt portion configured to releasably secure to a mattress or other support structure of a bed like a fitted sheet. In other arrangements, the fluid module is at least partially contained within a fluid box, which is configured for attachment to a bed assembly. In one embodiment, the fluid module is configured to hang along a side of the conditioner mat. In another arrangement, the conduit is insulated to reduce the likelihood of thermal losses.

According to certain arrangements, the spacer material is generally positioned in locations that are likely to be adjacent to targeted high pressure contact areas with an occupant. In one embodiment, the conditioner mat is configured to be positioned on top of a mattress or support pad of a bed assembly. The mattress or support pad includes softness and structural characteristics that facilitate pressure redistribution for an occupant positioned thereon. In other arrangements, the mattress or support pad comprises a foam, a gel or a plurality of fluid-filled chambers. In one embodiment, the conduit is at least partially incorporated within a guard rail of a bed assembly. In another arrangement, the conditioner mat is configured to be secured on top of a medical bed.

According to certain arrangements, a topper member for use with a medical bed includes an enclosure defining at least one fluidly-distinct interior chamber and having substantially fluid impermeable upper and lower layers. The upper layer includes a plurality of openings through which fluid from the one fluidly-distinct interior chamber can exit. The topper member additionally includes at least one securement device for at least temporarily securing the topper member to a medical bed, a spacer material positioned the fluidly-distinct interior chamber, such that the spacer material is configured to maintain a desired separation between the upper and lower layers and to help distribute fluid within the fluidly-distinct chamber, at least one fluid module comprising a fluid transfer device and a conduit placing an outlet of the fluid module in fluid communication with the fluidly-distinct interior chamber. In one arrangement, the fluid module selectively delivers fluids to the fluidly-distinct interior chamber through the conduit. In another arrangement, fluids entering the at least one fluidly-distinct interior chamber are generally distributed within the chamber by the spacer material before exiting through the plurality of openings along the upper layer. In one embodiment, the enclosure defines a first fluidly-distinct chamber and at least a second fluidly-distinct chamber, wherein the first fluidly-distinct chamber is configured to receive fluid having a first temperature from a first fluid module, and wherein the second fluidly-distinct chamber configured to receive fluid having a second temperature from a second fluid module. The first temperature is greater than the second temperature.

According to certain arrangements, a method of preventing bed sores to an occupant of a bed includes providing a topper member. The topper member comprises an enclosure defining at least one fluidly-distinct interior chamber and having substantially fluid impermeable upper and lower layers. The upper layer comprising a plurality of openings through which fluid from the fluidly-distinct interior chamber can exit. The topper member additionally includes at least one securement device for at least temporarily securing the topper member to a bed, a spacer material positioned within the fluidly-distinct interior chamber, wherein the spacer material is configured to maintain a desired separation between the upper and lower layers and to help distribute fluid within the at least one fluidly-distinct chamber, at least one fluid module comprising a fluid transfer device and a conduit placing an outlet of the fluid module in fluid communication with the fluidly-distinct interior chamber. In some arrangements, the fluid module selectively delivers fluids to the fluidly-distinct interior chamber through the conduit. In another embodiment, fluids entering the fluidly-distinct interior chamber are generally distributed within the chamber by the spacer material before exiting through the plurality of openings along the upper layer. The method additionally includes positioning the topper member on a mattress of a bed, securing the topper member to the mattress and activating the fluid module to selectively transfer fluids to a bed occupant through the fluidly-distinct interior chamber.

BRIEF DESCRIPTION OF THE DRAWINGS

These and other features, aspects and advantages of the present inventions are described with reference to drawings of certain preferred embodiments, which are intended to illustrate, but not to limit, the present inventions. It is to be understood that the attached drawings are provided for the purpose of illustrating concepts of the present inventions and may not be to scale.

DETAILED DESCRIPTION OF THE PREFERRED EMBODIMENTS

This application is generally directed to climate control systems for beds or other seating assemblies. More specifically, in certain arrangements, the present application discloses climate controlled fluid conditioner members or topper members that are configured to be selectively positioned on top of hospital beds, medical beds, other types of beds and/or other seating assemblies (e.g., chairs, wheelchairs, other seats, etc.). Thus, the topper members or conditioner mats and the various systems and features associated with them are described herein in the context of a bed assembly (e.g., medical bed) because they have particular utility in this context. However, the devices, systems and methods described herein, can be used in other contexts as well, such as, for example, but without limitation, seat assemblies for automobiles, trains, planes, motorcycles, buses, other types of vehicles, wheelchairs, other types of medical chairs, beds and seating assemblies, sofas, task chairs, office chairs, other types of chairs and/or the like.

Figure 1:
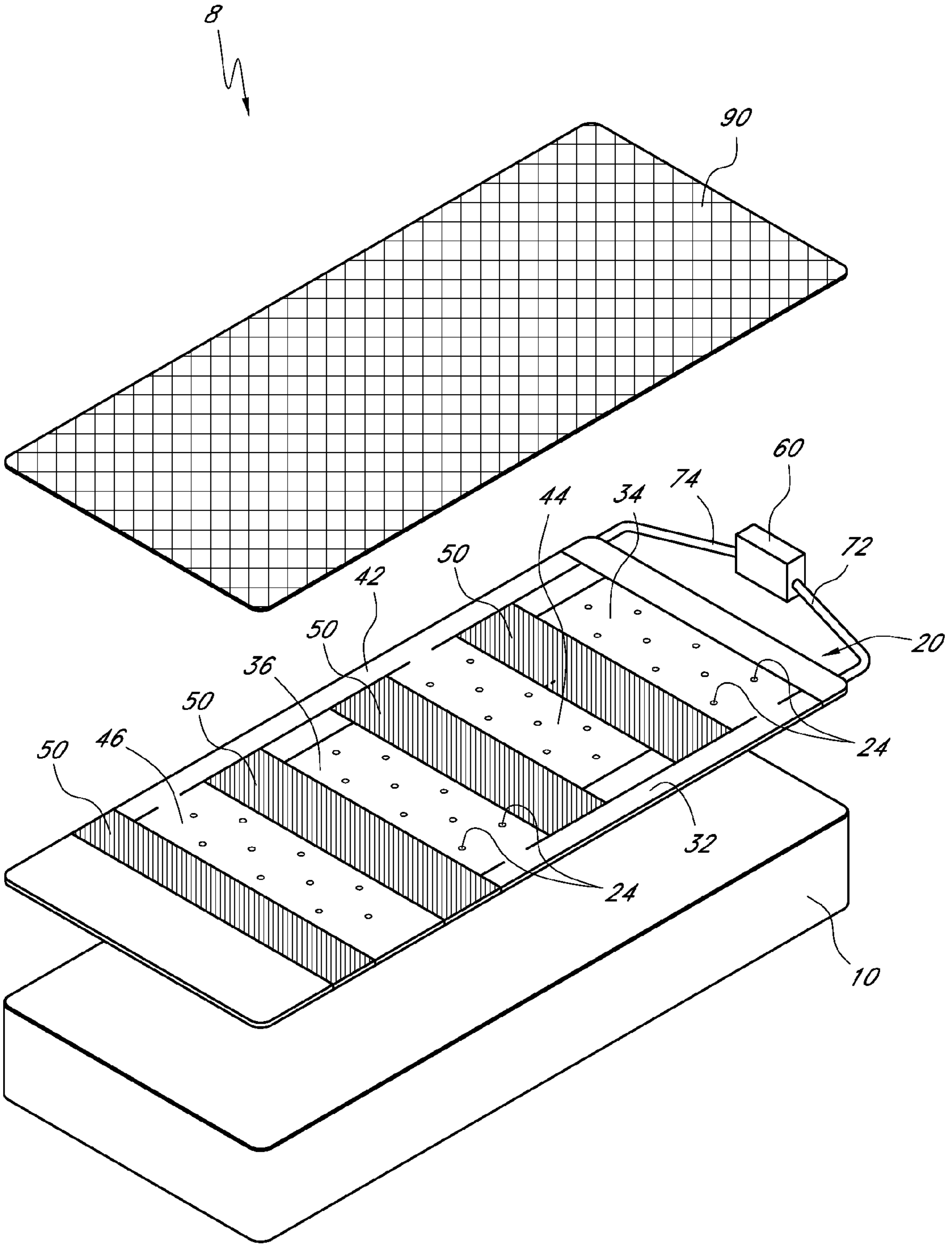
FIG. 1 illustrates an exploded perspective view of one embodiment of a conditioner mat or topper member configured for placement on a bed assembly.

One embodiment of a conditioner mat 20 or topper member adapted to be attached to or otherwise positioned on top of a medical bed 8 is illustrated in FIG. 1. As shown, the mat 20 can be positioned on a mattress, pad, cushion or other support member 10 of a bed 8. According to certain embodiments, the mattress 10 or other support member comprises foam, viscoelastic, air chambers, gel, springs and/or any other resilient materials to give it a desired or required feel. For example, the firmness, pliability and other physical characteristics of the mattress or other support member can be selected so as to enhance pressure redistribution when an occupant is positioned thereon. As discussed in greater detail herein, this can assist in preventing decubitus ulcers for bed occupants.

Figure 6:
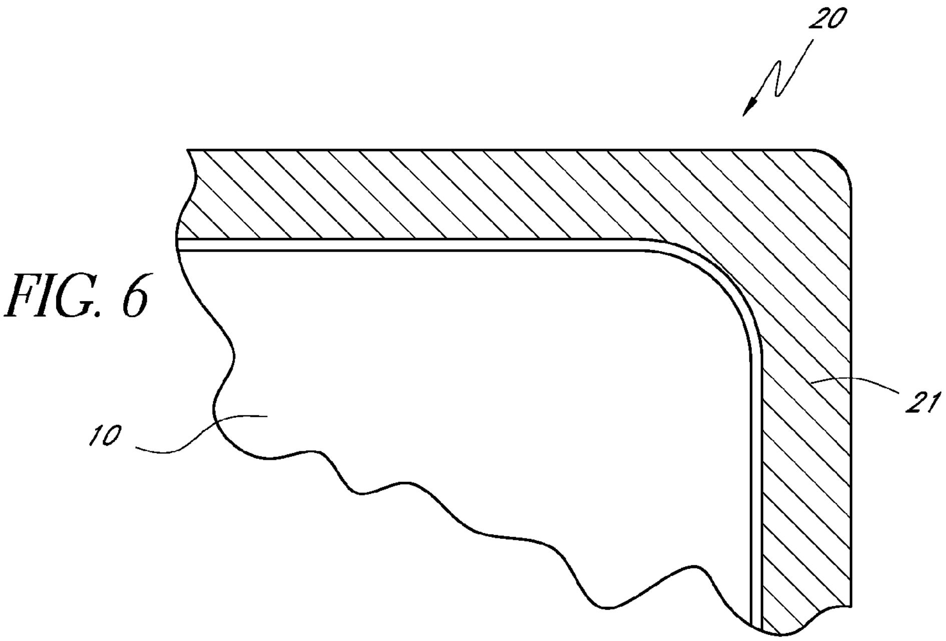
FIG. 6 illustrates a partial bottom view of one embodiment of a conditioner mat or topper member secured to a mattress, pad or other support member of a bed assembly.

As discussed in greater detail herein, the conditioner mat 20 can be releasably secured to a mattress 10 or other portion of a bed using one or more attachment methods or devices. For example, as illustrated in FIG. 6, the mat 20 can comprise a peripheral skirt that is configured to fit around a portion of the mattress (e.g., like a fitted sheet, other encapsulating member, etc.). The skirt can include one or more elasticized portions or members to facilitate its securement to and/or removal from the mattress. Such a design can also provide a more secure connection between the mat 20 and the mattress, pad, cushion or other support member 10. In other arrangements, the position of the separate topper member 20 is maintained relative to the mattress 10 using one or more straps (FIG. 7), zippers, hook-and-loop type fasteners, buttons, snap connections, friction surfaces and/or the like, as desired or required. In one embodiment, the straps 21' are elastic or otherwise expandable. Alternatively, the topper or mat 20 can be permanently attached to a support member 10 (e.g., mattress, pad, cushion, etc.) or other portion of a bed 8.

With continued reference to FIG. 1, one or more portions of the conditioner mat 20 can be selectively supplied with ambient and/or thermally-conditioned (e.g., heated, cooled, etc.) air or other fluid. According to certain arrangements, such fluids are generated by one or more fluid modules located within a separate fluid box 60. A fluid module can include a blower, fan or other fluid transfer device. In certain embodiments, the fluid module can additionally include a thermoelectric device (e.g., Peltier circuit), a convective heater, other types of heating or cooling devices, dehumidifier and/or any other environmentally conditioning device. A fluid module can also include one or more of the following, as desired or required: fluid transfer members (e.g., fins), a sensor (e.g., temperature, humidity, condensation, etc.), a controller and the like.

As illustrated in FIG. 1, fluid exiting a fluid module, which in some embodiments is housed within a fluid box 60 or other enclosure, can be advantageously routed to the mat or topper member 20 using one or more ducts or other fluid conduits 72, 74. The ducts can include one or more flexible, semi-rigid and/or rigid materials, such as, for example, plastic, rubber and the like. In some embodiments, such ducts or conduits are at least partially insulated to prevent or reduce the likelihood of thermal losses between the fluid module and the topper member 20. As discussed in greater detail herein, a fluid module that supplies air or other fluid to a conditioner mat 20 need not be positioned within a separate box 60. For instance, a fluid module can be incorporated within, adjacent to or near a main portion of the topper member. Alternatively, a fluid module can be configured to hang off one or more edges of the topper member and/or the like. Additional disclosure regarding fluid modules is provided in U.S. patent application Ser. No. 11/047,077, filed Jan. 31, 2005 and issued on Sep. 15, 2009 as U.S. Pat. No. 7,587,901, the entirety of which is hereby incorporated herein.

Regardless of the exact configuration of the topper member and fluid modules that are in fluid communication with it, the topper member 20 can include one or more fluid zones 34, 36, 44, 46 into which thermally-conditioned or ambient air can be selectively delivered. For example, the conditioner mat 20 illustrated in FIGS. 1 and 2 comprises a total of four climate control zones 34, 36, 44, 46. The mat 20 can be designed so that two or more zones are in fluid communication with one another. Consequently, air or other fluid having a first type of ventilation or thermal conditioning properties can be provided to certain portions of the mat 20, while air or fluid having a second type of ventilation or thermal conditioning properties can be provided to other portions of the mat, as desired or required. For example, one set of fluid zones 34, 36 can be supplied with relatively cool air, while another set of fluid zones 44, 46 can be supplied with relative warm air, or vice versa.

In other arrangements, a mat or topper member 20 can include additional or fewer fluid zones, as desired or required. For instance, the mat 20 can include only a single conditioning zone (e.g., extending, at least partially, across some or most of the mat's surface area) such as the arrangement illustrated in FIG. 8. In certain embodiments, two or more zones of the topper member or mat 20 are fluidly isolated from each other. Thus, air or other fluid entering one zone (or one set of zones) can be kept substantially separate and distinct from air or fluid entering another zone (or another set of zones). This can help ensure that fluid streams having varying properties and other characteristics (e.g., type or composition of fluid, temperature, relative humidity level, flowrate, etc.) can be delivered to targeted portions of a conditioner mat 20 in a desired manner.

According to certain embodiments, as discussed in greater detail herein, air or other fluid delivered into a zone 34, 36, 44, 46 exits through one or more openings 24 (e.g., holes, apertures, slits, etc.) located along an upper layer or other upper surface of the mat 20. Thus, ambient and/or environmentally-conditioned (e.g., cooled, heated, dehumidified, etc.) air can be advantageously directed to targeted portions of an occupant's body. For example, in the topper member 20 illustrated in FIGS. 1 and 2, the zones 34, 36, 44, 46 are arranged in a manner to generally target an occupant's head (zone 34), shoulders (zone 44), ischial region (zone 36) and heels (zone 46). However, a conditioner mat 20 in accordance with any of the embodiments disclosed herein can be modified to include more or fewer zones to target these and/or other body portions of an occupant.

In certain embodiments, the fluid zones 34, 36, 44, 46 of a conditioner mat or topper member 20 are strategically positioned to target portions of the anatomy that are susceptible to decubitus ulcers, other ailments, general discomfort and/or other problems resulting from prolonged contact with a bed surface. As noted above, reducing the temperature and/or moisture levels in such susceptible anatomical regions can help prevent (or reduce the likelihood of) bed sores and help improve the comfort level of an occupant. For example, with respect to the hospital or medical bed 8 illustrated in FIGS. 1 and 2, the fluid zones 34, 36, 44, 46 can be arranged so that ambient and/or conditioned (e.g., heated, cooled, dehumidified, etc.) air or other fluids are selectively delivered through the topper member 20 toward an occupant's back of the head, shoulders, upper back, elbows, lower back, hips, heels and/or any other target anatomical region.

Figure 2:
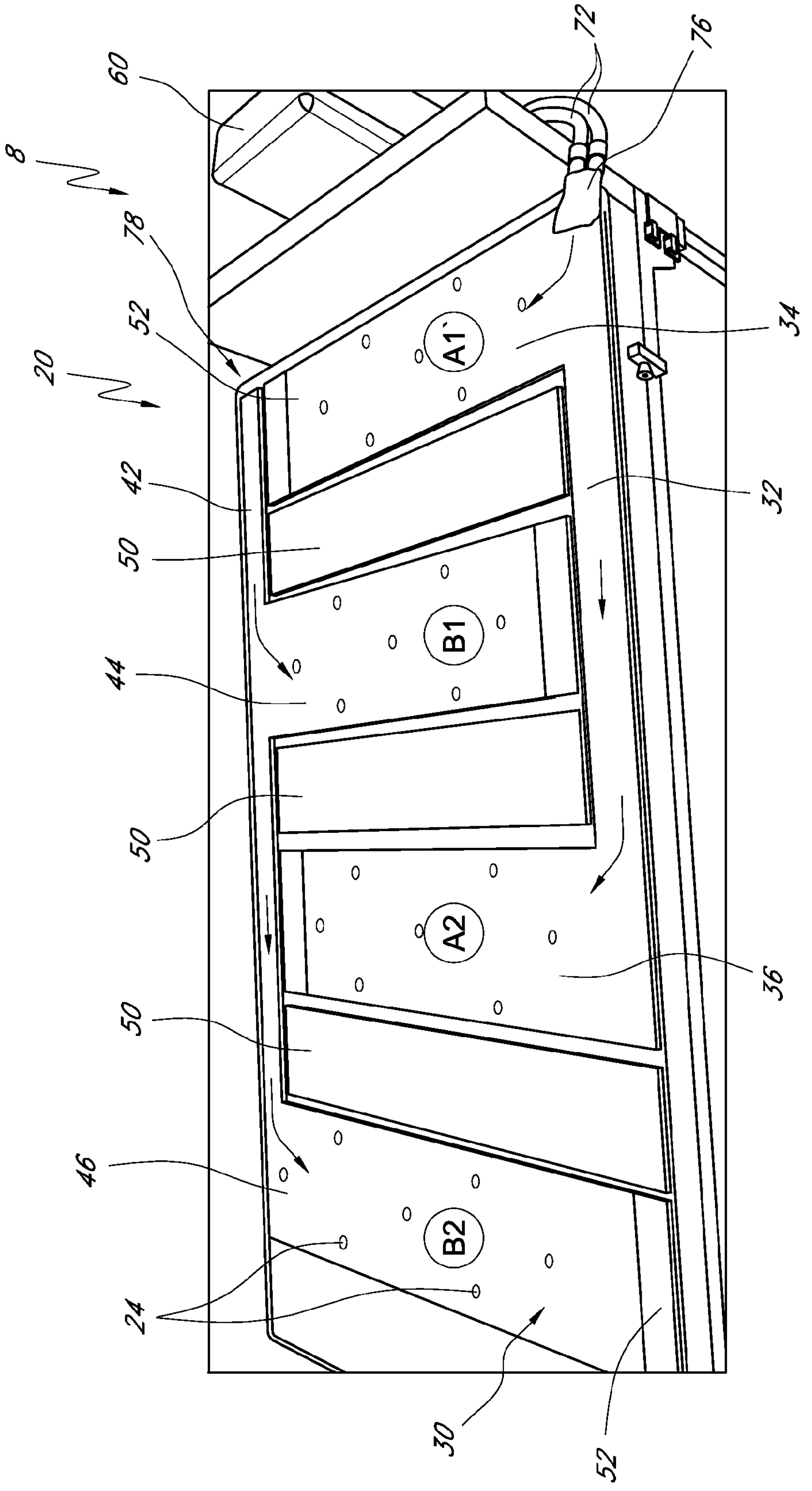
FIG. 2 illustrates a perspective view of a conditioner mat or topper member according to one embodiment.

With continued reference to FIG. 2, air or other fluid can be directed from the fluid module(s) (e.g., stand-alone unit(s), unit(s) located within a fluid box 60, etc.) to the conditioner mat 20 through one or more ducts 72, 74. The ducts 72, 74 can include standard or non-standard conduits. For instance, a duct can include flexible 1-inch diameter rubber tubing having a generally circular cross-section. However, the materials of constructions, cross-sectional size or shape, flexibility or rigidity and other details regarding the ducts 72, 74 or other fluid conduits can vary, as desired or required.

In addition, according to certain arrangements, fluid is supplied to the conditioner mat 20 from both the left and right sides of the bed 8. However, the number, location and other details regarding the fluid inlets into the mat 20 can vary, as desired or required. In FIG. 2, the fluid box 60 is secured to or near the headboard of the bed assembly 8. However, as discussed in greater detail herein, the fluid box 60 can be positioned at any other location relative to the bed, such as, for example, along the footboard, one of the sides and/or the like. Positioning the fluid modules away from the occupant head, regardless of whether or not the fluid modules are included within a fluid box 60, can reduce the noise levels perceived by the occupant. Additional details regarding the fluid modules and the ducts are provided herein.

According to certain arrangements, one or more fittings 76, 78 are situated at the interface of the topper member 20 and a fluid conduit 72, 74. As discussed in greater detail herein, such fittings 76, 78 can advantageously facilitate the connection of the conduits 72, 74 to (and/or disconnection from) the mat or topper member 20. This can be beneficial whenever there is a need or desire to remove the mat 20 from the adjacent mattress, pad, cushion or other support member 10 for cleaning, servicing, replacement and/or any other purpose. The fittings 76, 78 can also help reduce the likelihood that fluids inadvertently leak prior to their delivery into an interior space (e.g., passages 32, 42, zones 34, 36, 44, 46, etc.) of the mat 20.

Figure 3A:
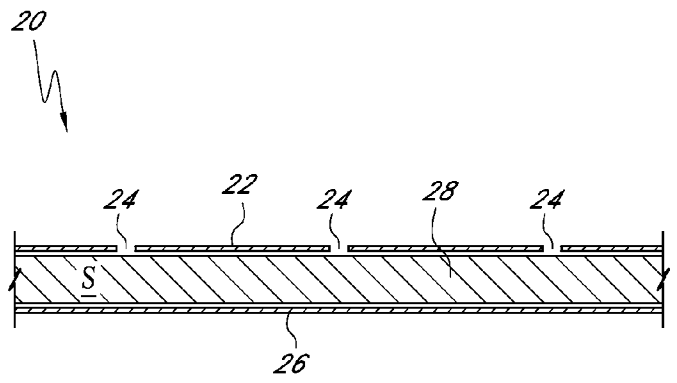
FIG. 3A illustrates a partial cross-sectional view of a conditioner mat or topper member according to one embodiment.

As illustrated in FIG. 3A, the mat 20 can include an upper layer 22 and a lower layer 26 that together generally define a space S therebetween. According to certain arrangements, the upper and lower layers 22, 26 comprise one or more fluid impermeable or substantially fluid impermeable materials and/or conductive materials, such as, for example, vinyl, other plastics, fabric and/or the like. In order to allow air or other fluids to exit the interior space S (e.g., in the direction of a bed occupant), the upper layer 22 can include a plurality of openings 24 (e.g., holes, orifices, etc.) along its upper layer 22. The quantity, shape, size, spacing, orientation, location and other details of the openings 24 can be varied to achieve a desired or required airflow scheme along the top of the mat or topper member 20 during use.

In other arrangements, the upper layer 22 and/or the lower layer 26 of the mat conditioner mat 20 comprise a generally fluid impermeable lining, coating or other member along at least a portion (e.g., some or all) of its surface area in order to provide the mat with the desired air permeability or conductive characteristics or properties. Alternatively, one or more portions of the mat's upper surface (e.g., upper layer 22) can be at least partially fluid permeable. Thus, air or other fluids delivered within an interior space S of a topper member 20 may diffuse through such air permeable portions, toward a bed occupant.

According to certain configurations, as illustrated, for example, in FIG. 3A, one or more fluid distribution members 28 or spacer materials can be positioned within an interior space S of the conditioner mat 20. Such fluid distribution members can provide desired structural characteristics to the mat 20 so that the integrity of the space S is sufficiently maintained during use. In addition, the fluid distribution member 28 or spacer material can help distribute air or other fluids within the interior space S. Consequently, air or other fluids delivered to the conditioner mat or topper member 20 can be advantageously distributed within the interior spaces S of the various zones. This can help ensure that ambient and/or conditioned (e.g., cooled, heated, dehumidified, etc.) fluids are properly delivered through the openings 24 along the top surface of the mat 20.

With continued reference to FIG. 3A, the conditioner mat 20 can be shaped, sized and generally configured to receive a fluid distribution member 28 within the interior space (e.g., generally between the upper and lower layers 22, 26). As noted above, the fluid distribution member 28 can include one or more spacer materials that are adapted to generally maintain their shape when subjected to compressive forces and other loads (e.g., from an occupant seated thereon or thereagainst). For example, in some embodiments, the fluid distribution member 28 comprises a spacer fabric, open cell or other porous foam, a mesh, honeycomb or other porous structure, other materials that are generally air permeable and/or conductive or that have an open structure through which fluids may pass and/or the like. Such spacer fabrics or other spacer materials can be configured to maintain a minimum clearance between the upper and lower layers 22, 26 so that air or other fluid entering the mat 20 can be at least partially distributed within the interior space S before exiting the openings 24. As discussed in greater detail herein, in certain arrangements, the mat or topper member 20 is configured to be selectively removed from the interior space S for replacement, cleaning, repair or for any other purpose.

In some embodiments, the mat or topper member comprises a spacer fabric that is configured to generally retain its three-dimensional shape when subjected to compressive and/or other types of forces. The spacer fabric can advantageously include internal pores or passages that permit air or other fluid to pass therethrough. For example, the spacer fabric can comprise an internal lattice or other structure which has internal openings at least partially extending from the top surface to the bottom surface of the spacer fabric. In some embodiments, the thickness of the spacer fabric or other fluid distribution member is approximately 6-14 mm (e.g., about 6 mm, 8 mm, 10 mm, 12 mm, 14 mm, values between such ranges, etc.). In other arrangements, the thickness of the spacer fabric or other fluid distribution member of the mat is less than approximately 6 mm (e.g., about 5 mm, 4 mm, 3 mm, 2 mm, 1 mm, less than 1 mm, values between such ranges, etc.) or greater than approximately 14 mm (e.g., about 15 mm, 16 mm, 18 mm, 20 mm, 24 mm, 28 mm, 36 mm, greater than 36 mm, values between such ranges, etc.). The spacer fabric or other fluid distribution member can be manufactured from one or more durable materials, such as, for example, foam, plastic, other polymeric materials, composites, ceramic, rubber and/or the like. The rigidity, elasticity, strength and/or other properties of the spacer fabric can be selectively modified to achieve a target spacing within an interior of the mat or topper member, a desired balance between comfort and durability and/or the like. In some embodiments, the spacer fabric can comprise woven textile, nylon mesh material, reticulated foam, open-cell foam and/or the like. The spacer fabric can be advantageously breathable, resistant to crush and air permeable. However, in other embodiments, a spacer fabric can be customized to suit a particular application. Therefore, the breathability, air permeability and/or crush resistance of a spacer fabric can vary.

Figure 3B:
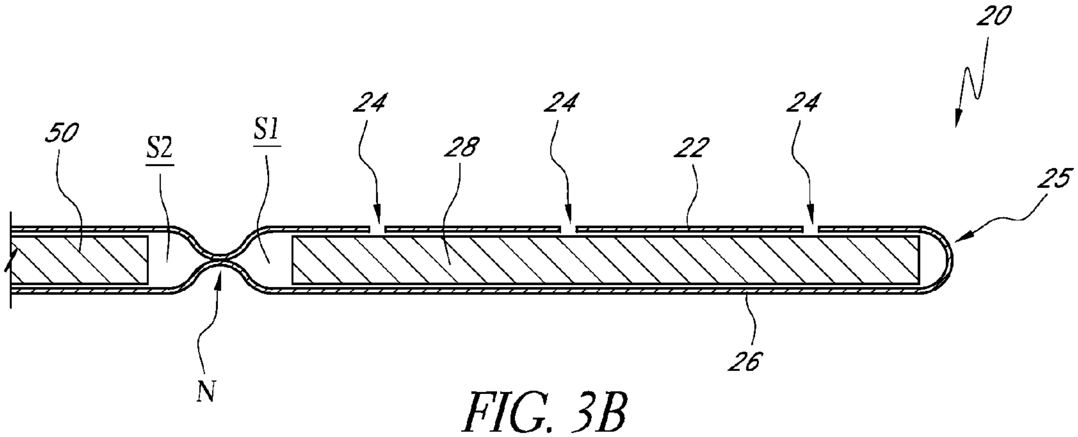
FIG. 3B illustrates another partial cross-sectional view of a conditioner mat or topper member according to one embodiment.

FIG. 3B illustrates a partial cross-sectional view of one embodiment of a conditioner mat 20 which includes a boundary or node N across or through which air or other fluid is generally not permitted to pass. In the illustrated arrangement, the mat comprises fluid impermeable or substantially fluid impermeable upper and lower layers 22, 26 (e.g., vinyl or other thermoplastic sheet, tight-woven fabric, etc.) that define a first interior space S1. As shown in FIG. 3B and noted above with reference to FIG. 3A, the mat or topper member 20 can be sized, shaped and generally configured to removably or permanently receive a fluid distribution member 28 within such a first interior space S1.

Figure 3C:
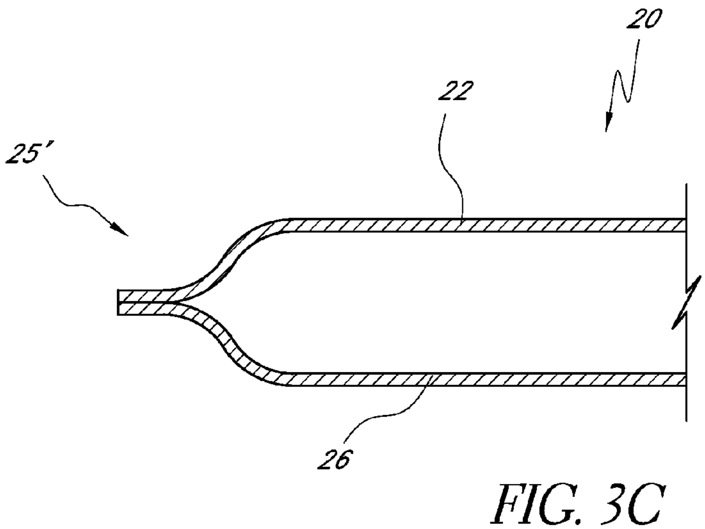
FIG. 3C illustrates yet another partial cross-sectional view of a conditioner mat or topper member according to one embodiment.

In certain configurations, the upper and lower layers 22, 26 are formed from a unitary sheet or member of plastic, fabric and/or other material that has been wrapped around an edge 25 to form a bag-like structure. Alternatively, as illustrated in FIG. 3C, an edge 25' of the mat 20 can be formed by attaching the free ends of the layers 22, 26 to each other, using one or more connection methods or devices, such as, for example, hot melting, stitching, glues or other adhesives, crimping, clips or other fasteners and/or the like.

With continued reference to FIG. 3B, the conditioner mat 20 can include one or more intermediate fluid boundaries or nodes N that act to block or substantially block air flow. Such nodes N can help maintain air or other fluids within certain desired portions or zones of the mat 20. For example, in the arrangement of FIG. 3B, the fluid boundary or node N helps to generally prevent air from passing from the first interior space S1 to the second interior space S2 located immediately adjacent to it. Alternatively, in other arrangements, the second interior space S2 also comprises a fluid distribution member (not shown in FIG. 3B) that is, at least partially, thermally and/or fluidly isolated from the fluid distribution member 28. Under certain circumstances, the mat or topper member 20 comprises one or more interior spaces that are configured to not receive fluids, and thus, to not distribute fluids through the upper layer 22 defining their upper surface. For example, such non-fluid zones can be located along bodily portions of the occupant that are less susceptible to ulcer-formation, other ailments, discomfort and/or other undesirable conditions resulting from prolonged contact with a bed surface.

Relatedly, a mat 20 can include one or more non-fluid zones 50, 52 (FIGS. 1 and 2) where air flow to an occupant is undesirable, unnecessary or otherwise unwanted. In other arrangements, non-fluid zones 50, 52 can provide one or more other functions or benefits. For example, a non-fluid zone can help reduce manufacturing costs, as the cost of relatively expensive spacer fabric and/or other spacer materials is reduced. Further, the use of non-fluid zones 50, 52 can provide an additional level of thermal isolation and/or fluid isolation, with respect to adjacent fluid zones 34, 36, 44, 46. As discussed in greater detail herein, a pad, cushion, gel or similar member comprising foam (e.g., closed-cell, open-cell, viscoelastic, etc.), rubber, fabric, natural or synthetic filler material and/or any other material or substance can be positioned within the second interior space S2. The pad or other member positioned within a non-fluid zone can be air-permeable or non-air permeable, as desired or required. In addition, in some embodiments, the pad or other member or material that is positioned within a non-fluid zone 50, 52 is selected so that the overall firmness, flexibility and/or other characteristics of the non-fluid zones 50, 52 match or substantially match the corresponding properties of one or more adjacent fluid zones.

For any of the embodiments of a conditioner mat or topper member disclosed herein, the mat can have a generally flexible configuration in order to help it conform to the shape of the mattress, pad, cushion or other support member of the bed on which it may be placed. Moreover, a mat or topper member can be designed with certain immersion and envelopment characteristics in mind to assist with pressure redistribution. Such characteristics can further enhance a topper member's ability to help prevent or reduce the likelihood of pressure ulcers, other ailments, general discomfort and/or other undesirable conditions to an occupant positioned thereon.

To further improve the immersion and envelopment characteristics of any of the embodiments of a conditioner mat or topper member disclosed herein, or equivalents thereof, one or more additional layers, cushions or other comfort members can be selectively positioned beneath the mat (e.g., between the mat and the mattress or other support structure of a bed). Such additional layers and/or other members can further enhance the ability of the mat and adjacent surfaces to generally conform to an occupant's anatomy and body contours and shape.

As illustrated in FIGS. 1 and 2, the conditioner mat 20 can include one or more main passages 32, 42 that receive ambient or thermally conditioned air from the fluid modules (e.g., the inlet fittings 76, 78) and distribute it to one or more fluid zones 34, 36, 44, 46. In the depicted embodiment, the mat 20 includes two main passages 32, 42 that extend longitudinally along opposite sides of the mat 20 (e.g., at or near what would be the edge of the bed's mattress or other upper support structure). As discussed in greater detail herein, the passages 32, 42 can be configured to direct air or other fluid to different zones 34, 36, 44, 46 of the mat or topper member 20. A mat 20 can include more or fewer passages 32, 42, as desired or required for a particular design or application. The size, shape, location, spacing, orientation, general configuration and/or other details regarding the passages 32, 42 can also be modified.

The passages 32, 42 can comprise upper and lower layers of plastic, fabric or other material, as discussed herein with reference to FIGS. 3A-3C. In some embodiments, the upper and lower layers that define the passages 32, 42 are the same layers that also define the interior spaces of the fluid zones and/or the non-fluid zones. In such designs, the conditioner mat can include one or more fluid boundaries (e.g., nodes) which help to direct air or other fluids toward specific portions of the mat interior. Such a fluid boundary can include a continuous or substantially continuous line that strategically extends along one or more portions of the mat or topper member (e.g., to define passages 32, 42, fluid zones 34, 36, 44, 46, non-fluid zones 50, 52 and/or the like). As discussed herein with reference to FIGS. 3B and 3C, such fluid boundaries can be established by joining the upper and lower layers 22, 26 of the mat 20 to each other, using, for example, hot melting, stitching, adhesives and/or the like. In other embodiments, as depicted in FIG. 3B, a fluid boundary is created by wrapping a layer around an edge (e.g., bag-like design). As with the fluid zones, one or more spacer materials (e.g., spacer fabric, open cell foam, other porous foam, honeycomb or other porous structure, etc.) can be positioned within the passages 32, 42 to help ensure that the integrity of the passages (e.g., the passage height) is maintained during use. Fluid flow within the passages 32, 42 can be controlled by creating one or more boundary lines (e.g., nodes that extend across a portion of the mat).

With continued reference to the conditioner mat 20 of FIGS. 1 and 2, a first passage 32 is configured to receive fluid (e.g., ambient or conditioned air) from one or more conduits 72 and deliver it to two zones 34, 36, each of which is located along a different region of the mat 20. Likewise, a second passage 42 is configured to receive fluid from one or more conduits and deliver it to two other zones 44, 46. Thus, the conditioning (e.g., cooling, heating, ventilation, etc.) for each set of zones 34, 36 or 44, 46 can be advantageously controlled separately. For example, in one embodiment, relatively cool air is directed to zones 34, 36 (e.g., intended to target a bed occupant's head, shoulders, hips, ischial region, lower back, etc.), while relatively warm air is directed to zones 44, 46 (e.g., intended to target a bed occupant's main torso and feet), or vice versa. In other arrangements, both sets of zones 34, 36 and 44, 46 are subjected to the same or similar type of ventilation or conditioning (e.g., heating, cooling, dehumidification, etc.). Further, the rate of fluid flow into each fluid zone (or set of fluid zones) can be separately adjusted in order to achieve a desired or required effect along the top surface of the mat or topper member 20. For instance, the rate of fluid flow into (and thus, out of the corresponding openings 24) of the first set of zones 34, 36 can be greater or less than the fluid flow into the second set of zones 44, 46. Alternatively, each passage 72, 74 can be configured to selectively delivery air or other fluid to fewer (e.g., one) or more (e.g., three, four, more than four) zones, as desired or required.

As discussed in greater detail herein, a conditioner mat or topper member 20 can include one or more generally air-impermeable portions or non-fluid zones 50, 52 which can assist in establishing physical and/or thermal boundaries. Further, such non-fluid zones 50, 52 can be used to help to create a substantially even and continuous thickness and/or indentation force along the mat 20, especially in regions that do not include a spacer material (e.g., the areas located between adjacent climate controlled zones). Thus, such non-fluid zones can help maintain a generally continuous thickness and feel to the mat or topper member. This can help improve an occupant's comfort level. In addition, the incorporation of non-fluid zones into a mat or topper member design can help reduce manufacturing costs, as the spacer materials that are typically positioned within the fluid zones materials tend to be relatively expensive.

Figure 4:
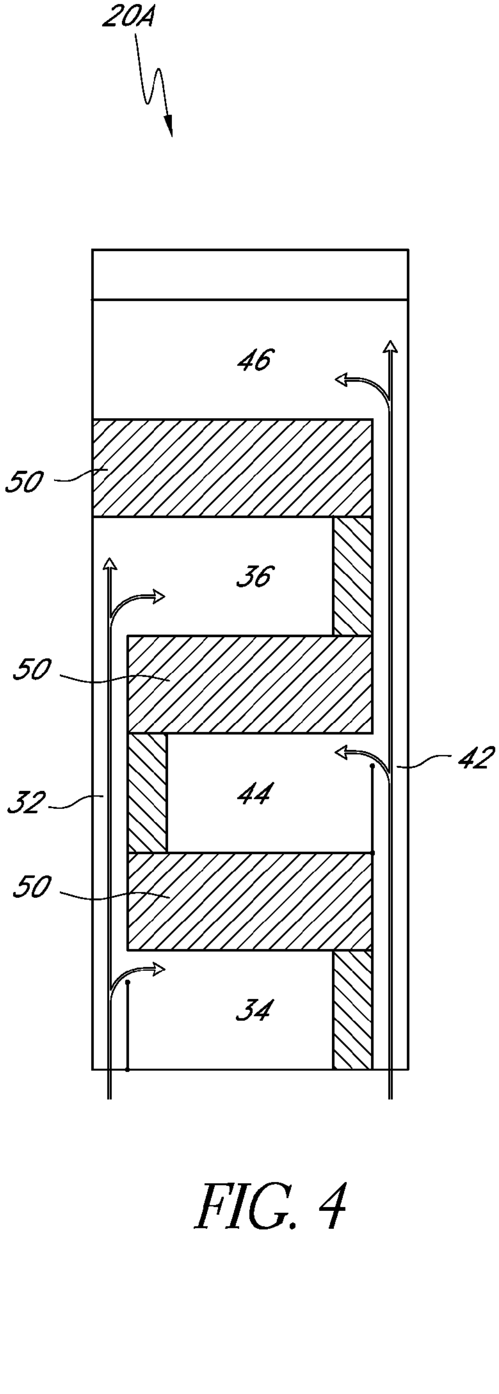
FIGS. 4 and 5 schematically illustrate plan views of a conditioner mat or topper member according to one embodiment.

A plan view of one embodiment of a conditioner mat or topper member 20A is schematically illustrated in FIG. 4. As in the arrangement of FIGS. 1 and 2, the depicted mat 20A comprises two passages 32, 42 which are generally located along opposite edges of the mat 20A and which extend, at least partially, in the longitudinal direction of the mat. In other embodiments, however, a mat or topper member can include fewer or more passages, which may be positioned along or near different portions of the mat (e.g., near the edges, away from edges, near the middle, etc.). Arrows included in FIG. 4 illustrate the general direction of fluid flow through the passages 32, 42 and into (and/or out of) the respective fluid zones 34, 36, 44, 46. For example, ambient and/or conditioned (e.g., cooled, heated, dehumidified, etc.) air or other fluid entering a first passage 32 is generally directed to zones 34 and 36, whereas air or other fluid entering a second passage 42 is generally directed to zones 44 and 46. As noted above, such a configuration can allow air to be distributed to and within certain target regions or areas of the conditioner mat 20A, and thus, the bed (e.g., hospital bed, medical bed, other bed or seating assembly, etc.) on which the mat is positioned. The ability to deliver ambient and/or conditioned (e.g., cooled, heated, etc.) air can help provide one or more benefits to a bed's occupant. For example, as discussed in greater detail herein, such a scheme can help reduce the likelihood of bed sores resulting from heat, friction, moisture, prolonged contact and/or other factors. In addition, such embodiments can improve the general comfort level of the occupant, especially in difficult environmental conditions (e.g., extreme heat or cold, excessively high relative humidity levels, etc.).

With continued reference to FIG. 4, the mat is designed such that adjacent fluid zones (e.g., zones 34 and 44, zones 44 and 36, zones 36 and 46, etc.) are not in fluid communication with the same main passage 32, 42. In addition, as shown in FIG. 4, adjacent zones are generally separated by one or more air-impermeable or substantially air-impermeable zones 50. In certain embodiments, interior spaces of one or more non-fluid zones 50 comprise foam (e.g., closed-cell, open-cell, viscoelastic, etc.), one or more natural or synthetic filler materials or some other generally air-impermeable pad or material.

Figure 5:
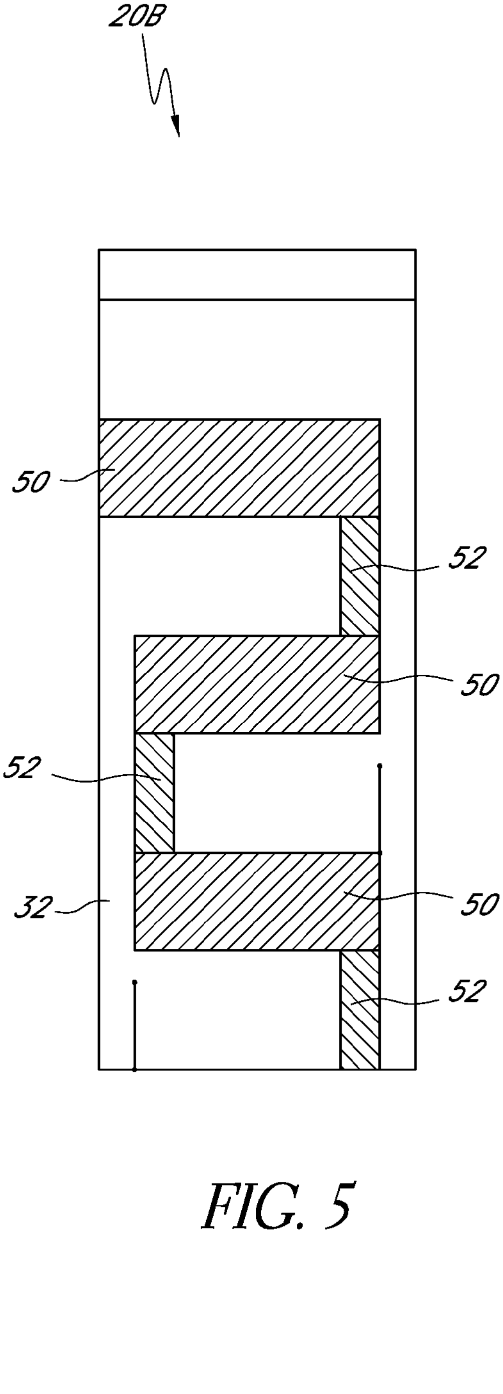

FIG. 5 schematically illustrates another embodiment of a conditioner mat 20B that comprises two main passages 32, 42. A conditioner mat can include additional non-fluid zones 52, which in the illustrated arrangement, are oriented along one edge of a zone and perpendicularly extend between the main non-fluid zones 50. As discussed herein, the various generally air-impermeable zones (e.g., non-fluid zones) 50, 52 included within a conditioner mat can help create thermal and/or fluid barriers between adjacent climate controlled zones 34, 36, 44, 46 (e.g., fluid zones). Accordingly, the function of the conditioner mat can be improved, as the specific zones can operate closer to a target cooling, heating, ventilation or other environmentally-controlled effect.

According to certain arrangements, a conditioner mat, such as any of those disclosed herein, can be approximately 3 feet wide by 7 feet long. However, depending on the size, shape and general design of the bed (e.g., hospital bed, other medical bed, etc.) or other seating assembly on which a mat is configured to be positioned, the dimensions (e.g., length, width, etc.) of the mat can be larger or smaller than noted above. For example, a mat or topper member can be about 3 feet wide by 6 foot-4 inches or 6 foot-8 inches long. In some embodiments, the mat or topper member is sized to fit a standard sized bed (e.g., single, twin, queen, king, etc.) or a custom-designed (e.g., non-standard sized) bed. Thus, conditioner mats or topper members can be specially designed (e.g., non-standard shapes, sizes, etc.) according to a specific bed with which they will be used. Possible shapes include, but are not limited to, other triangular, square, other polygonal, circular, oval, irregular, etc. In addition, the mat can encompass all or substantially all of the top surface area of the mattress or other support member of a bed. Alternatively, the mat or topper member can encompass only a fraction of a mattress's total top surface area, such as, for example, 95%, 90%, 80%, 70%, 60%, 50%, 40%, 30%, 20%, more than 95%, less than 20%, ranges between these values, and/or the like.

In some arrangements, the length and width of the fluid zones 34, 36, 44, 46 of a conditioner mat 20 are approximately 12 inches and 31 inches, respectively. Further, in certain embodiments, the length of the main non-fluid zones 50 is approximately 8 inches. However, the dimensions of the fluid zones and/or the non-fluid zones can vary, as desired or required by a particular application or use. For example, in one arrangement, the length of one or more fluid zones is approximately 8 inches or 16 inches, while the length of the non-fluid zones 50 is approximately 4 inches. In other embodiments, the length, width, shape, location along the mat, orientation, spacing and/or other details of the various portions and components of a conditioner mat may be greater or less than indicated herein. For instance, in some embodiments, the length of a fluid zone or a non-fluid zone is between about 1 inch and 24 inches (e.g., approximately 2, 4, 6, 8, 10, 12, 14, 16, 18, 20, 22, 24, ranges between such values, etc.) less than about 1 inch, more than about 24 inches, etc.

FIG. 6 illustrates a bottom view of a conditioner mat 20 positioned on a mattress 10, cushion or other support member (e.g., foam pad). As shown, the mat 20 can include a lower skirt portion 21 or other securement device that is configured to at least partially wrap around the mattress 10 in order to secure the mat 20 to a bed (e.g., hospital or medical bed) or other seating assembly. Thus, the conditioner mat or topper member 20 can be generally designed like a fitted sheet, allowing it to be conveniently attached to and/or removed from a mattress or other upper support member of a bed assembly. In certain arrangements, the bottom skirt portion 21 extends continuously around the entire mattress 10 or other support member. Alternatively, the skirt portion 21 can be intermittently or at only partially positioned around the periphery of the mat 20, as desired or required. The skirt portion 21 can include one or more elasticized portions or regions to help accommodate for variations in the dimensions of mattresses or other support members and/or to provide for a more snug fit.

Figure 7:
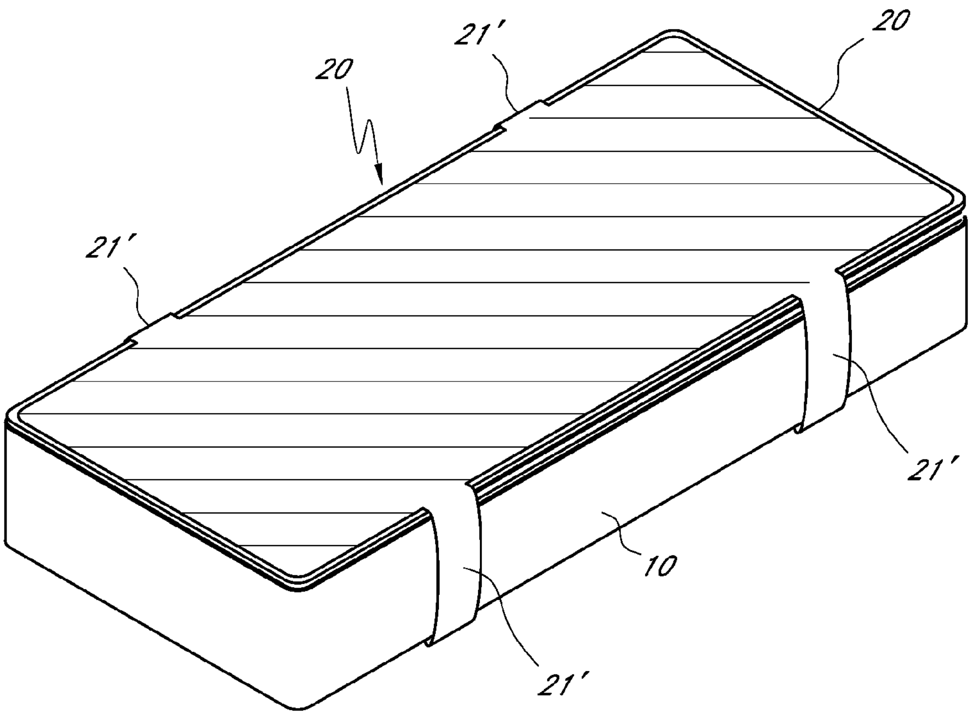
FIG. 7 illustrates a perspective view of a conditioner mat or topper member secured to a bed mattress or other support structure according to another embodiment.

As illustrated in FIG. 7, a conditioner mat 20 can include one or more straps 21', bands, belts or other securement devices to help secure the mat 20 to a mattress, pad or other support structure 10 of a bed. For example, in the depicted embodiment, the mat 20 comprises a total of two securement devices 21' that are shaped, sized and otherwise adapted to partially or completely surround the mattress 10. The securement devices 21' can include flexible straps that comprise an elastic structure and/or one or more elastic, stretchable or other flexible materials or members. Consequently, in such configurations, a user can conveniently pass the straps 21' underneath a mattress 10 or other support structure of a bed in order to properly position the conditioner mat 20 on a bed assembly. Alternatively, each strap, band or other securement device 21' can include two or more loose ends that are configured to be selectively attached to each other using a connection device or method (e.g., belt-like connection, mating clip portions, hook-and-loop fasteners, zippers, buttons, other mechanical fastener systems, a simple tie or knot system and/or the like). Further, regardless of their exact configuration, one or more properties of the securement devices 21' can be modifiable to accommodate mattresses and other bed support structures of various sizes, shaped and types. For instance, in some embodiments, the length of a strap is adjustable.

Any of the embodiments of a conditioner mat or topper member 20 disclosed herein, or equivalents thereof, can be configured to include a fitted sheet design (e.g., FIG. 6), a strap or other securement device (e.g., FIG. 7) and/or any other device or method for temporary or permanent attachment to one or more portions of a bed (e.g., upper mattress or other support structure or member). Alternatively, a mat can be positioned adjacent to a mattress or other portion of a bed without being attached to it. In certain arrangements, a bottom surface of a conditioner mat or topper member includes one or more tactile or non-slip features or properties that are configured to increase the friction between the mat and the adjacent support structure, and thus, reduce the likelihood of movement of the mat relative to the bed, especially when an occupant is positioned thereon. For example, the mat can include a generally unsmooth surface (e.g., a surface having bumps, other projections or other tactile features, recesses or cavities, etc.), one or more relatively high friction regions (e.g., areas having rubber or relatively high-friction layers or strips) and/or the like. In other embodiments, the conditioner mat or other topper member are incorporated into a unitary structure with the bed's mattress or other support structure.

Figure 8:
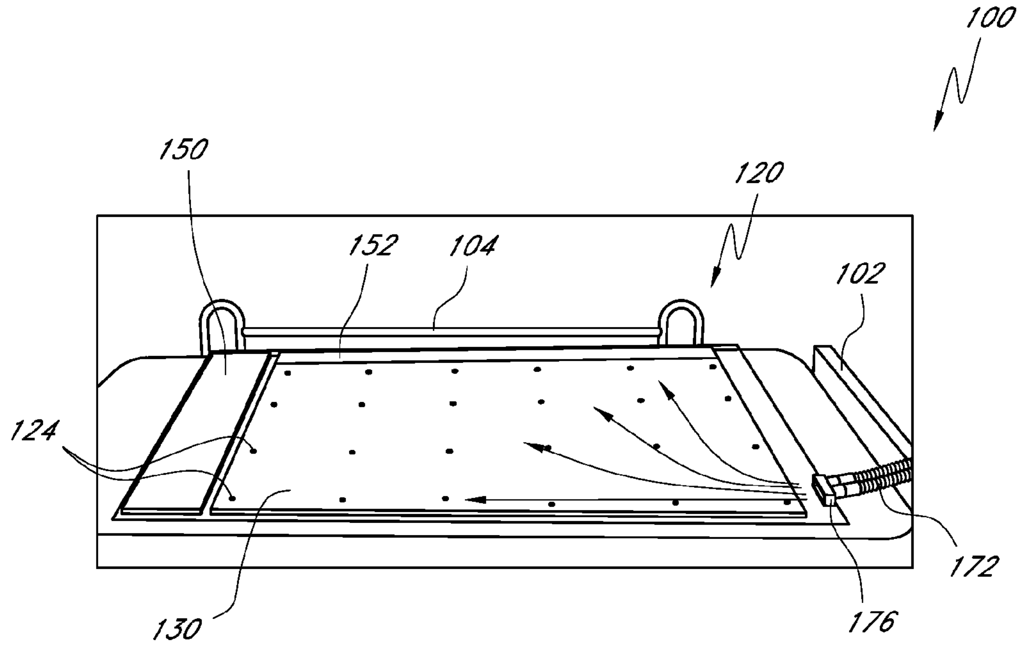
FIG. 8 illustrates a perspective view of a conditioner mat or topper member according to one embodiment.

According to certain embodiments, for example, such as disclosed in FIG. 8, a conditioner mat 120 or topper member includes only a single zone 130 through which ambient and/or conditioned (e.g., cooled, heated, dehumidified, etc.) air or other fluid is selectively delivered. As discussed with reference to other arrangements herein, such a fluid zone 130 can extend along one or more regions or areas of the mat 120 in order to target specific portions of an occupant's body (e.g., head, shoulders, hips, heels, etc.).

Within the fluid zone 130 of the mat illustrated in FIG. 8, an upper surface (e.g., upper fabric, layer, film, other member, etc.) of the mat 120 can include a plurality of openings 124. As discussed herein with reference to other configurations (e.g., those illustrated in FIGS. 1, 2, 3A-3C, etc.), such openings 124 can be configured to allow air or other fluid that enters into an interior space of the mat's fluid zone (e.g., through a spacer fabric, fluid distribution member, etc.). In certain embodiments, the quantity, size, shape, location, density, spacing, orientation and/or other characteristics of the openings 124 are selected to direct the fluid exiting the conditioner mat 120 in targeted regions or areas of the occupant's body, such as, for example, high pressure, temperature, friction and/or moisture regions that are susceptible to decubitus ulcers, other ailments, general discomfort and/or the like.

As shown in FIG. 8, the mat or topper member 120 can include one or more non-fluid zones or areas 150, 152 that are configured to prevent or substantially prevent air and other fluids from entering therein. According to some arrangements, such non-fluid zones 150, 152 comprise a foam (e.g., closed-cell, open-cell, viscoelastic, etc.) pad, other polymeric or other type of pad, filler materials, other layers or members and/or the like. As discussed herein with reference to other embodiments, such as, for example, those illustrated in FIGS. 3A-3C, the upper and lower layers (e.g., vinyl, other plastic, fabric, etc.) of a mat or topper member can be advantageously attached adjacent to such non-fluid zones or portions 50, 52, thereby forming fluid boundaries that block or substantially block fluid flow. In the embodiment illustrated in FIG. 8, the conditioner mat 120 includes non-fluid zones or portions 150, 152 along the bottom and one of the sides of the bed 100. However, such zones 150, 152 or portions that are generally configured to not receive fluids can be positioned at, along or near additional and/or different areas of the mat 120. Further, the respective surface areas of the mat 120 covered by fluid zones 130 and non-fluid zones 150, 152 can be varied to accomplish a desired ventilation and/or conditioning (e.g., cooling, heating, dehumidification, etc.) effect above the mat 120.

Figure 9:
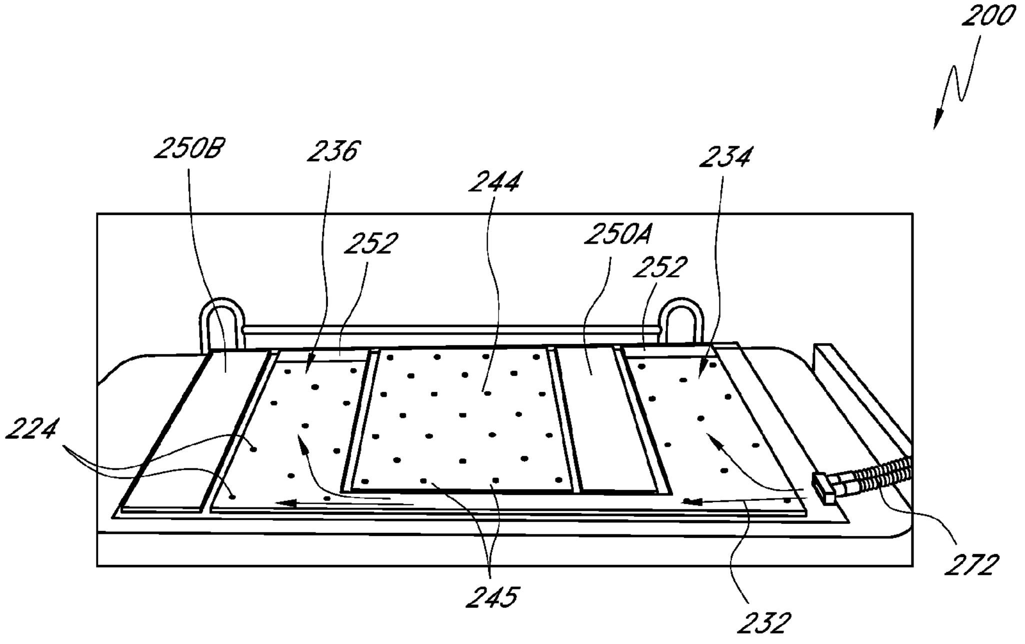
FIG. 9 illustrates a perspective view of a conditioner mat or topper member according to another embodiment.

FIG. 9 illustrates another embodiment of a conditioner mat or topper member 220 secured to a medical bed 200 or other bed assembly. As shown, the mat 220 includes two fluid zones 234, 236 that are in fluid communication with a main passage 232 which extends along one of the mat's sides. In some arrangements, ambient and/or conditioned air is delivered from one or more fluid modules (not shown in FIG. 9) into the main passage 232 via one or more ducts 272 or fluid conduits. The conditioner mat 220 can include one or more additional fluid zones 244 that are generally not in fluid communication with the first set of fluid zones 234, 236. Accordingly, as discussed herein with reference to the arrangements of FIGS. 1 and 2, separate fluid zones (or sets of fluid zones) that are fluidly, hydraulically and/or thermally isolated from each other can be used to vary the ventilation and/or thermal conditioning effects along the top of a mat. Thus, fluid zones 234, 236 of the conditioner mat or topper member 220 can be cooled, while fluid zone 244 is heated, or vice versa. Alternatively, the type of fluid (e.g., ambient air, heated or cooled air, etc.) being delivered to all the fluid zones 234, 236, 244 of a mat 220 can be similar or substantially similar. In other embodiments, although the distinct fluid zones 234, 236, 244 are configured to receive the same or similar types of fluids, the flowrate of fluid delivery can be varied between fluid zones, as desired or required.

Figure 10A:
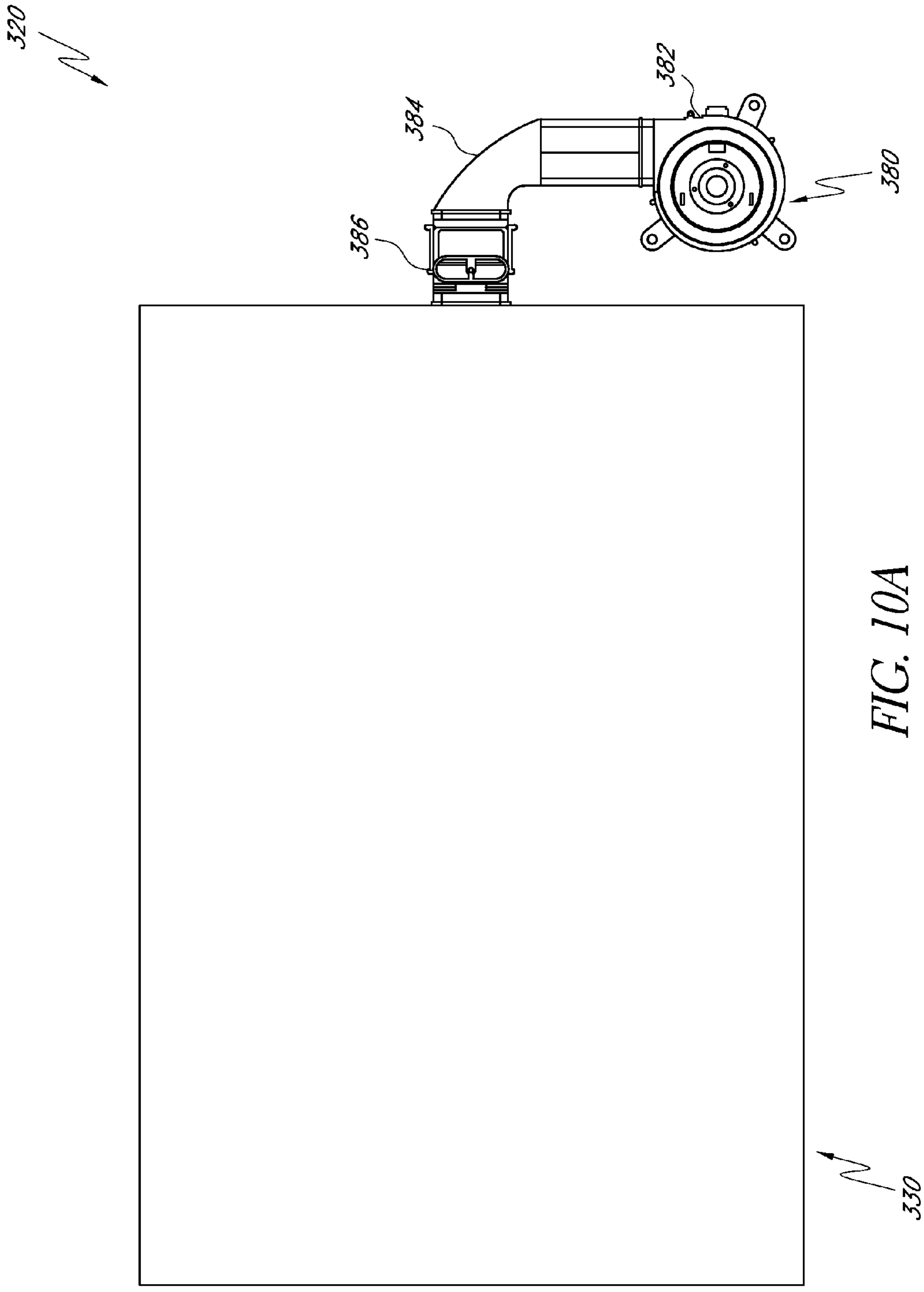
FIG. 10A illustrates a perspective view of a conditioner mat or topper member according to one embodiment.
Figure 10B:
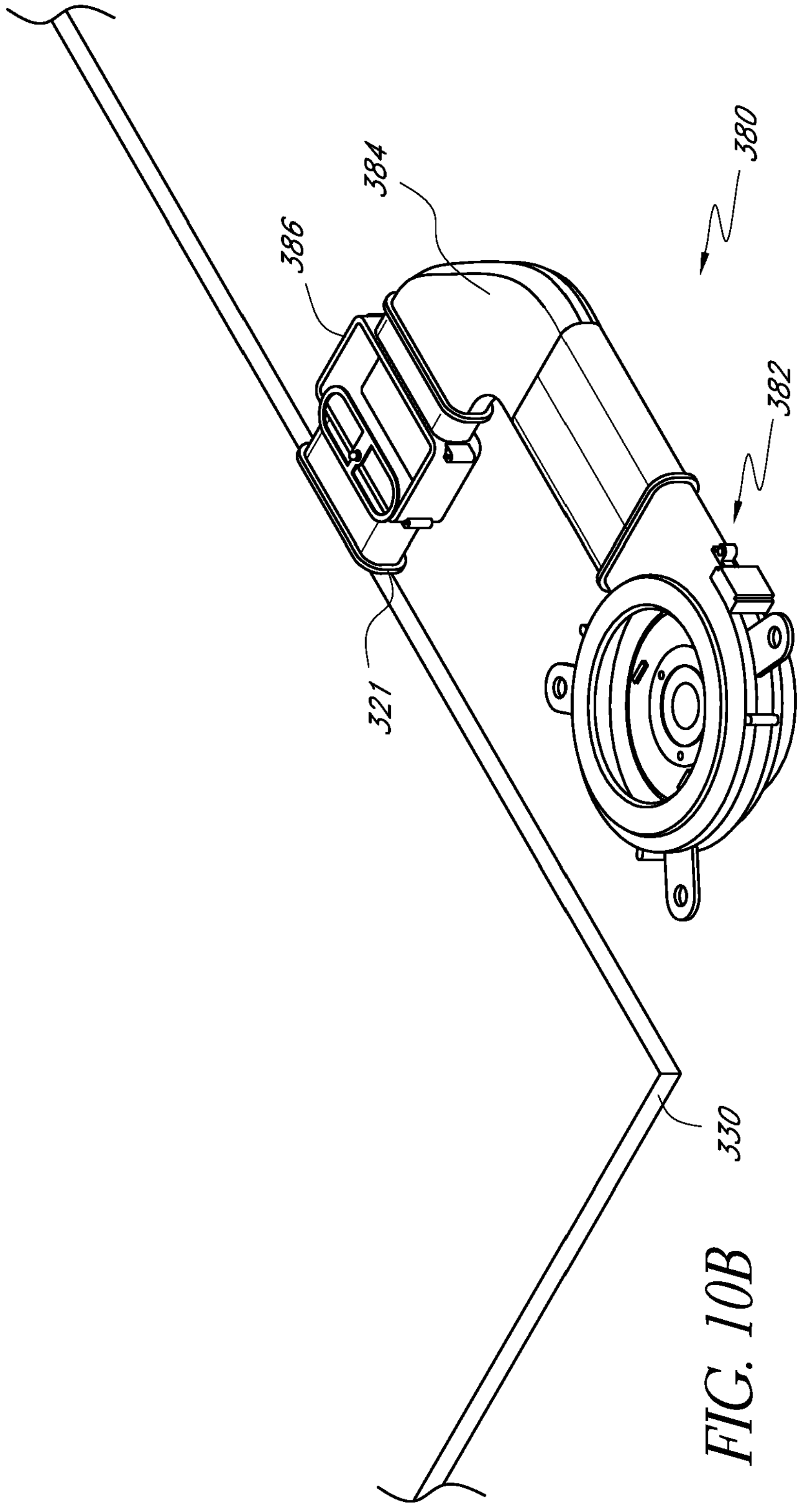
FIG. 10B illustrates a partial perspective view of the conditioner mat or topper member of FIG. 10A.

Another embodiment of a conditioner mat or topper member 320 is illustrated in FIGS. 10A and 10B. As shown, the main portion 330 of the mat or topper member 320 can have a generally rectangular shape. In some arrangements, the dimensions, shape and other properties of the mat 320 are selected to generally match corresponding characteristics of the bed on which the mat will be positioned. As discussed herein with reference to other embodiments, the mat 320 of FIG. 10A can include one or more fluid zones (e.g., regions having an interior space that is configured to receive air or other fluids) and/or non-fluid zones (e.g., regions having an interior space that is not configured to receive fluids) to achieve a desired fluid discharge pattern, and thus a desired climate control scheme, along a top portion of the mat 320.

With continued reference to FIGS. 10A and 10B, the mat or topper member 320 can include a fluid module 380 that is in fluid communication with one or more fluid zones of the mat's main portion 330. As shown, the fluid module 380 can include a blower, fan or other fluid transfer device 382 that selectively delivers/draws air or other fluids to/from the main portion 330 of the mat 320. The fluid module 380, which in the illustrated arrangement is configured to hang off one side of the mat's main portion 330, can also include an inlet fitting 386 that is fluidly coupled to an inlet 321 of the main portion 330. Alternatively, as illustrated in other arrangements herein, a fluid module can be designed to hang from an end of the bed (e.g., a top or bottom end), along another side and/or any other location on, within or near the bed assembly. The fluid transfer device 382 can be placed in fluid communication with the downstream inlet fitting 386 using one or more conduits 384 or other passages.

According to certain embodiments, the fluid module 380 is configured to selectively heat and/or cool the fluid being transferred by the blower 382 toward the main portion 330 of the topper member 320. For example, the fluid transfer device 382 can be placed in fluid communication with one or more thermoelectric devices (e.g., Peltier circuits), convective heaters and/or other conditioning (e.g., heating, cooling, dehumidifying, etc.) devices to selectively heat, cool and/or otherwise condition a fluid passing from the fluid module 380 to the main portion 330 of the mat 320. For example, a thermoelectric device, which may be positioned within an inlet fitting 386, can selectively heat or cool air or other fluid being transferred by the fluid module 380 to the main portion 330 of the mat or topper member 320. As discussed in greater detail herein, fluid modules comprising blowers or other fluid transfer devices, thermoelectric devices or other conditioning devices and/or the like can be incorporated into any of the embodiments of a conditioner mat or topper member disclosed herein, or equivalents thereof.

Figure 11A:
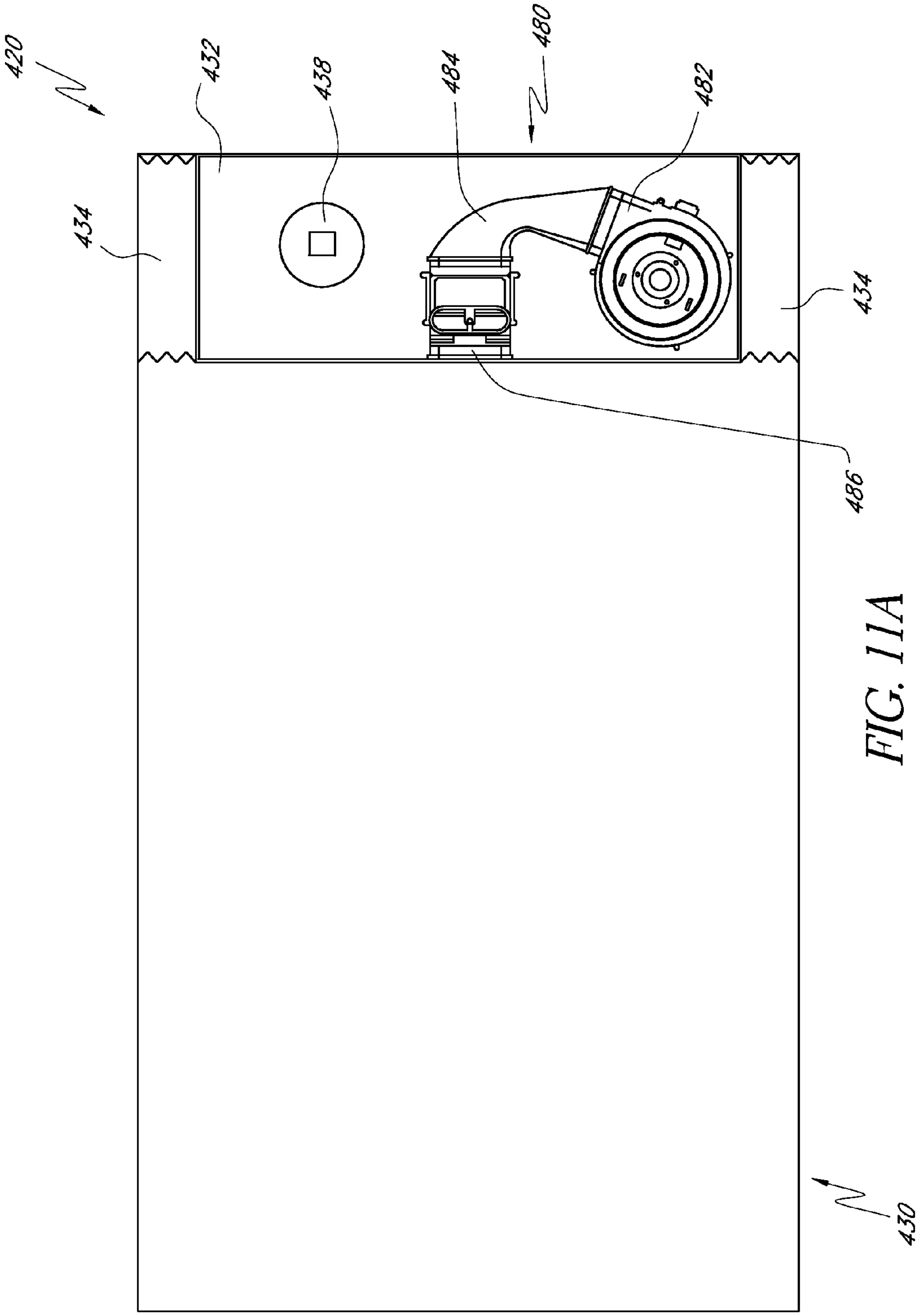
FIG. 11A illustrates a perspective view of a conditioner mat or topper member according to one embodiment.
Figure 11B:
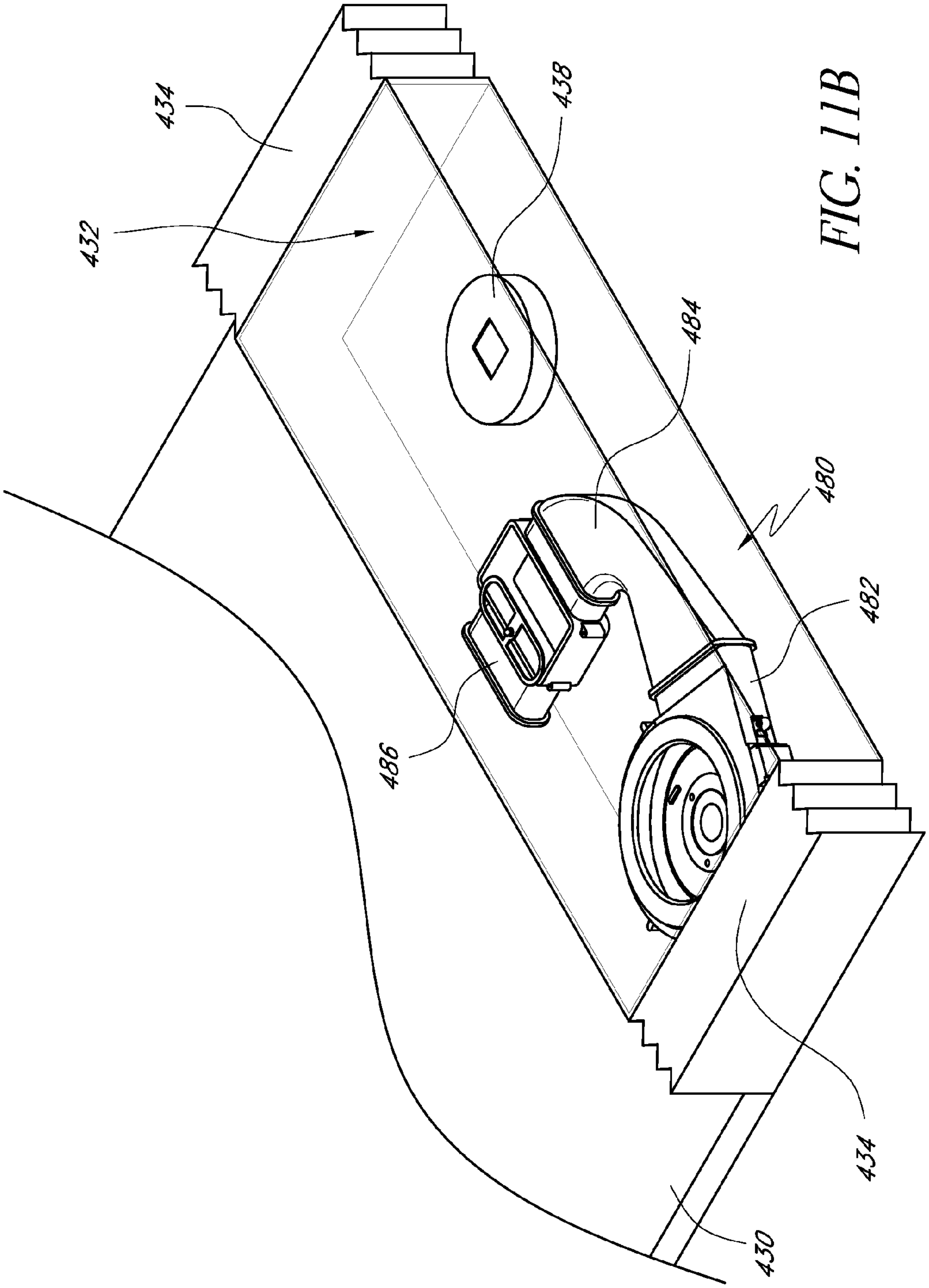
FIG. 11B illustrates a partial perspective view of the conditioner mat or topper member of FIG. 11A.

FIGS. 11A and 11B illustrate another embodiment of a topper member or mat 420 configured to be removably secured to the top of a medical bed, other type of bed or other seating assembly. As discussed herein with reference to other arrangements, the main portion 430 can include one or more fluid zones and/or non-fluid zones (not shown in FIGS. 11A and 11B) that are configured to direct ambient and/or conditioned air or other fluid to targeted regions of an occupant's anatomy. In the configuration depicted in FIGS. 11A and 11B, the fluid module 480 is conveniently positioned within an interior cavity 432 or recessed portion of the topper member 420. The cavity or recess 432 can be formed along an end (e.g., top or bottom) of the mat's main portion 430. Alternatively, such a cavity or other space 432 can be included along a side, middle and/or any other location of the conditioner mat 420, as desired or required.

With continued reference to FIGS. 11A and 11B, the cavity 432 can be defined, at least in part, by a pair of oppositely-mounted enclosure members 434. Regardless of its exact details, the cavity 432 can be configured to advantageously hide all or most (or at least some) of the fluid module 480 and related components, such as, for example, the blower, fan or fluid transfer device 482, the one or more conduits 484 that place the fluid transfer device 482 in fluid communication with the mat's main portion 430, the fluid inlet fitting 486 that establishes an interface with one or more interior spaces of the mat's fluid zones and/or the like. As illustrated in FIGS. 11A and 11B, the cavity 432 can also be provided with a vent 438 that permits ambient air to enter the cavity so as to avoid a negative pressure being created therein.

The various embodiments of a conditioner mat or topper member disclosed herein, or equivalents thereof, can include one or more electrical connections for supplying electrical power to the fluid module(s) and/or any other electric components or devices included and/or associated with the mat. The electrical power supplied to a conditioner mat can come in any form, including AC or DC power, as desired or required. Therefore, a mat can comprise a power supply, a power transformer, a power cord, an electrical port configured to receive a cord and/or the like for electrically connecting the mat's electrical components to a facility's power system. Alternatively, the mat can be supplied with one or more batteries to eliminate the need for a hardwired connection into an electrical outlet while the mat is in use. According to certain embodiments, the battery comprises a rechargeable battery that can be easily and conveniently recharged while the mat is not in use. In some configurations, the battery can be separated and removed from the mat for replacement, recharging (e.g., using a separate charging station or device), repair or servicing, inspection and/or for any other purpose.

A mat can also include one or more wires and/or other electrical connections for incorporating other components into the mat's control system. For example, as discussed in greater detail herein, a mat can be equipped with one or more sensors (e.g., temperature, humidity, condensation, pressure, occupant detection, etc.). In some embodiments, a fluid module, power supply, sensor, other electrical component, device or connection and/or any other sensitive item can be separated and removed from the mat prior to a potentially damaging operation (e.g., washing or cleaning or the mat). For instance, the cavity 432 of FIGS. 11A and 11B can comprise a housing that is detachable from and re-attachable to the mat 420.

Figure 12A:
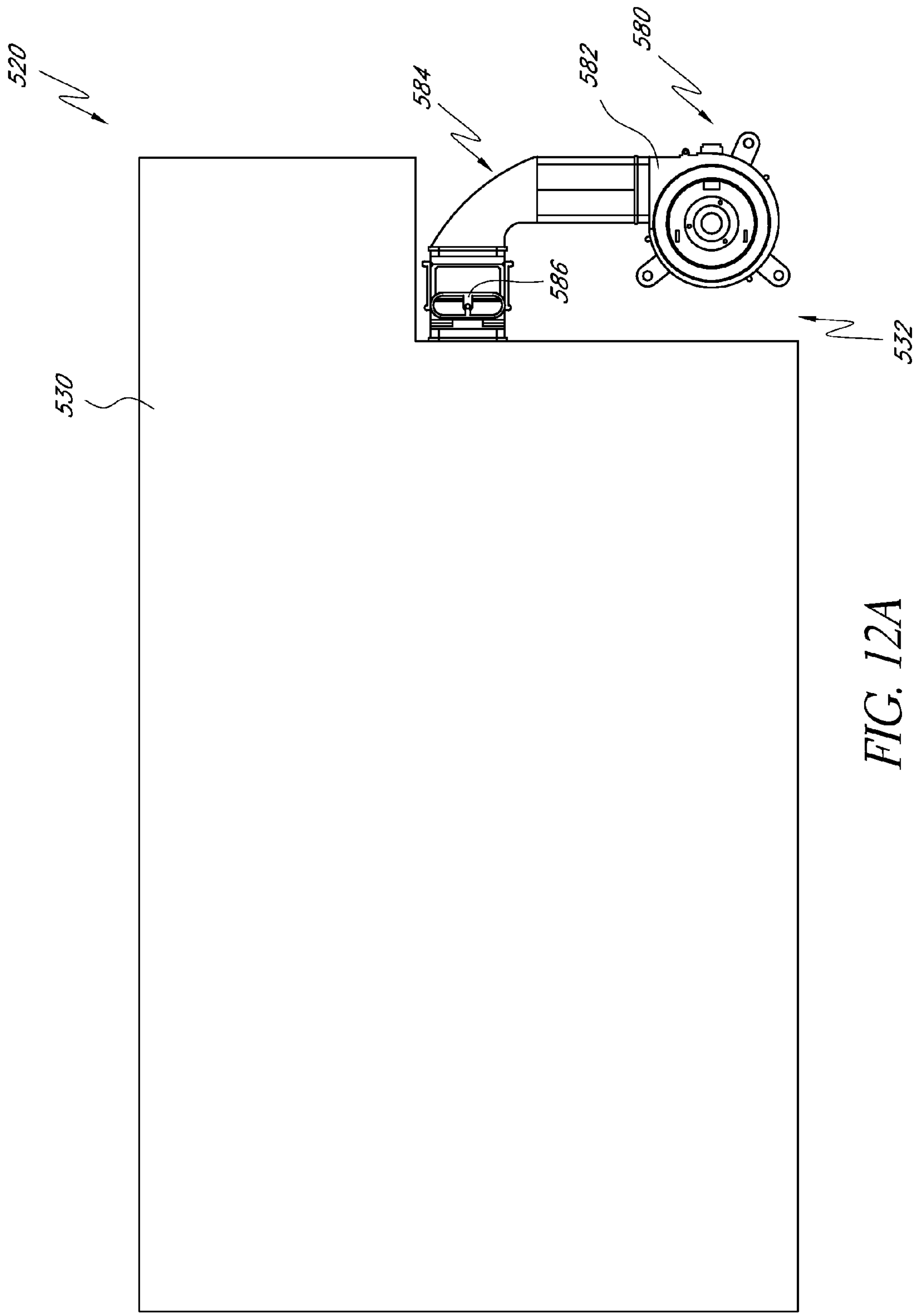
FIG. 12A illustrates a perspective view of a conditioner mat or topper member according to one embodiment.
Figure 12B:
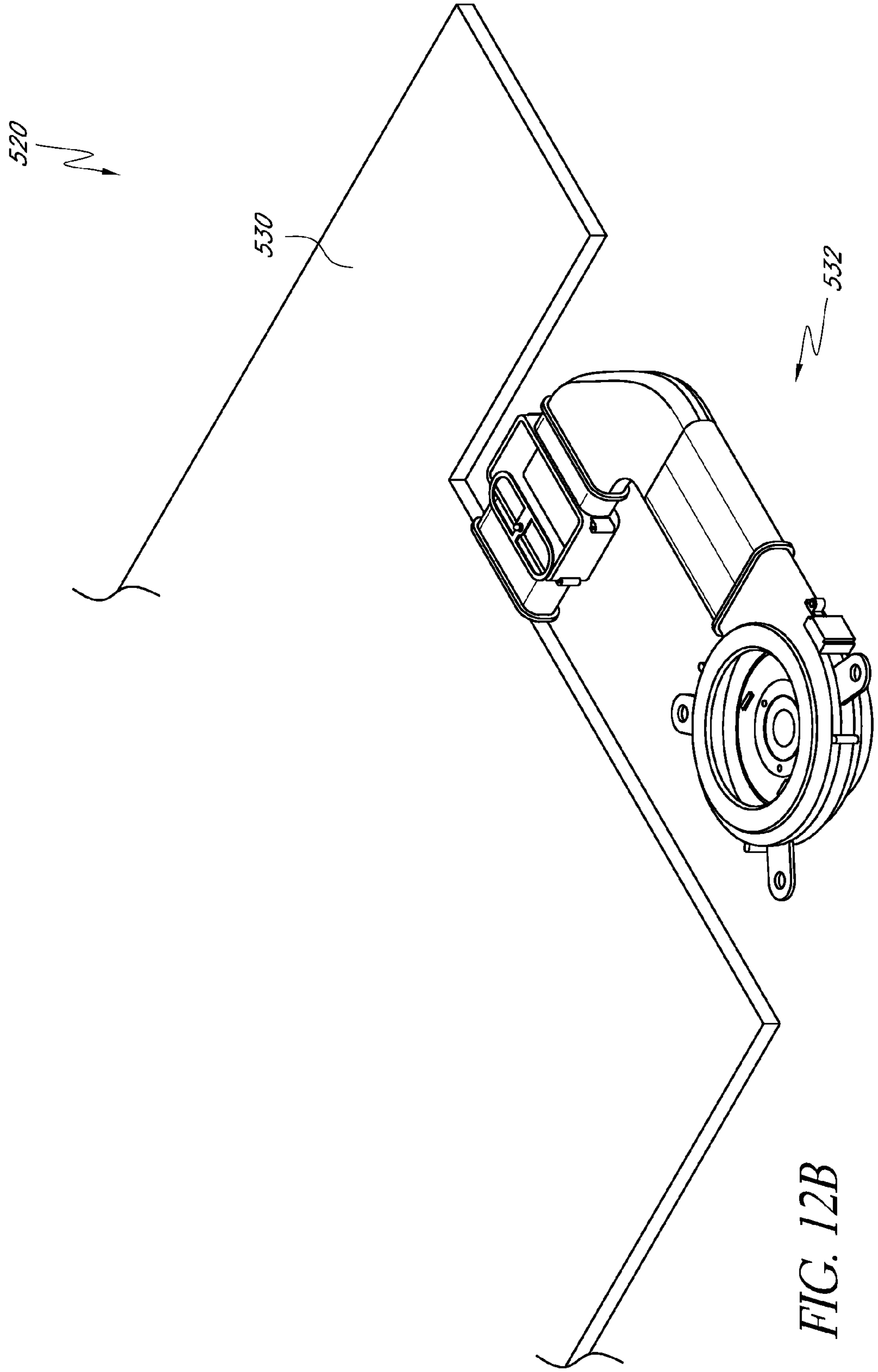
FIG. 12B illustrates a partial perspective view of the conditioner mat or topper member of FIG. 12A.
Figure 13A:
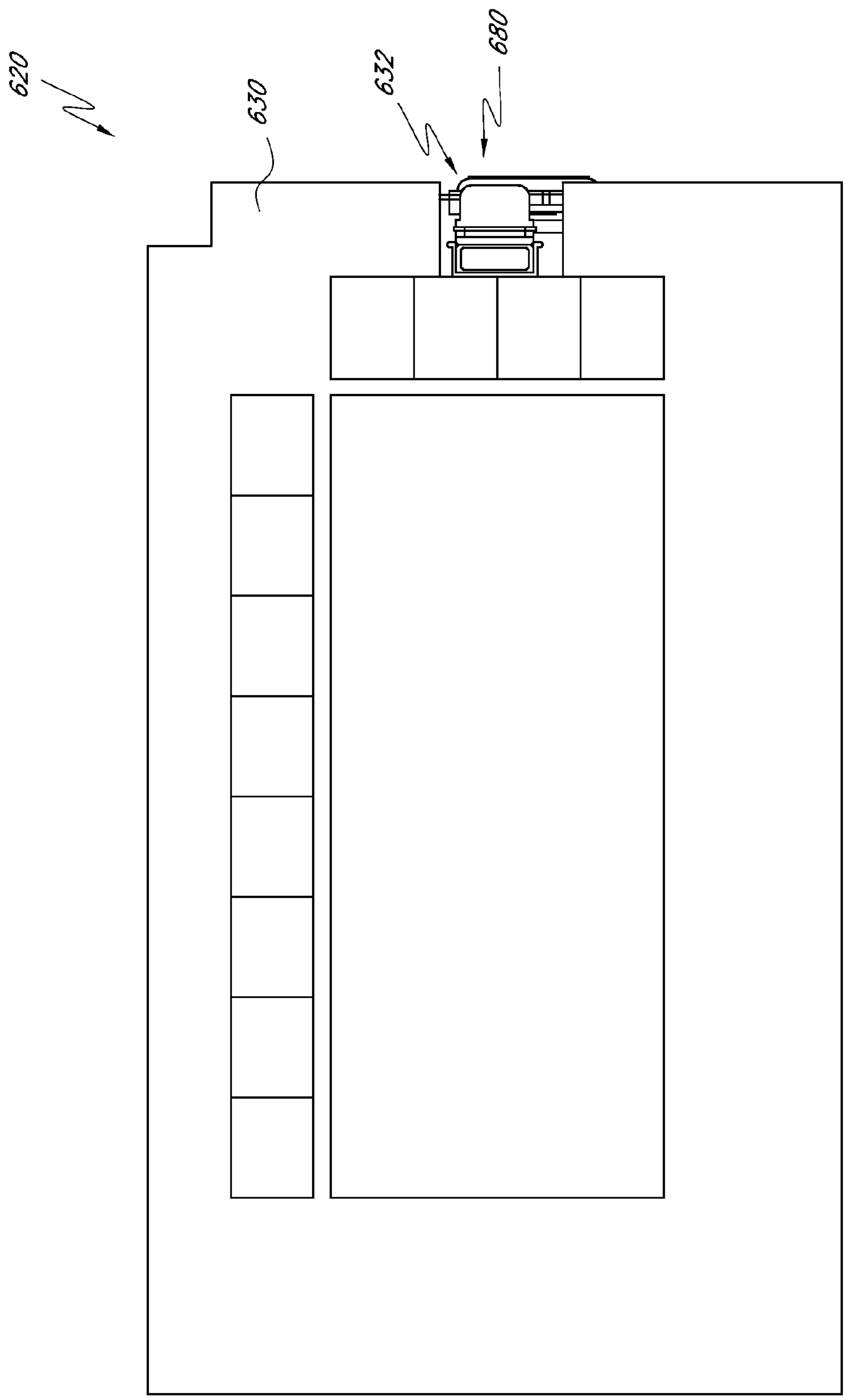
FIG. 13A illustrates a perspective view of a conditioner mat or topper member according to one embodiment.
Figure 13B:
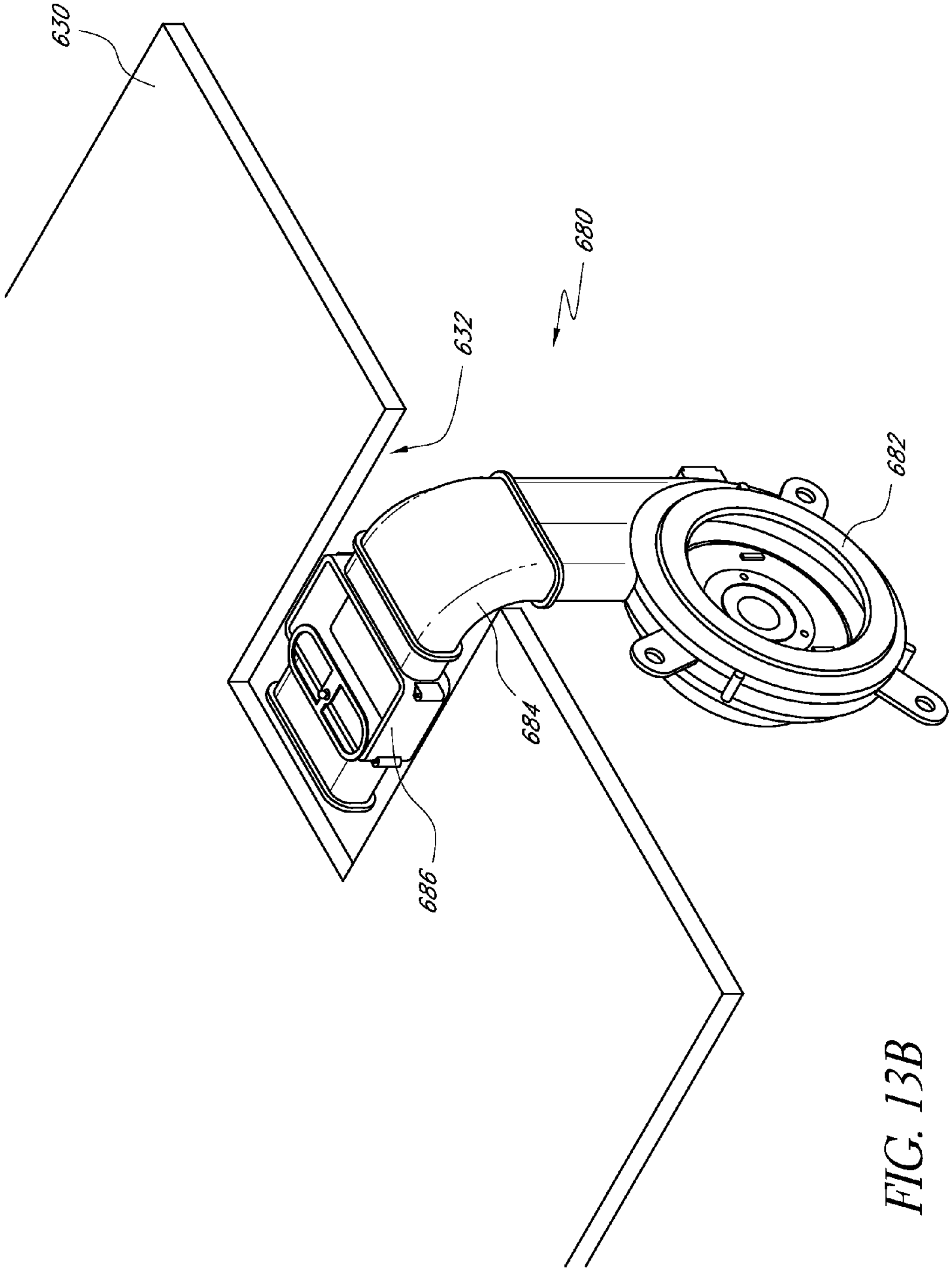
FIG. 13B illustrates a partial perspective view of the conditioner mat or topper member of FIG. 13A.

Another embodiment of a conditioner mat or topper member 520 is illustrated in FIGS. 12A and 12B. As shown, the main portion 530 of the mat 520 can include a cutout 532 or other feature that is sized, shaped and otherwise configured to accommodate a fluid module 580. Accordingly, similarly to the arrangement of FIGS. 11A and 11B, the fluid module 580 can be contained within an outer periphery of a bed when the mat 520 is positioned thereon. The cutout or recess 532 can be positioned along any portion of the mat and need not be confined to a particular corner or region of a main portion 530. The cutout 532 can be situated along a different corner, along a side (e.g., generally between two corners), within an interior region of the main portion 530 and/or the like, as desired. By way of example, the conditioner mat 620 illustrated in FIGS. 13A and 13B comprises a cutout 632 along its front or back end and generally between its two sides. As shown in FIG. 13B, the fluid module 680 can be at least partially situated within the cutout 632. In addition, at least some of the components and portions of a fluid module 680 that selectively supply fluid to the mat 620 can hang along an end or side of the mat 620. For example, in the depicted arrangement, the fluid transfer device 682 and a portion of the conduit 684 are oriented generally perpendicularly relative to the main portion 630.

Figure 14:
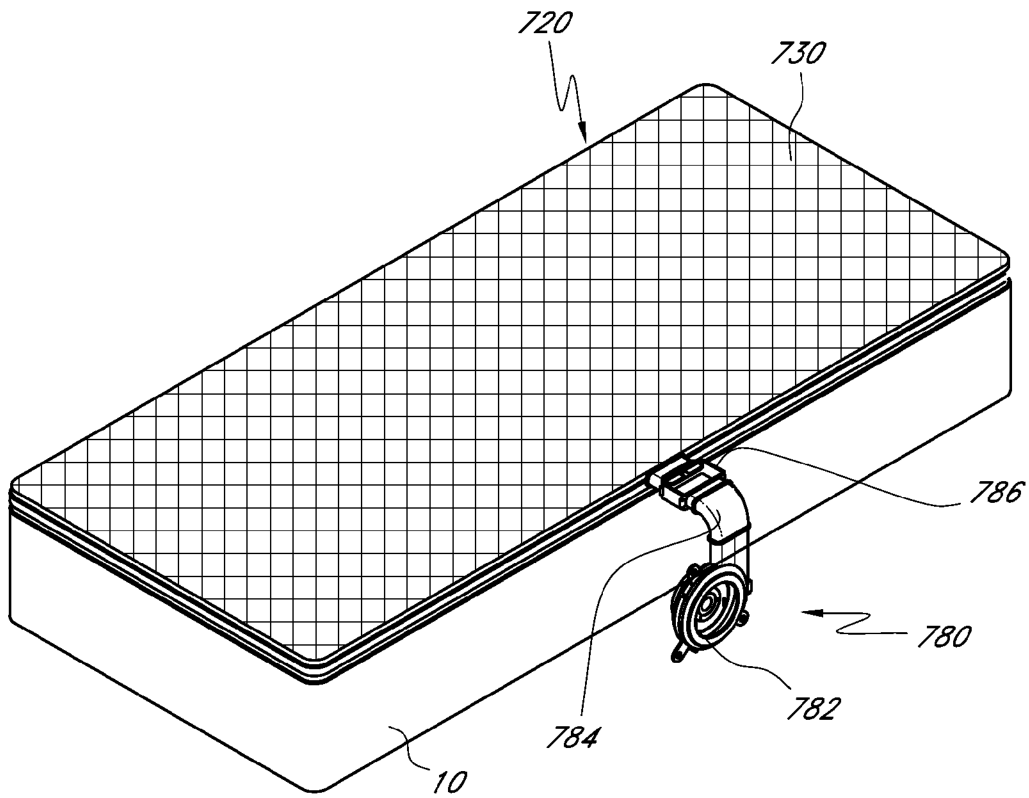
FIG. 14 illustrates a perspective view of a conditioner mat or topper member according to another embodiment.

FIG. 14 illustrates a perspective view of another embodiment of a conditioner mat 720 configured to be positioned along the top of a mattress 10, pad, cushion or other support structure of a bed. As shown, one or more fluid modules 780 can be connected to a main portion 730 along one of the sides of the mat 720. As discussed with reference to other arrangements herein, a fluid module can be positioned along any other portion of the mat 720, either in lieu of or in addition to one of its sides. Similarly to the conditioner mat 620 of FIGS.

13A and 13B, in some embodiments, at least a portion of the fluid module 780 in the depicted embodiment is generally perpendicular to the mat 720. Therefore, for any of the embodiments disclosed herein, or equivalents thereof, a fluid module can be configured to hang along a side or an end of a conditioner mat. In such arrangements, one or more portions or components of the fluid module can be secured, temporarily or permanently, to an adjacent surface, such as, for example, a portion of a mattress or other support structure, a bed headboard or footboard, a bed guardrail, another portion of a bed assembly, the floor or a wall, other equipment located within a hospital room and/or the like.

Figure 15:
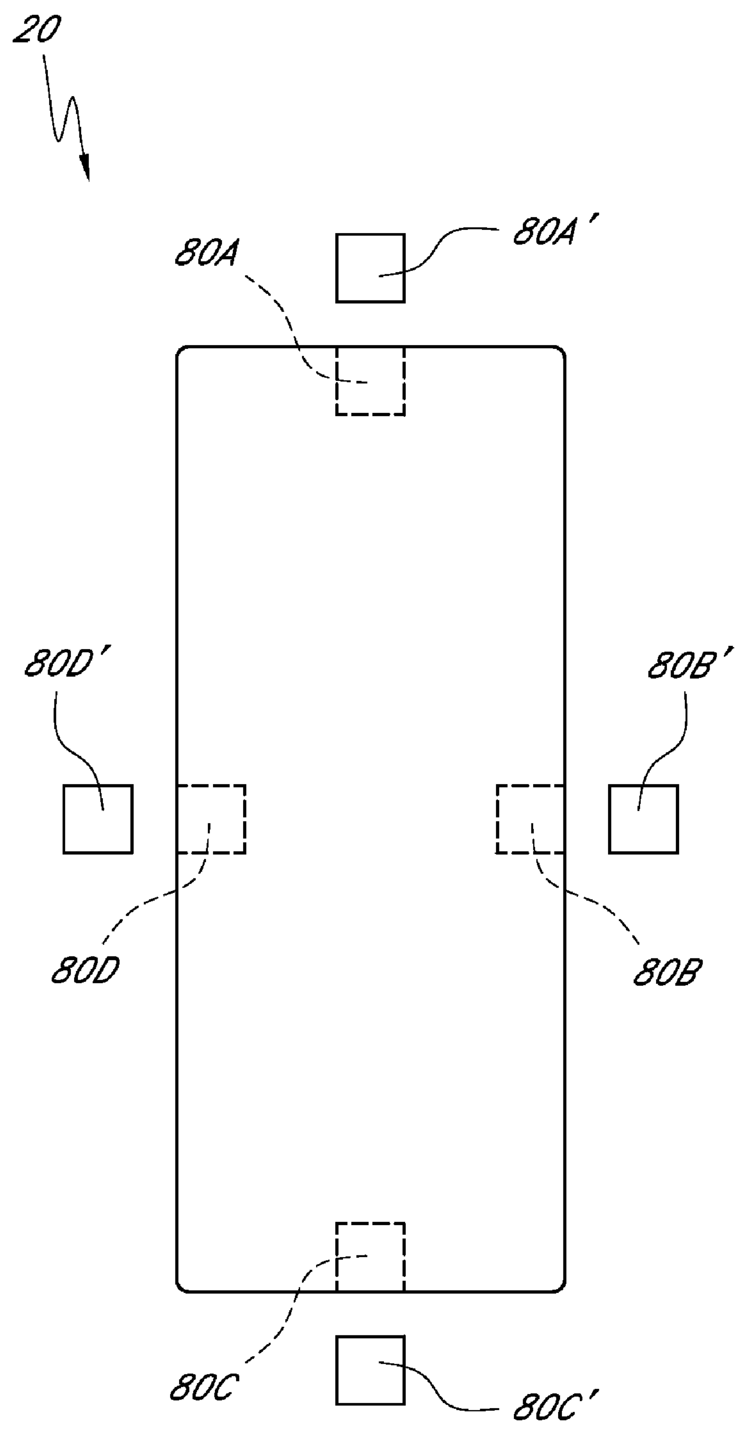
FIG. 15 schematically illustrates possible positions for a fluid module relative to a conditioner mat or topper according to one embodiment.

As illustrated schematically in FIG. 15, a fluid module 80 can be positioned at any location within a main portion 30 of a conditioner mat 20 or at any location adjacent to or near the main portion 30. For example, one or more fluid modules can be situated within a cavity or recess (FIGS. 11A and 11B) or a cutout (FIGS. 12A-13B) of the main portion 30 along the top 80A, bottom 80C and/or the sides 80B, 80D of the mat 20. Alternatively, one or more fluid modules can extend away from the main portion 30 of a mat 20 (e.g., along the top 80A', bottom 80C' and/or the sides 80B', 80D'). For instance, a fluid module can generally hang off the side of the mat and the bed (FIGS. 13A, 13B and 14). In any of the embodiments disclosed herein, a fluid module can be removably or permanently secured to a bed assembly (e.g., mattress or other support member, footboard or headboard, side rail) and/or any other device or surface.

Figure 16A:
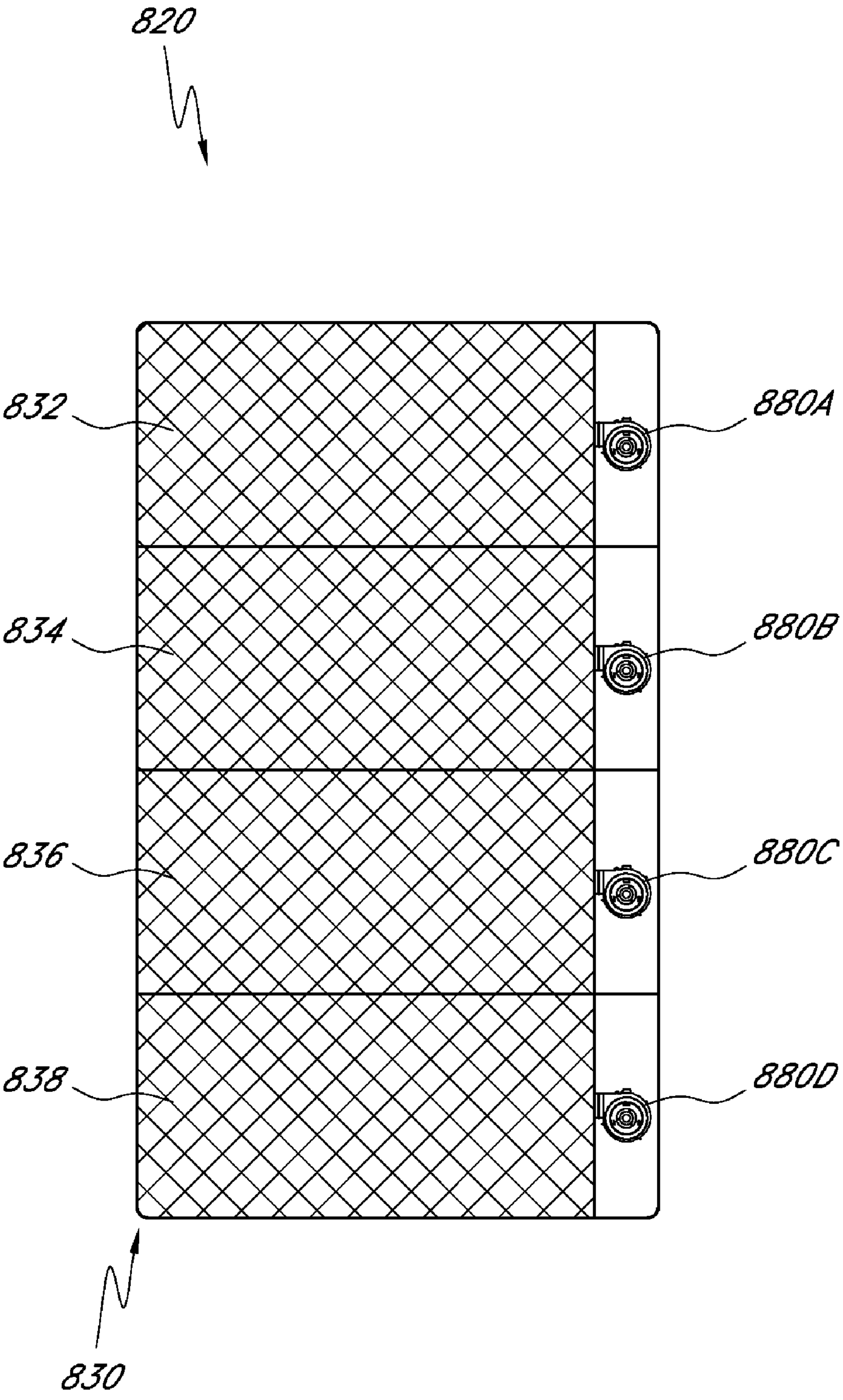
FIG. 16A illustrates a top view of a conditioner mat or topper member according to another embodiment.

FIG. 16A schematically illustrates a plan view of another conditioner mat or topper member 820. As shown, the mat 820 includes four separate fluid zones 832, 834, 836, 838 that are positioned immediately adjacent to each other. One or more non-fluid zones (not shown) can be situated between the fluid zones to provide thermal or fluid isolation, to reduce costs and/or to provide any other benefit, as desired. In FIG. 16A, each fluid zone 832, 834, 836, 838 is supplied ambient and/or conditioned (e.g., cooled, heated, dehumidified, etc.) air or other fluid by one or more dedicated fluid modules 880A, 880B, 880C, 880D. In the illustrated embodiment, the fluid modules are positioned along a side of the mat 820. The fluid modules can be located within a cavity or cutout. Alternatively, the fluid modules 880A, 880B, 880C, 880D can generally form a side edge of the mat 820, can extend outwardly from the mat (e.g., past the outer periphery of the mattress on which the mat is positioned), can hang off the side of the mat 820 and/or the like. In other configurations, the fluid modules can be positioned in a location generally separate and remote from the mat 820. For example, one or more of the fluid modules are located within a fluid box or other container that can be conveniently mounted on the bed assembly (e.g., to, along or near a headboard, footboard, guardrail, etc.), a wall, the floor and/or the like. In such embodiments, the fluid modules can be placed in fluid communication with the respective fluid zones of the mat's main portion 830 using one or more conduits. Additional details regarding fluid boxes are provided herein with reference to the arrangements illustrated in, inter alia, FIGS. 17A, 17B and 19A-27.

Figure 16B:
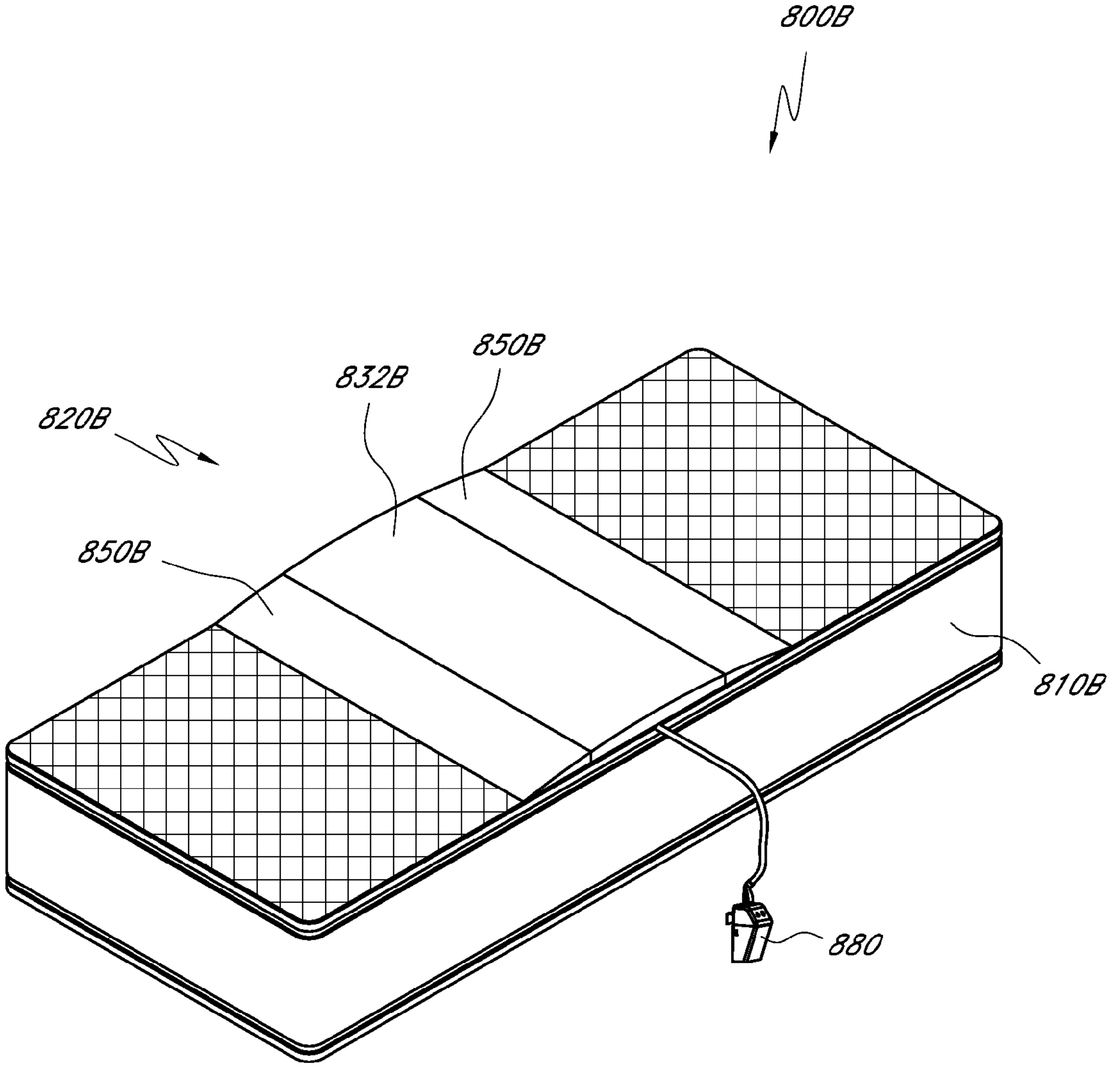
FIG. 16B illustrates a perspective view of one embodiment of a conditioner mat or topper member positioned on a mattress or other support structure of a bed.
Figure 16C:
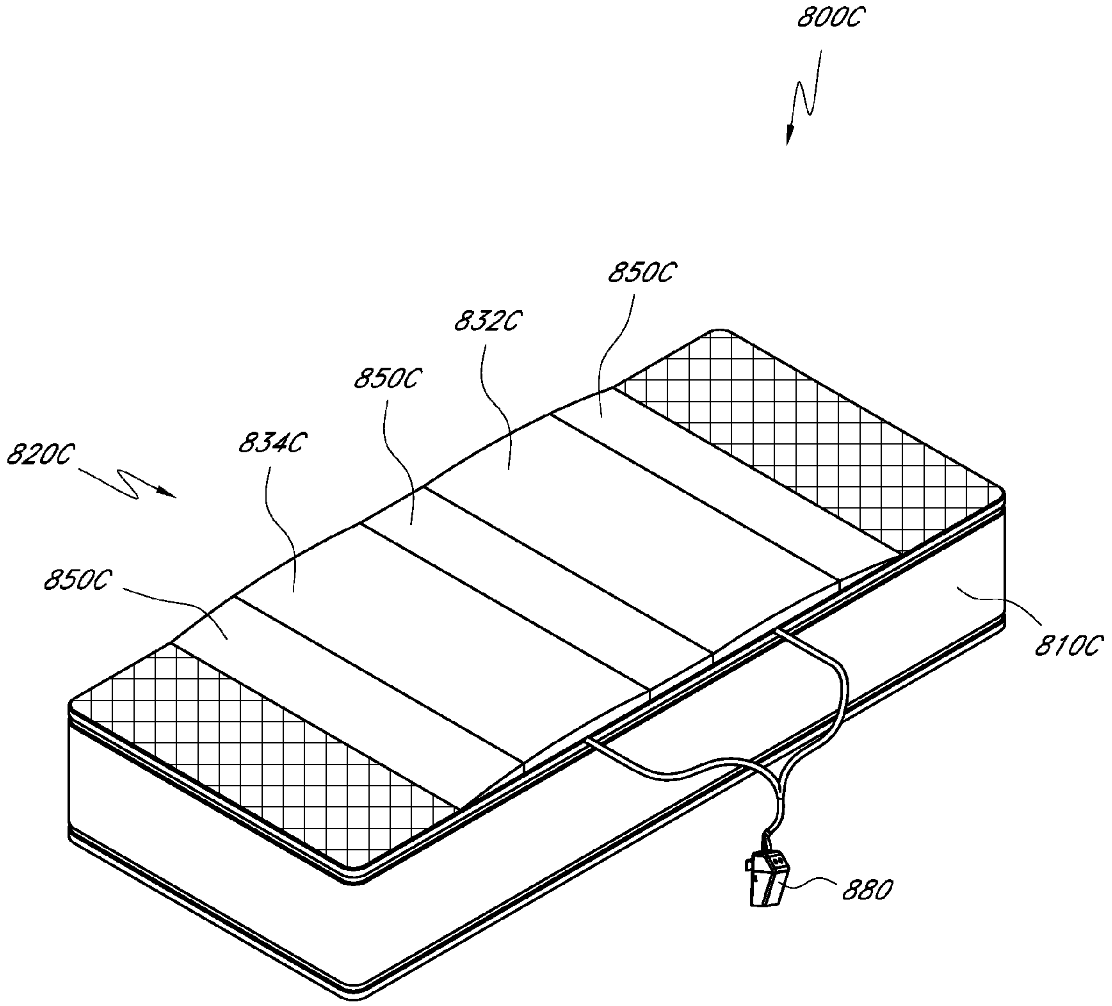
FIG. 16C illustrates a perspective view of another embodiment of a conditioner mat or topper member positioned on a mattress or other support structure of a bed.
Figure 16D:
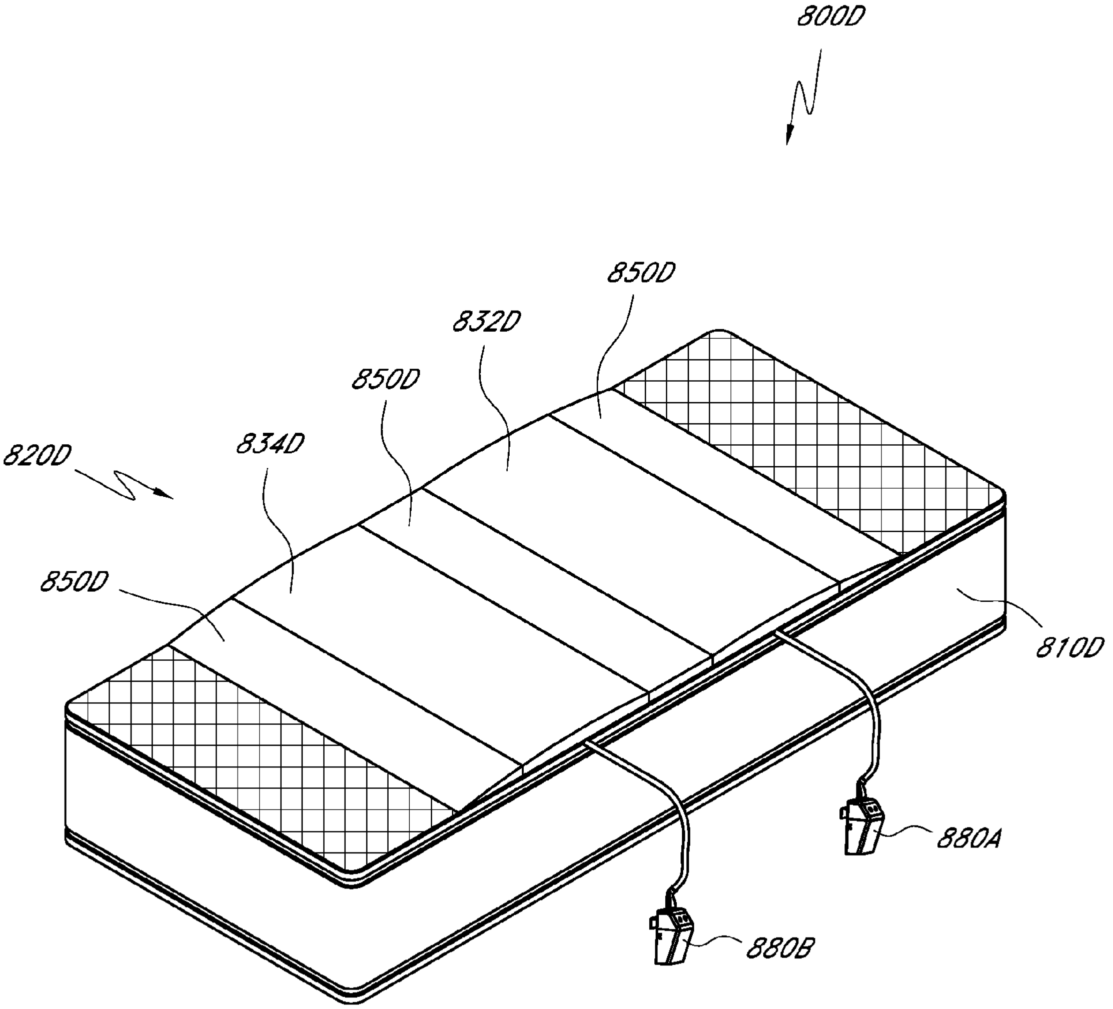
FIG. 16D illustrates a perspective view of yet another embodiment of a conditioner mat or topper member positioned on a mattress or other support structure of a bed.

Additional embodiments of a conditioner mat or topper member 820B-820C configured to be positioned on a medical bed, other type of bed or other seating assembly are illustrated in FIGS. 16B-16D. As depicted in FIG. 16B, the conditioner mat 820B can include a single fluid zone 832B and may be bordered by one or more adjacent non-fluid zones 850B, as desired or required to achieve a particular fluid delivery scheme along an upper portion the bed 800B. The non-fluid zones 850B located at the upper and lower ends of the mat or topper member 820B can have a generally tapered profile to improve the feel and general comfort level to an occupant. Fluid (e.g., ambient and/or conditioned air) is selectively supplied to the fluid zone 832B of the conditioner mat 820B using one or more fluid modules (e.g., blowers or other fluid transfer devices, thermoelectric devices, convective heaters, other thermal conditioning devices, dehumidifiers, etc.), which in some embodiments, are positioned within a fluid box 880, or other enclosure and/or the like.

As discussed in greater detail with reference to other arrangements disclosed herein, the conditioner mat or topper member 820B can be removably attachable to a mattress 810B or other support structure (e.g., pad, cushion, box spring, etc.) of a bed assembly 800B (e.g., hospital or medical bed, typical bed for home use, futon, etc.) using one or more connection devices or methods, such as, for example, straps, hook-and-loop fasteners, zippers, clips, buttons and/or the like. Alternatively, the position of the mat 820B can be maintained relative to the top of a mattress 810B or other support structure by friction (e.g., the use of non-skid surfaces, without the use of separate connection devices or features, etc.). Regardless of how the topper member is secured or otherwise maintained relative to a bed assembly, its size, shape, location relative to the mattress and an occupant positioned thereon and/or other details can be different than disclosed herein, as desired or required.

FIG. 16C illustrates another embodiment of a conditioner mat or topper member 820C for a medical bed, other type of bed or other seating assembly. As shown, the mat 820C can comprise more than one (e.g., two, three, four, more than four, etc.) separate fluid zones 832C, 834C. As discussed in greater detail herein, each fluid zone 832C, 834C can be configured to receive fluid having the same or a different properties (e.g., type, temperature, humidity, flowrate, etc.) than another zone. This can help provide customized ventilation, heating, cooling and/or other environmentally-conditioned schemes to a seated occupant. In the arrangement depicted in FIG. 16C, air or other fluid is selectively delivered to the fluid zones 832C, 834C by one or more fluid modules (not shown) positioned within a fluid box 880. Alternatively, one or more fluid modules providing conditioned and/or unconditioned fluid to the conditioner mat 820C need not be positioned within a fluid box 880 or other enclosure. In addition, as illustrated in FIG. 16D, a conditioner mat 820D can include two or more fluid boxes 880A, 880B, as desired or required. For example, in the depicted embodiment, air from one or more fluid modules housed within a first fluid box 880A is selectively delivered to a first fluid zone 832D of the mat 820D. Likewise, air from one or more fluid modules housed within a second fluid box 880B can be selectively delivered to a second fluid zone 834D. Thus, the type, flowrate, temperature and/or other properties or characteristics of the fluid being delivered to each zone 832D, 834D can be varied in order to achieve a desired ventilation, cooling and/or heating effect along the top surface of the mat or topper member 820C.

As illustrated in the embodiments of FIGS. 16B-16D, the conditioner mat or topper member can be configured to only partially cover the underlying mattress or other support structure of a bed assembly. For example, the topper member can be positioned so that air can be selectively delivered to targeted areas of an occupant's anatomy. In any of the embodiments disclosed herein, or equivalents thereof, the mat or topper member can extend partially or completely across the length and/or the width of the mattress, pad or other bed support member situated therebelow.

Figure 17A:
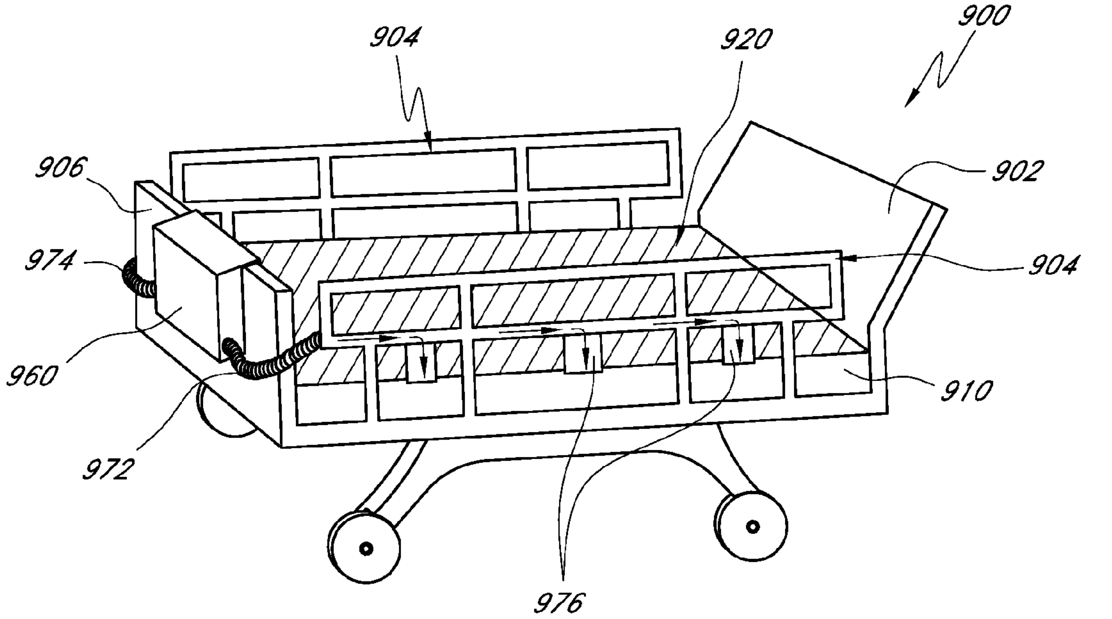
FIG. 17A illustrates a perspective view of one embodiment of a conditioner mat or topper member positioned on a medical bed.
Figure 17B:
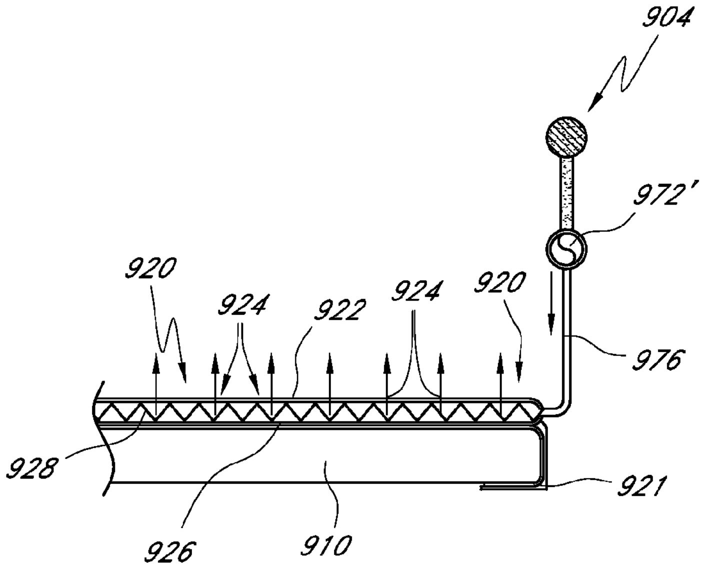
FIG. 17B illustrates a partial cross-sectional view of the conditioner mat and medical bed of FIG. 17A.

FIGS. 17A and 17B illustrate a hospital bed or other medical bed 900 that is configured to receive one embodiment of a conditioner mat or topper member 920. As shown, the conditioner mat 920 is positioned along the top of a mattress 10, pad, cushion or other support structure of the bed 900. The mat 920 can be removably or temporarily secured to the mattress or other support structure 710 using one or more securement devices 921 (e.g., a bottom skirt member such as included in a fitted sheet design), straps (FIG. 7) and/or the like. Further, as with other arrangements disclosed herein, the depicted mat 920 can include one or more fluid zones into which ambient and/or environmentally-conditioned (e.g., cooled, heated, dehumidified, etc.) air or other fluids can be selectively delivered. The fluid zones can comprise spacer materials 928 (e.g., spacer fabric, other porous members or material, etc.) that are generally positioned within a interior space defined by upper and lower layers 922, 926.

With continued reference to FIGS. 17A and 17B, one or more of the bed's guardrails 904, frame members or other support structures can be advantageously configured to receive a fluid conduit 972, 974. Such guardrails 904 or other members can include one or more internal channels or passages through which air or other fluid may pass. Thus, air or other fluid discharged from one or more fluid modules (e.g., located within the fluid box 960 in the depicted embodiment) can be routed through one or more hoses or other conduits 972, 974 to such guardrails 904. Thus, as illustrated in FIGS. 17A and 17B, the hoses or other conduits 972, 974 can be placed in fluid communication with corresponding conduits 972', 974' formed within one or more portions of a guardrail or similar structure. Accordingly, ambient and/or environmentally-conditioned air or other fluids exiting the fluid box 960 can be selectively routed to the guardrail conduits 972', 974'. Air or other fluid entering the fluid passages of the guardrails 904 can be distributed to the interior spaces of the various fluid zones of the mat 920 using one or more intermediate fluid connectors 976 or other fluid branches.

In the arrangement illustrated in FIGS. 17A and 17B, the fluid box 960 is mounted to the footboard 906 of the bed assembly 900. Alternatively, the fluid box 960, and thus the one or more fluid modules positioned therein, can be mounted to the headboard 902, on one of the guardrails 904 and/or any other location (e.g., either on the bed or away from the bed), as desired or required. In addition, as discussed herein with reference to other embodiments, the conditioner mat 920 of FIGS. 17A and 17B can be configured so that it is removable from the mattress 10, the fluid connectors 976 that place the mat 920 in fluid communication with the guardrail conduits 972', 974' and/or any other portion of the bed assembly, for cleaning, other maintenance and/or any other purpose.

Figure 17C:
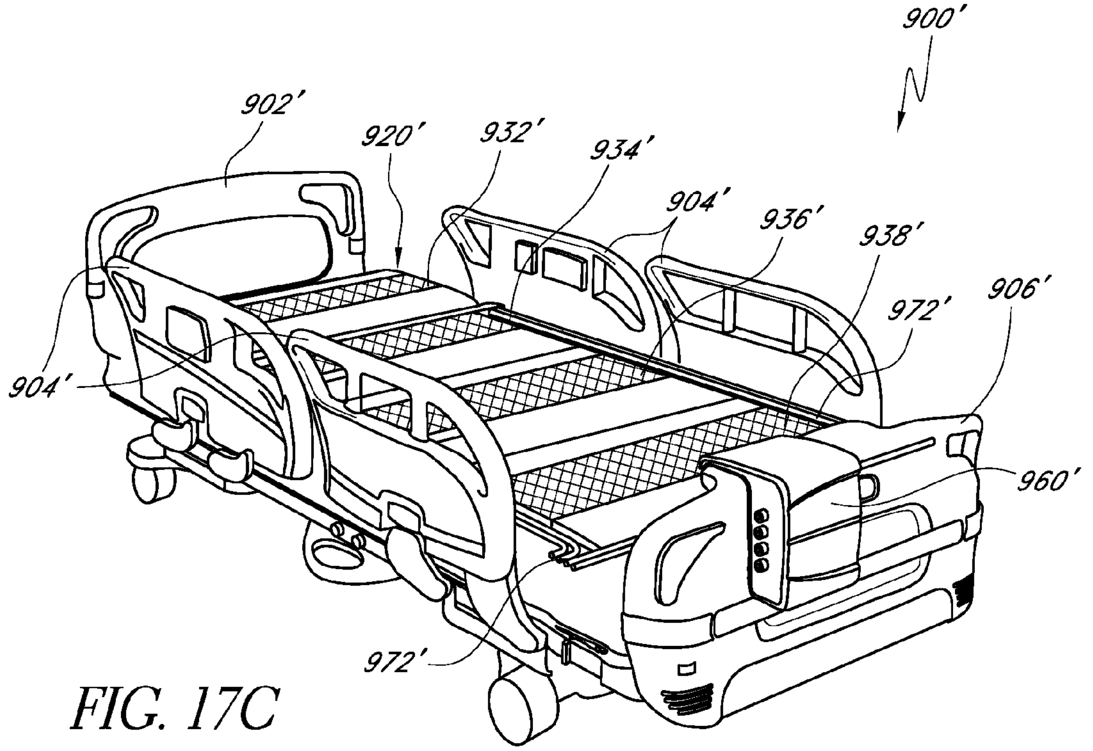
FIGS. 17C and 17D illustrate perspective views of another embodiment of a conditioner mat or topper member positioned on a medical bed.
Figure 17D:
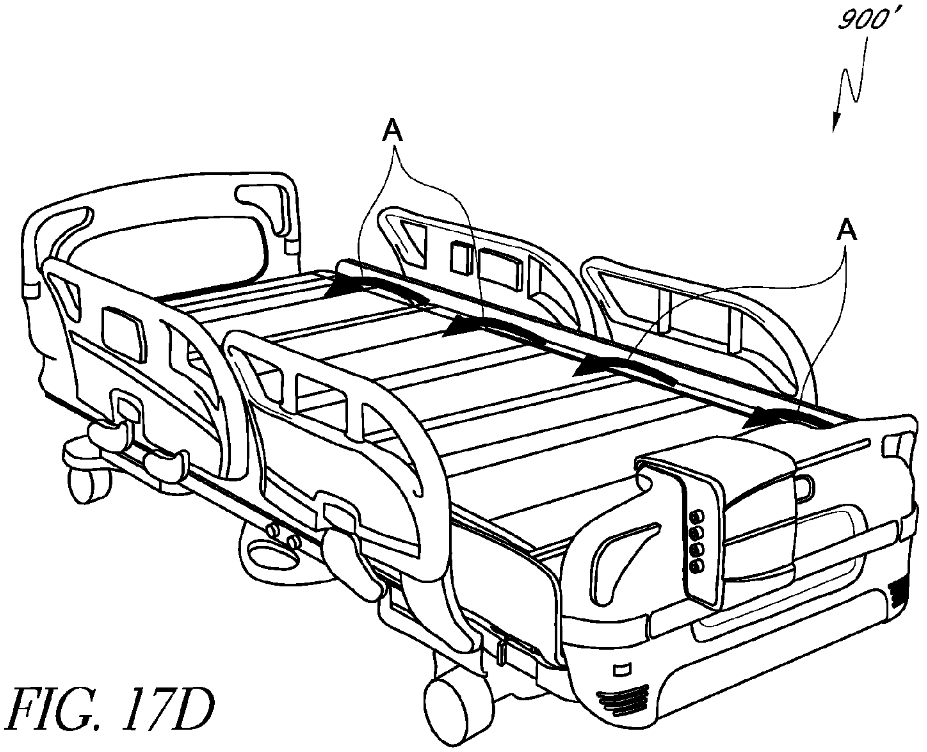
Figure 18A:
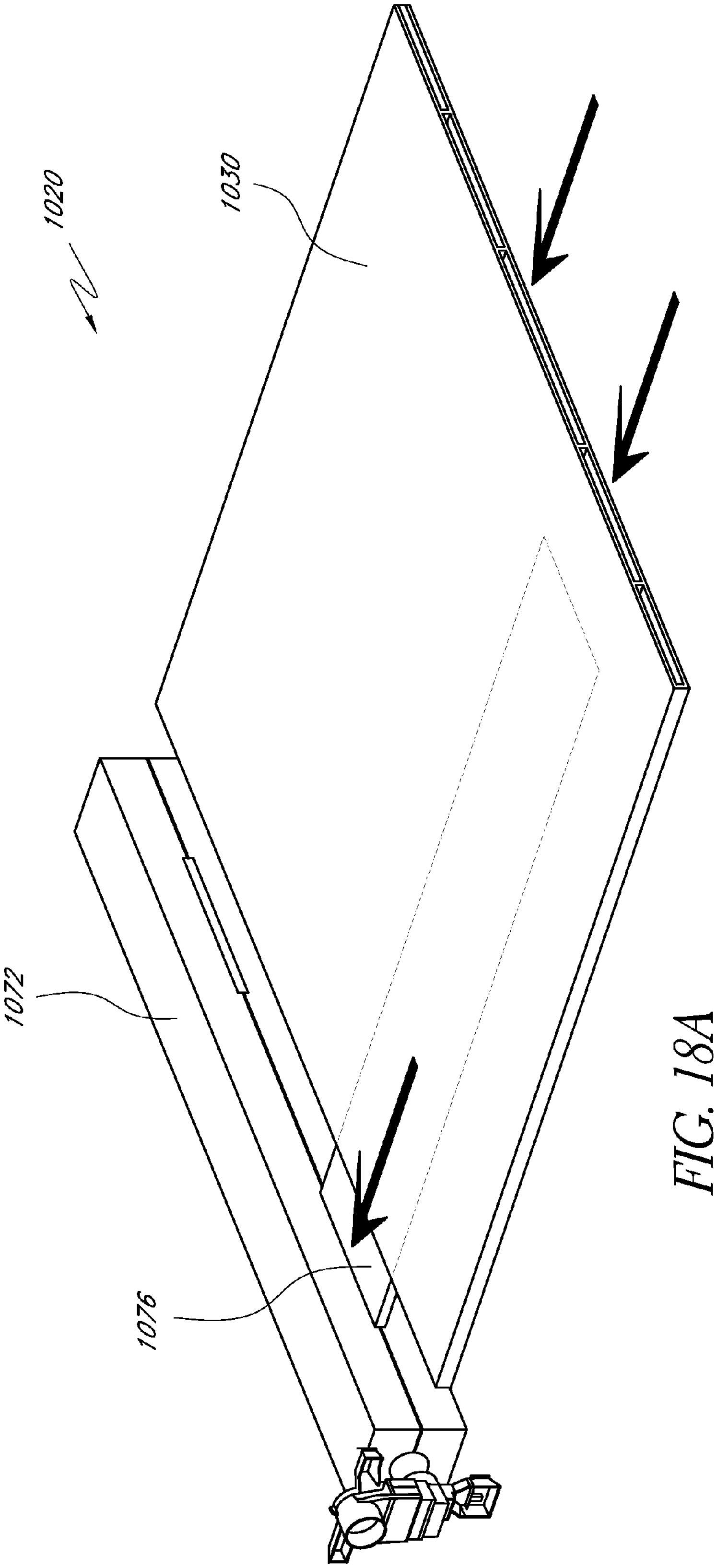
FIGS. 18A and 18B illustrate different perspective views of a conditioner mat or topper member according to one embodiment.
Figure 18B:
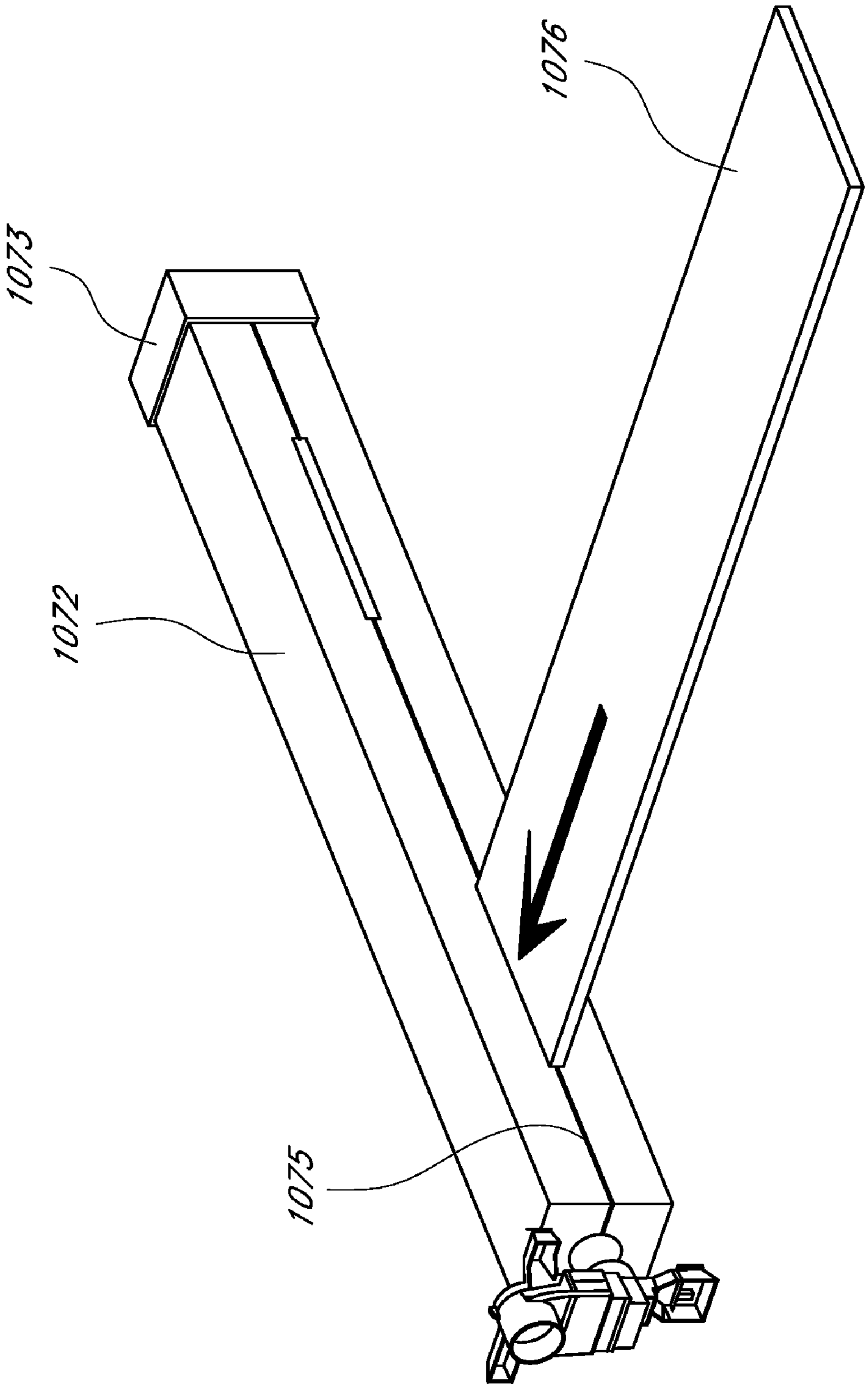
Figure 18C:
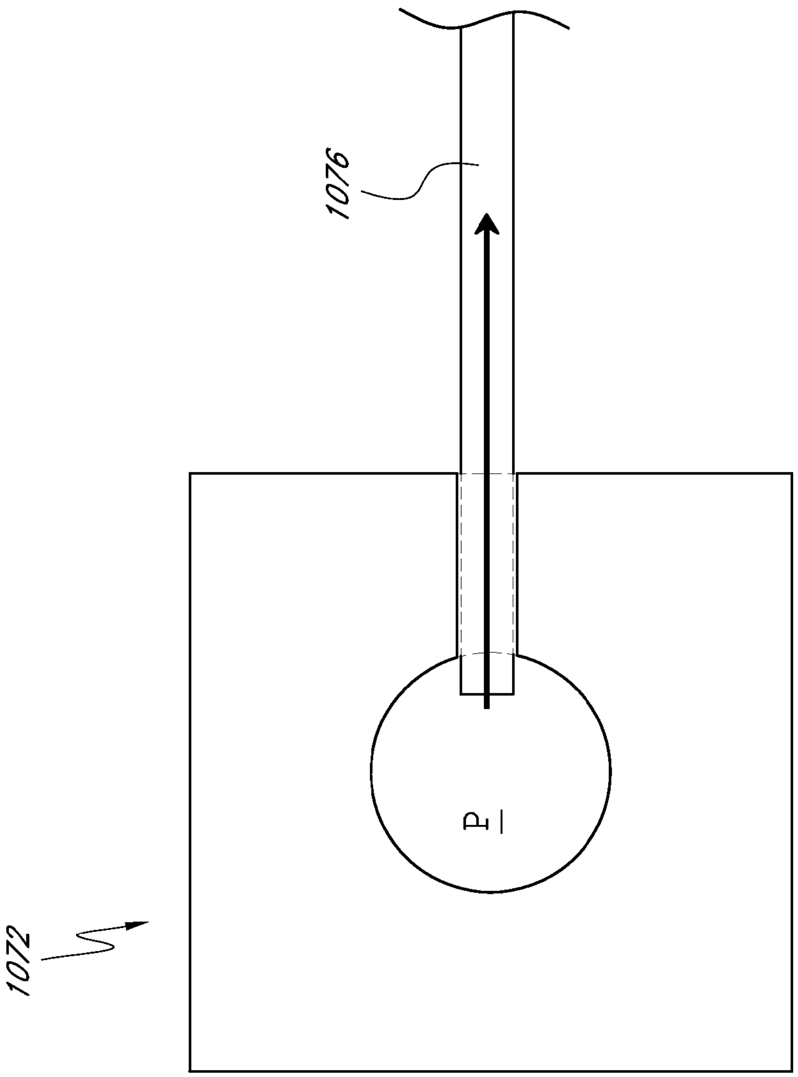
FIG. 18C illustrates a cross-sectional view of the conditioner mat of FIGS. 18A and 18B.
Figure 18D:
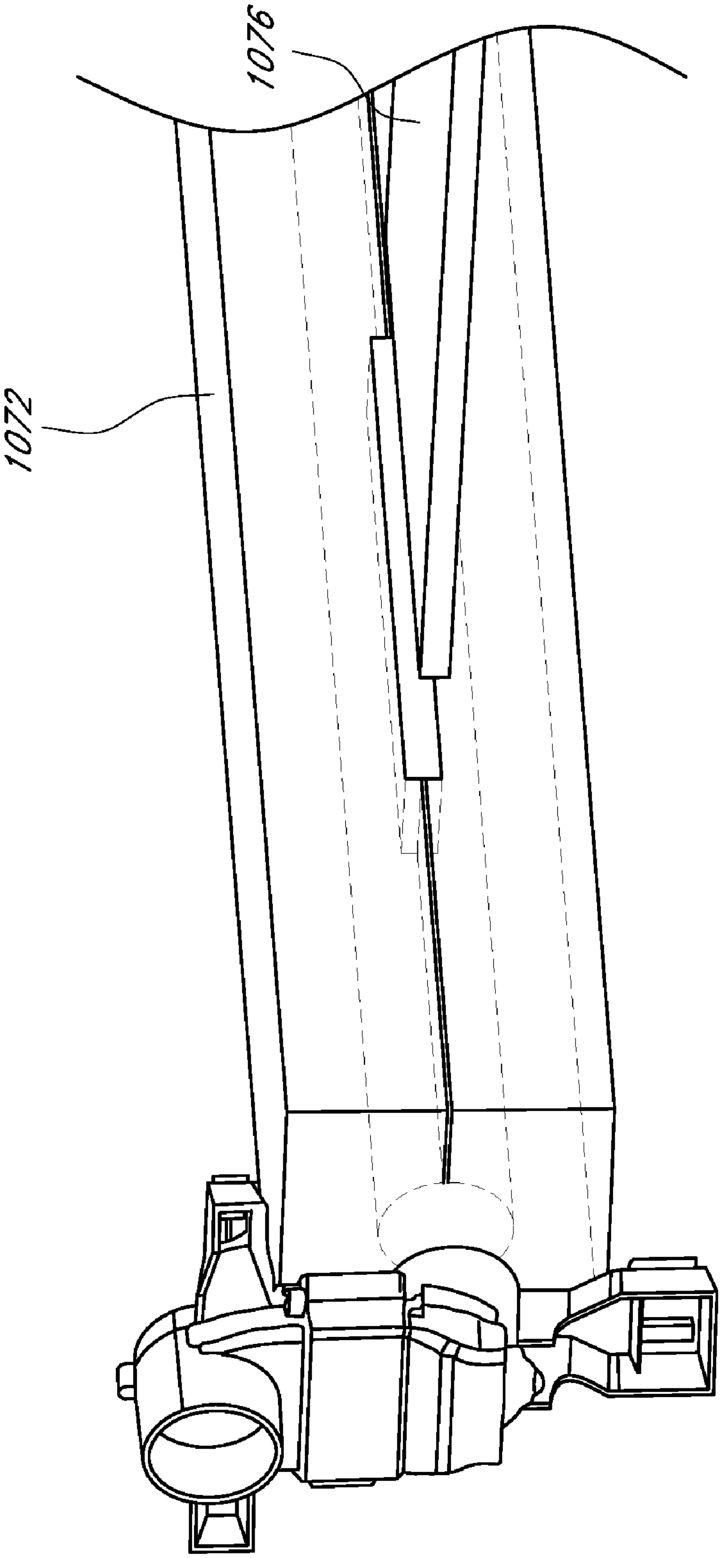
FIG. 18D illustrates another perspective view of the conditioner mat of FIGS. 18A-18C.
Figure 18E:
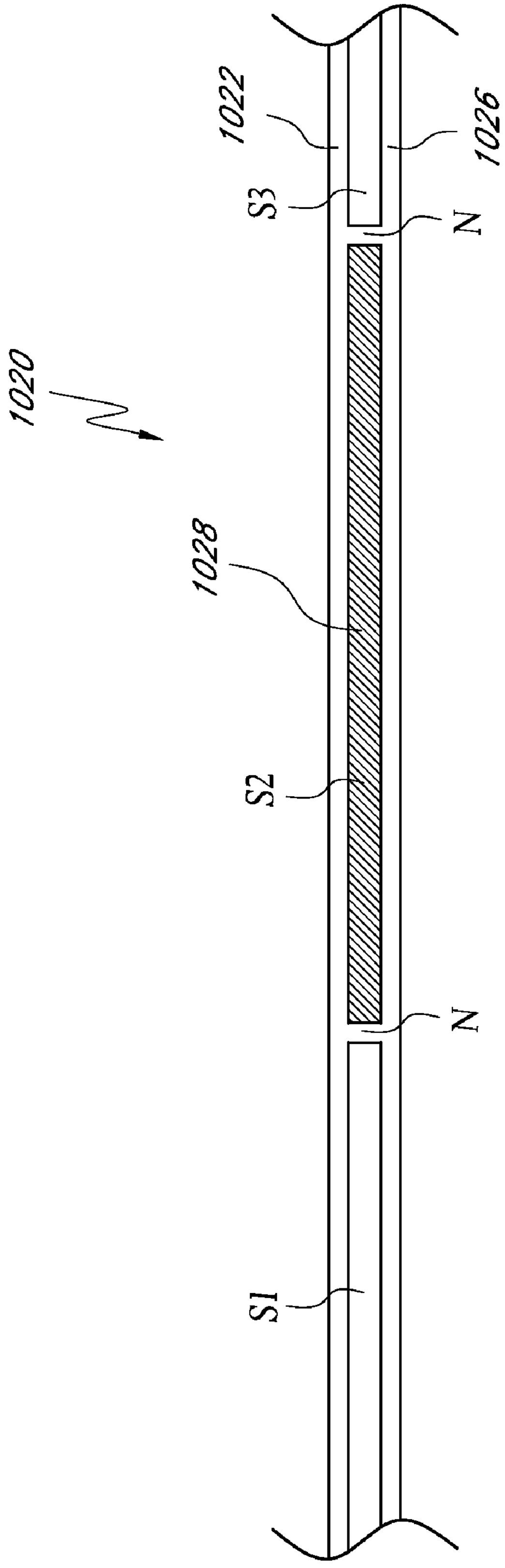
FIG. 18E illustrates another cross-sectional view of the conditioner mat of FIGS. 18A-18D.

FIGS. 17C and 17D illustrate another embodiment of a medical bed 900' configured to selectively provide conditioned and/or unconditioned air or other fluid toward an occupant positioned thereon. As shown, the bed 900' can comprise a conditioner mat or topper member 920' positioned, at least partially, along its top surface. The conditioner mat 920' can include one or more fluid zones 932', 934', 936', 938' and/or non-fluid zones, allowing for customized ventilation and/or thermal or environmental conditioning (e.g., cooling, heating, etc.) schemes along the upper surface of the bed 900'. In the depicted arrangement, air or other fluid is provided to the various fluid zones 932', 934', 936', 938' of the topper member 920' using one or more fluid modules (e.g., blowers or other fluid transfer devices, thermoelectric devices, convective heaters and/or other thermal conditioning devices, dehumidifying devices, etc.) that may be located within, along or near a fluid box 960', another type of enclosure or device, an adjacent surface (e.g., wall, floor, etc.) and/or the like. In FIGS. 17C and 17D, the bed 900' comprises a single fluid box 960' that is removably secured to the footboard 906'. However, the quantity, type, size, shape, location and/or other details of the fluid box 960' and/or the various components located therein can vary, as desired or required.

With continued reference to FIG. 17C, conditioned and/or unconditioned fluid exiting the fluid box 960' can be delivered to the various fluid zones of the conditioner mat 920' using one or more delivery conduits 972'. As discussed in greater detail with reference to other embodiments discussed herein, such delivery conduits 972' can be incorporated into the design of the mat 920' itself. Alternatively, one or more delivery conduits 972' can be physically separated from the conditioner mat 920'. For example, in certain arrangements, the delivery conduits 972' are incorporated into and/or positioned adjacent to a side guardrail 904', footboard 906', headboard 902' and/or any other portion of the bed 900' or other seating assembly. Thus, air or other fluid (e.g., having a general direction of flow schematically represented by arrows A in FIG. 17D) can be selectively transferred from one or more delivery conduits into one or more fluid zones 932', 934', 936', 938'. Air or other fluid can enter an interior space of the conditioner mat 920' along one or more other portions of the bed assembly 900' (e.g., the opposite side, top, bottom, etc.), as desired or required.

FIGS. 18A-18E illustrate various views of another embodiment of a conditioned mat or topper member 1020. The mat 1020 can include a main portion 1030 that comprises one or more fluid zones and/or non-fluid zones (not shown). The main portion 1030 can include upper and lower layers or members 1022, 1026 that generally define one or more interior spaces S1, S2, S3. A spacer material or other fluid distribution member 1028 can be positioned within one or more of the interior spaces defined by the upper and lower layers of the mat's main portion 1030. Such spacer materials or other members can help maintain the shape and integrity of the interior spaces, especially when the mat or topper member 1020 is subjected to compressive loads during use. In addition, as discussed with reference to other configurations herein, the mat 1020 can include one or more fluid boundaries or nodes N that generally create separate fluid zones and/or non-fluid zones within the mat.

With continued reference to FIGS. 18A-18E, the conditioner mat 1020 can include a fluid header 1072 through which ambient and/or environmentally-conditioned (e.g., cooled, heated, dehumidified, etc.) air or other fluid is selectively conveyed. In certain arrangements, such a header 1072 can at least partially form or can be incorporated, at least in part, into a guardrail or other portion of a bed assembly (e.g., hospital bed, other medical bed, other type of bed, other seating assembly, etc.). Thus, as discussed herein with reference to the assembly of FIGS. 17A and 17B, the depicted embodiment can provide a relatively simple and convenient way of delivering fluids to a conditioner mat 1020.

According to certain arrangements, the fluid header 1072 comprises a multi-piece design that allows the internal passage P of the header 1072 to be conveniently accessed by a user. For example, by removing one or more end pieces 1073 and/or other fasteners (not shown), the fluid header 1072 can be opened along a seam 1075 to expose its internal passage P. Thus, one or more intermediate fluid connectors 1076 can be positioned within such a seam, prior re-attaching the adjacent components of the header 1072 to each other. Consequently, the openings within the intermediate fluid connectors 1076 can advantageously place the internal passage P of the header 1072 in fluid communication with one or more fluid zones of the mat's main portion 1030. Thus, as air is delivered from a fluid module into the fluid header 1072, such air can be conveyed to the various fluid zones of the mat 1020 via the fluid connectors 1076. Such a design allows for the conditioner mat or topper member 1020 to be conveniently modified as desired or required by a particular application or use. For example, intermediate fluid connectors 1076 can be quickly and reliably added to or removed from the system. Further, the main portion 1030 of the mat 1020 can be easily removed for cleaning, maintenance, replacement, inspection and/or any other purpose. The fluid header can comprise one or more materials, such as for example, foam, plastic, wood, paper-based materials and/or the like.

As discussed with reference to other configurations herein, the upper and lower layers 1022, 1026 of the conditioner mat 1020 can include plastics (e.g., vinyl), tight-woven fabrics, specially-engineered materials and/or the like. However, in one simplified arrangement, the layers 1022, 1026 of the mat 1020 comprise cotton, linen, satin, silk, rayon, bamboo fiber, polyester, other textiles, blends or combinations thereof and/or other materials typically used in bed sheets and similar bedding fabrics. In some embodiments, such fabrics have a generally tight weave to reduce the passage of fluids thereacross. In one embodiment, one or more coatings, layers and/or other additives can be added to such fabrics and other materials to improve their overall fluid impermeability. Thus, such readily accessible materials can be used to manufacture a relatively simple and inexpensive version of a conditioner mat or topper member 1020. For example, the upper and lower layers can be easily secured to each other (e.g., using stitching, glue lines or other adhesives, mechanical fasteners, etc.) to form the desired interior spaces S1, S2, S3 of the fluid zones. Spacer fabric 1028 or other spacer or distribution materials can be inserted within one or more of the fluid zones, as desired or required. In some embodiments, foam pads, other filler materials and/or the like can be inserted into spaces or chambers of the mat 1020 to create corresponding non-fluid zones.

As with any of the embodiments discussed herein, the spacer fabric 1028 or other spacer materials can be easily removed from the interior spaces prior to washing or otherwise cleaning the mat 1020. However, the spacer fabric 1028 can be left within the corresponding space or pocket of the mat during such cleaning, maintenance, repair, inspection and/or other procedures.

For any of the embodiments of a conditioner mat or topper member disclosed herein, one or more additional layers or members can be positioned on top of the mat. For example, as shown in the exploded perspective view of FIG. 1, a fluid distribution and conditioning member 90 may be situated along the upper surface of the mat 20. Such a conditioning member 90 can help provide a more uniform distribution of fluid flow toward an occupant. In addition, the conditioning member 90 can improve the comfort level to the occupant (e.g., by providing a softer, more consistent feel).

In addition, for any of the topper member arrangements disclosed herein, one or more layers can be positioned immediately beneath the fluid zones to enhance the operation of the topper member. For instance, in one embodiment, a lower portion of the mat (or alternatively, an upper portion of the mattress or other support structure on which the mat is positioned) can comprise one or more layers of foam (e.g., closed-cell foam), other thermoplastics and/or other materials that have advantageous thermal insulation and air-flow resistance properties. Thus, such underlying layers can help reduce or eliminate the loss of thermally-conditioned fluids being delivered into the fluid zones through the bottom of the mat or topper member. Such a configuration can also help to reduce the likelihood of inadvertent mixing of different fluid streams being delivered in adjacent or nearby fluid zones.

According to some embodiments, any of the conditioner mats or topper members disclosed herein, or equivalents thereof, are configured to selectively receive non-ambient air within one or more of their fluid zones, either in lieu of or in addition to environmentally or thermally-conditioned (e.g., heated, cooled, dehumidified, etc.) air or other fluids. For example, a header or other conduit in fluid communication with one or more of the mat's fluid zones can be connected to a vent or register that is configured to deliver fluids from a facility's main HVAC system. Alternatively, a facility can have a dedicated fluid system for delivering air and other fluids to the various topper members and/or other climate controlled seating assemblies. In other arrangements, one or more medicaments or other substances can be added to the ambient and/or conditioned (e.g., heated, cooled, dehumidified, etc.) air or other fluids being delivered (e.g., by a fluid module, HVAC system, etc.) into a topper member. For example, medicines, pharmaceuticals, other medicaments and/or the like (e.g., bed sore medications, asthma or other respiratory-related medications, anti-bacterial medications or agents, anti-fungal medications or agents, anesthetics, other therapeutic agents, insect repellents, fragrances and/or the like). In some embodiments, a climate conditioned bed additionally includes at least one humidity or moisture sensor and/or any other type of sensor. that are intended to help prevent or reduce the likelihood of pressure ulcers can be selectively delivered to a patient through a conditioner mat or topper member. In other embodiments, such medicaments or other substances can be adapted to treat, mitigate or otherwise deal with any related symptoms.

In addition, in some embodiments, it may be beneficial to cycle the operation of one or more fluid modules to reduce noise and/or power consumption or to provide other benefits. For example, fluid modules can be cycled (e.g., turned on or off) to remain below such a threshold noise level or power consumption level. In some embodiments, the threshold or maximum noise level is determined by safety and health standards, other regulatory requirements, industry standards and/or the like. In other arrangements, an occupant is permitted to set the threshold or maximum noise level, at least to the extent provided by standards and other regulations, according to his or her own preferences. Such a setting can be provided by the user to the climate control system (e.g., control module) using a user input device. Additional details for such power conservation and/or noise abatement embodiments are provided in U.S. patent Ser. No. 12/208,254, filed Sep. 10, 2008, titled OPERATIONAL CONTROL SCHEMES FOR VENTILATED SEAT OR BED ASSEMBLIES and published on Mar. 12, 2009 as U.S. Publication No. 2009/0064411, the entirety of which is hereby incorporated by reference herein.

Figure 34:
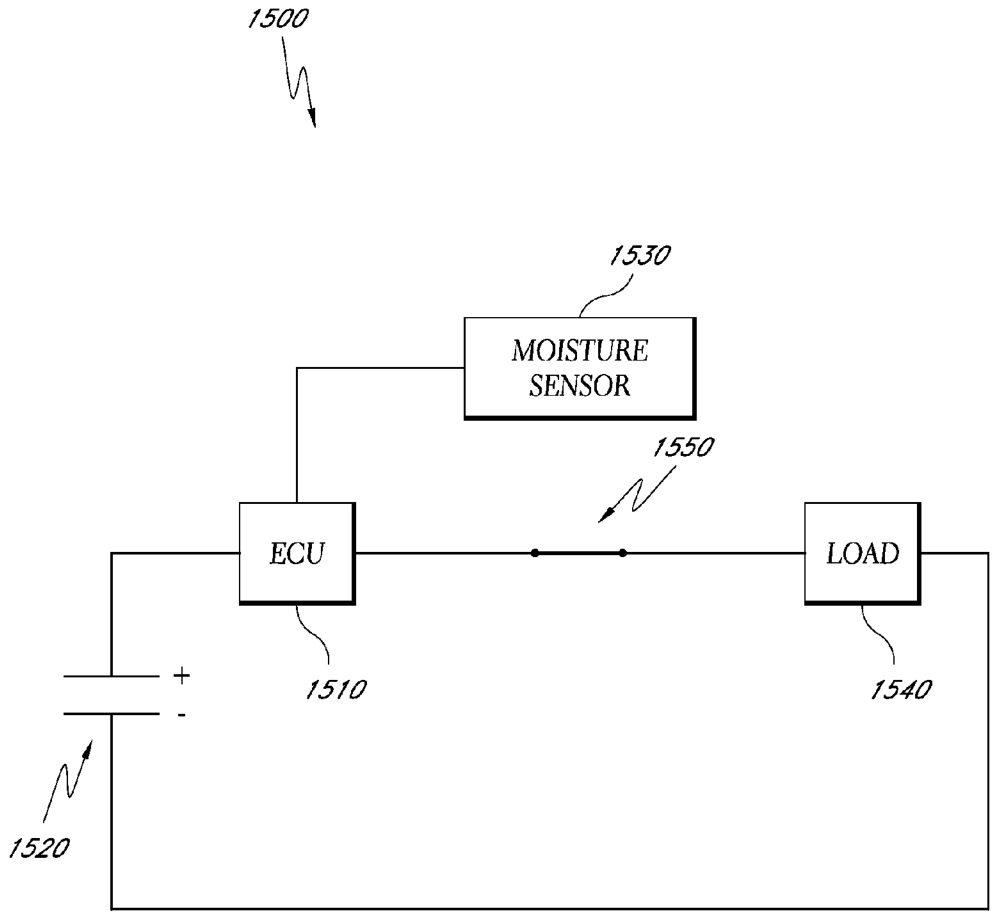
FIG. 34 schematically illustrates one embodiment of a control scheme for the operation of a climate controlled topper member.

One embodiment of a control scheme for operation of one or more fluid modules configured to provide environmentally-conditioned (e.g., heated, cooled, dehumidified, etc.) and/or ambient air to a topper member or mat is schematically and generally represented by the wiring diagram 1500 illustrated in FIG. 34. As shown, in order to reduce power consumption of the climate controlled topper member, to improve its performance, enhance the occupant's comfort level and/or for any other purpose, the system's control unit 1510 (e.g., electronic control unit, control module, etc.) can be adapted to regulate the operation of a fluid module (e.g., a blower or other fluid transfer device, a thermoelectric device, a convective heater or other thermal conditioning device, etc.) and/or any other electric component of device of the system based on, at least in part, input from a moisture sensor 1530 and/or any other type of sensor (e.g., temperature sensor, pressure sensor, occupant-detection sensor, humidity sensor, condensation sensor, etc.). Such control schemes can help avoid excessive use of battery power, over cooling or over heating of the topper member and/or any other undesirable conditions.

With continued reference to the schematic of FIG. 34, a moisture sensor 1530 located on or near the topper member or the bed assembly on which the topper member is positioned can advantageously determine if excessive humidity or moisture is present near the occupant. Accordingly, the sensor 1530 can provide a corresponding feedback signal to the control unit 1510 in order to determine if, when and how the fluid module should be activated or deactivated. For example, is some embodiments, a fluid module can be operated only when a threshold level of moisture, humidity and/or temperature has been detected by one or more sensors 1530. Such a scheme can help extend the useful charge period of a battery or other power source 1520 that supplies electrical power to one or more fluid modules of the system. Such control schemes can also help ensure that potentially dangerous and/or uncomfortable over-temperature or under-temperature conditions do not result when operating a climate controlled conditioner mat or topper member. In addition, such control methods, which in some arrangements incorporate one or more other devices or components (e.g., an electrical load detection device, an occupant detection switch or sensor 1550, other switches or sensors, etc.), can be incorporated into any of the topper embodiments disclosed herein, or equivalents thereof.

In some embodiments, a climate-controlled mat or topper member can include a timer configured to regulate the fluid module(s) based on a predetermined time schedule. For example, such a timer feature can be configured to regulate when a blower or other fluid transfer device, a thermoelectric device, a convective heater or other thermal conditioning device and/or any other electrical device or component is turned on or off, modulated and/or the like. Such timer-controlled schemes can help reduce power consumption, enhance occupant safety, improve occupant comfort and/or provide any other advantage or benefit.

Relatedly, one or more of the components (e.g., fluid transfer device, thermoelectric device, etc.) that can be included in fluid modules, which supply air and other fluids to corresponding mats or topper members, can also be configured to cycle (e.g., turn on or off, modulate, etc.) according to a particular algorithm or protocol to achieve a desired level of power conservation. Regardless of whether the fluid module cycling is performed for noise reduction, power conservation and/or any other purpose, the individual components of a fluid module, such as, for example, a blower, fan or other fluid transfer device, a thermoelectric device, a convective heater and/or the like, can be controlled independently of each other.

Additional details regarding the incorporation of a separate HVAC system into an individualized climate control system (e.g., topper member), the injection of medicaments and/or other substances into a fluid stream and the cycling of fluid modules are provided in: U.S. Provisional application Ser. No. 12/775,347, filed May 6, 2010 and titled CONTROL SCHEMES AND FEATURES FOR CLIMATE-CONTROLLED BEDS; U.S. patent application Ser. No. 12/505,355, filed Jul. 17, 2009, titled CLIMATE CONTROLLED BED ASSEMBLY and published on Jan. 21, 2010 as U.S. Publication No. 2010/0011502; and U.S. patent application Ser. No. 12/208,254, filed Sep. 10, 2009, titled OPERATIONAL CONTROL SCHEMES FOR VENTILATED SEAT OR BED ASSEMBLIES and published on Mar. 12, 2009 as U.S. Publication No. 2009/0064411, the entireties of all of which are hereby incorporated by reference herein.

Figure 19A:
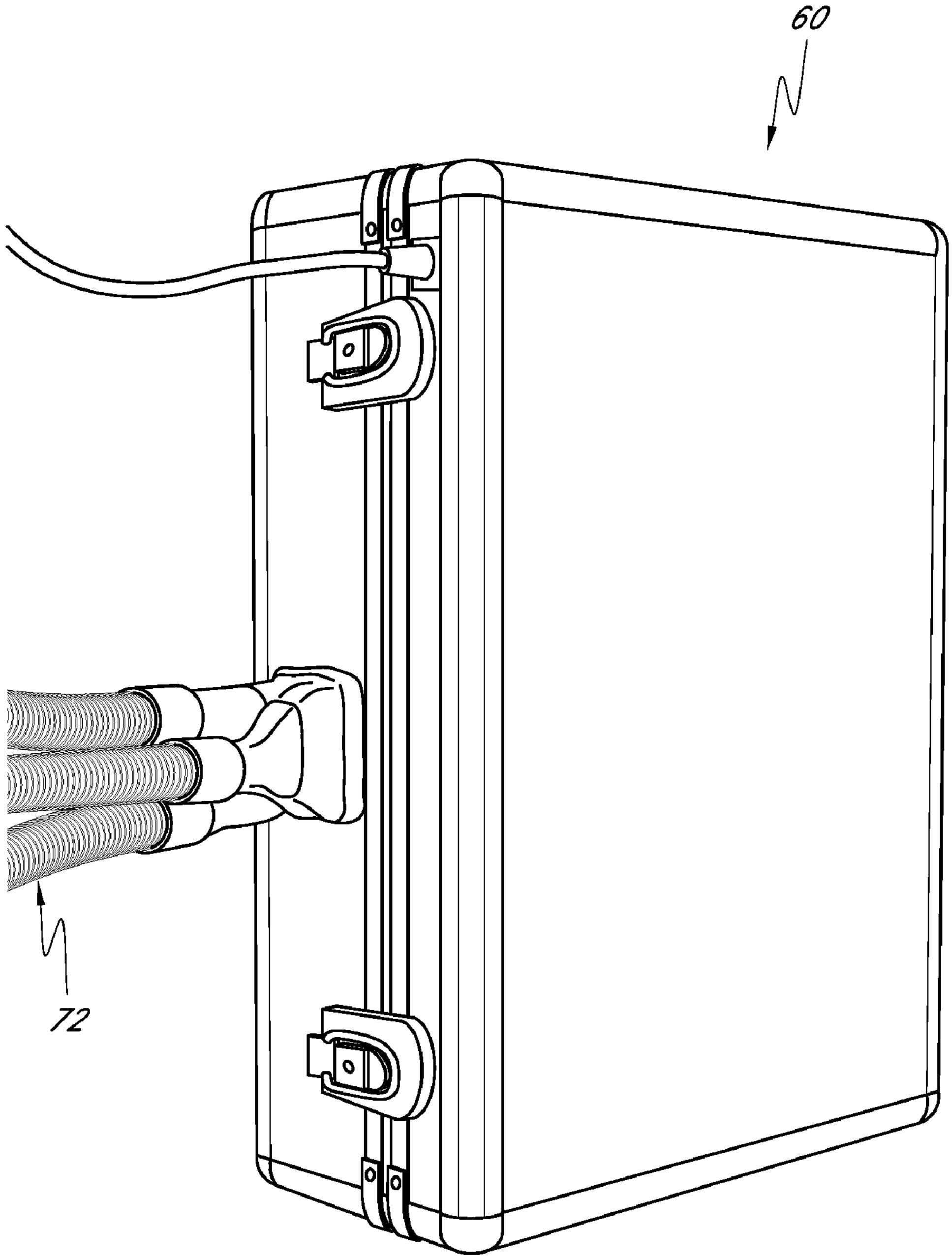
FIG. 19A illustrates a perspective view of a fluid box according to one embodiment.
Figure 19B:
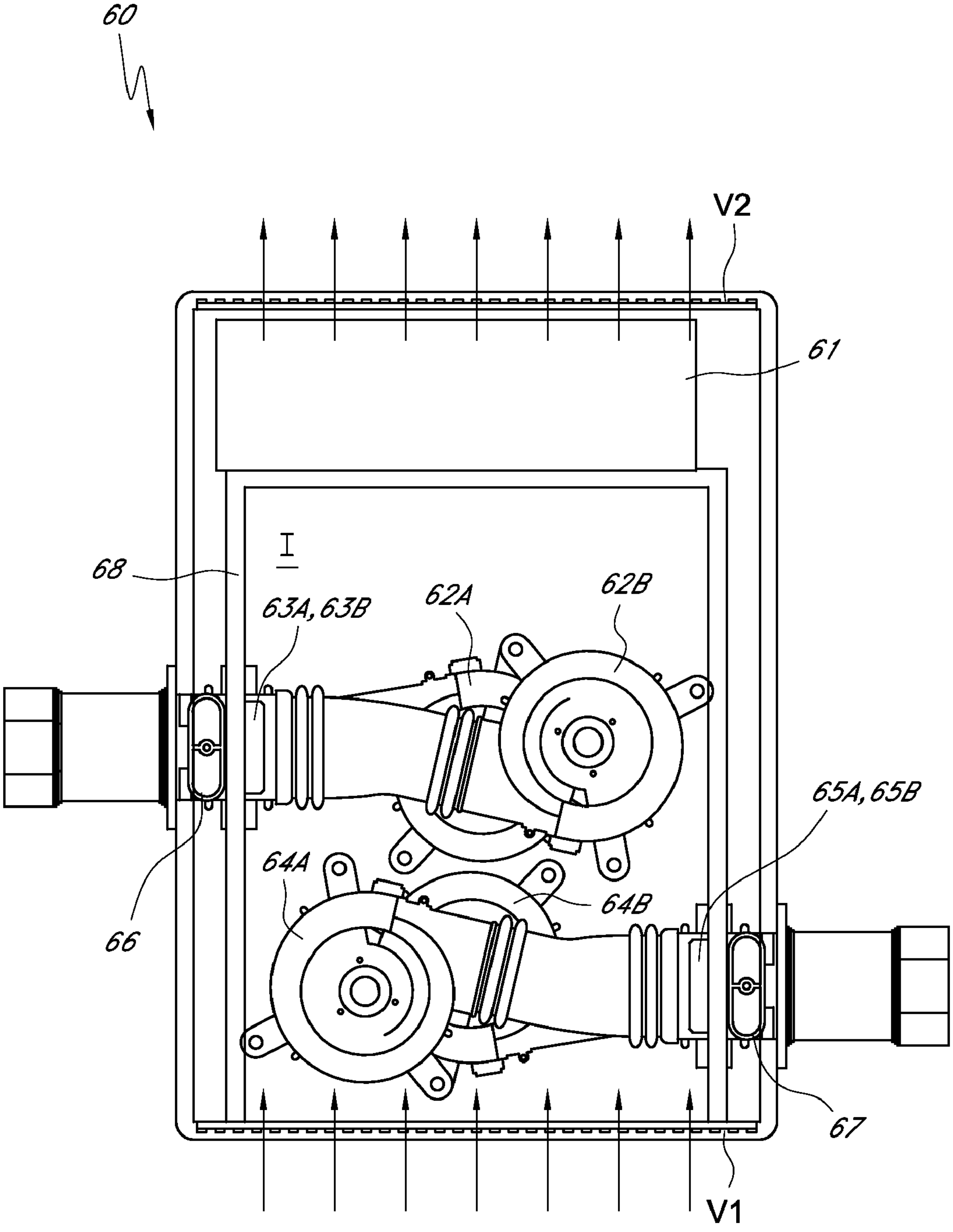
FIGS. 19B and 20 illustrate front views of an interior of the fluid box of FIG. 19A.

FIGS. 19A and 19B illustrate one embodiment of a fluid box 60 that is sized, shaped and otherwise designed to house one or more fluid modules 62A, 62B, 64A, 64B. The depicted fluid box 60 includes a total of four fluid modules within its interior I. As shown, the fluid modules are grouped into two pairs (e.g., a first module pair 62A, 62B and a second module pair 64A, 64B). In some embodiments, such as the one illustrated in FIG. 19B, the first pair (or other grouping) of fluid modules 62A, 62B is configured to selectively deliver ambient and/or environmentally-conditioned air to one side of a conditioner mat (see FIGS. 1 and 2), while the second pair (or other grouping) of fluid modules 64A, 64B is configured to selectively deliver ambient and/or environmentally-conditioned air to the opposite side of a conditioner mat. However, the quantity, spacing, orientation, grouping and/or other details associated with the inclusion of fluid modules within a fluid box can be different than illustrated and discussed herein, as desired or required. For example, each fluid module can be configured to deliver ambient and/or conditioned fluid into only a single fluid zone. In other arrangements, fluid exiting two or more modules can be combined and delivered simultaneously into one or more fluid zones of a conditioner mat.

With continued reference to FIG. 19B, the interior of a fluid box 60 can include one or more layers of insulating materials 68 that are configured to reduce temperature fluctuations within certain portions of the fluid box interior I and/or reduce the noise levels emanating from the fluid box 60 when the fluid modules are operating. In some embodiments, the fluid box can include one or more noise reduction layers, materials, devices or features, either in lieu of or in addition to thermal insulating materials. In some arrangements, the same layers, devices or members are used to provide a desired level of thermal insulation and a desired amount of noise reduction. As shown, a power supply 61, which provides electrical power to the fluid modules 62A, 62B, 64A, 64B and/or any other electrical component associated with the mat's climate control system, can be positioned within an interior I of the fluid box 60. Alternatively, the power supply 61 can be moved outside the box 60 to avoid high heat conditions and other potentially damaging temperature fluctuations resulting from the operation of the fluid modules (e.g., fluid transfer devices, thermoelectric devices, etc.). For example, in one embodiment, the system includes a power supply 61 that is physically separated from the box or other enclosure. In such arrangements, one or more electrical cables, wires and/or other connections are provided to properly connect a power supply to the fluid modules and/or any other electrical components.

Figure 21:
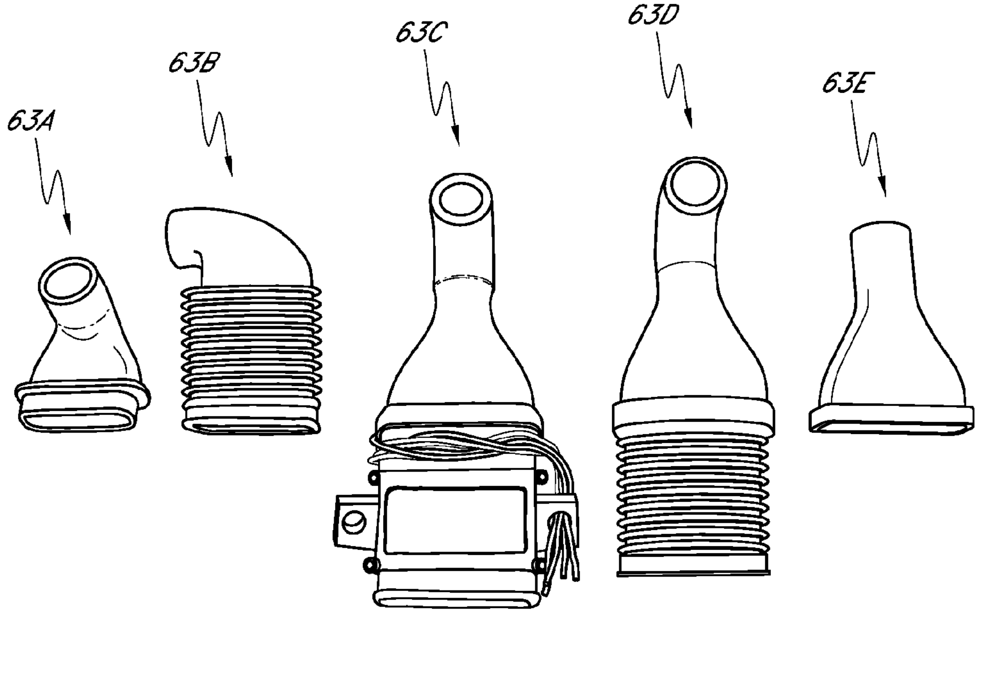
FIG. 21 illustrates various embodiments of outlet fittings.

With continued reference to FIG. 19B, each thermoelectric housing 66, 67 and/or any other portion or component of the fluid module 62A, 62B, 64A, 64B can comprise its own outlet fitting 63A, 63B, 65A, 65B, which, in some embodiments, serves as an interface between the fluid transfer device and the conduit 72, 74 that places the corresponding fluid module in fluid communication with at least a portion of a conditioner mat or topper member. Various non-limiting embodiments of an outlet fitting 63A-63E are illustrated in FIG. 21. As shown, the outlet fittings 63A-63E can include any shape, size, general configuration and/or other features or characteristics, as desired or required for a particular application or use. For example, two of the fittings 63B, 63D comprise bellows, while one of the fittings 63D is configured to accommodate a thermoelectric device.

Figure 20:
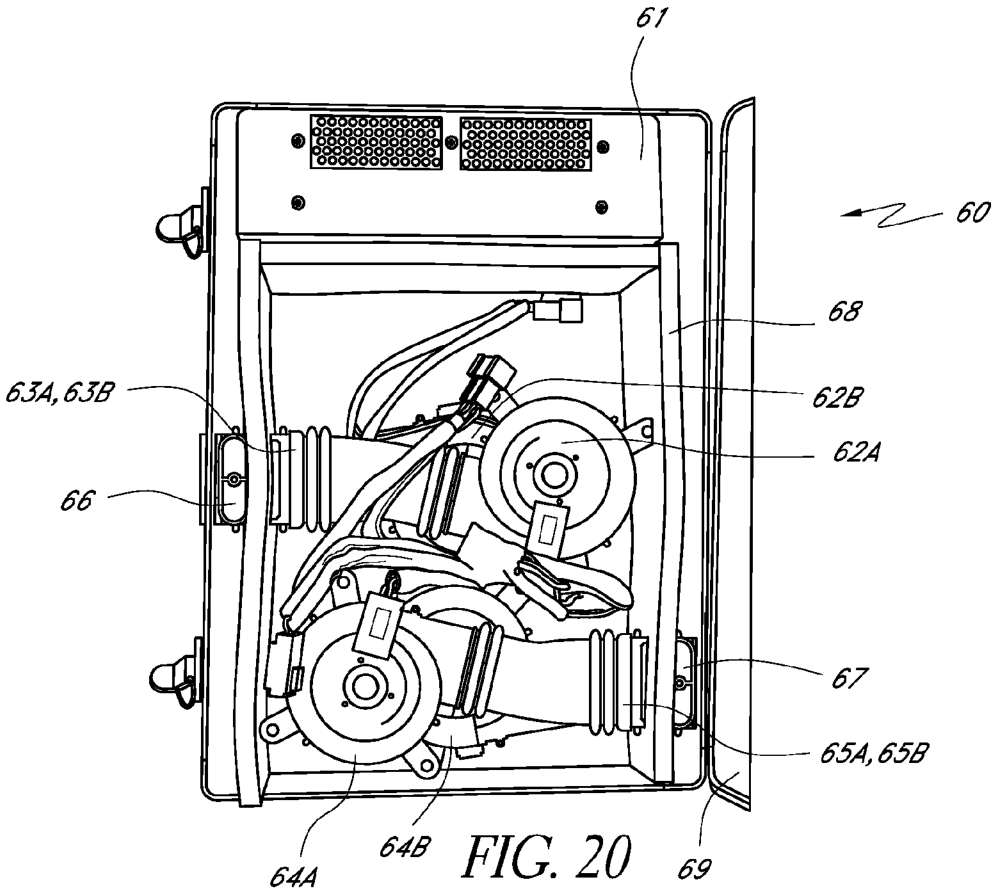

In some embodiments, such as those illustrated in FIGS. 19B and 20, the outlet fittings 63A, 63B, 65A, 65B comprise a thermoelectric device 66, 67 (or a convective heater or any other type of thermal conditioning device) positioned therein. Thus, air and other fluids passing from the respective fluid transfer devices to the outlet fittings can be advantageously heated or cooled, as desired or required. The waste air stream from the thermoelectric devices 66, 67 can be routed to the space generally outside the insulation layer 68 where it can be more effectively and conveniently eliminated from the outlet vents V2 located along the top of the fluid box 60. As shown in FIG. 19B, ambient air can be drawn into an interior I of the fluid box 60 through one or more inlet vents V1 located along the bottom of the box. Further, in order to increase the use of generally less-expensive, commercially-available materials, the downstream end of the outlet fittings 63A-63E (see, e.g., FIG. 21) can include standard 1-inch or 2-inch diameter rubber tubing or other commercially available conduits. This can help reduce manufacturing and maintenance costs. In other embodiments, however, one or more non-standard conduits can be used. In addition, as shown in FIG. 20, a fluid box 60 can include a hinged door 69 or similar device to facilitate access to its interior I.

Figure 22:
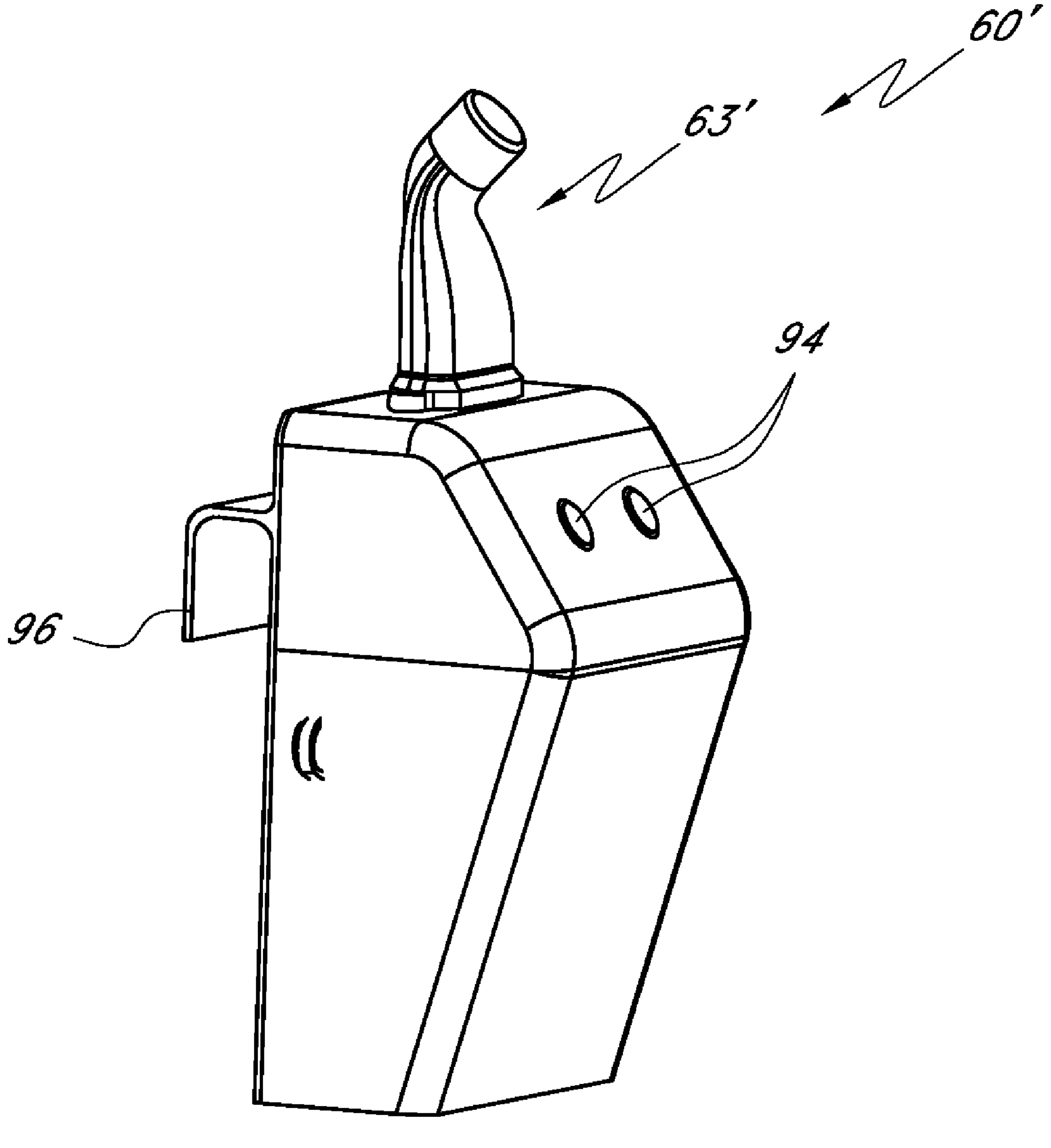
FIG. 22 illustrates a perspective view of a fluid box according to another embodiment.
Figure 23B:
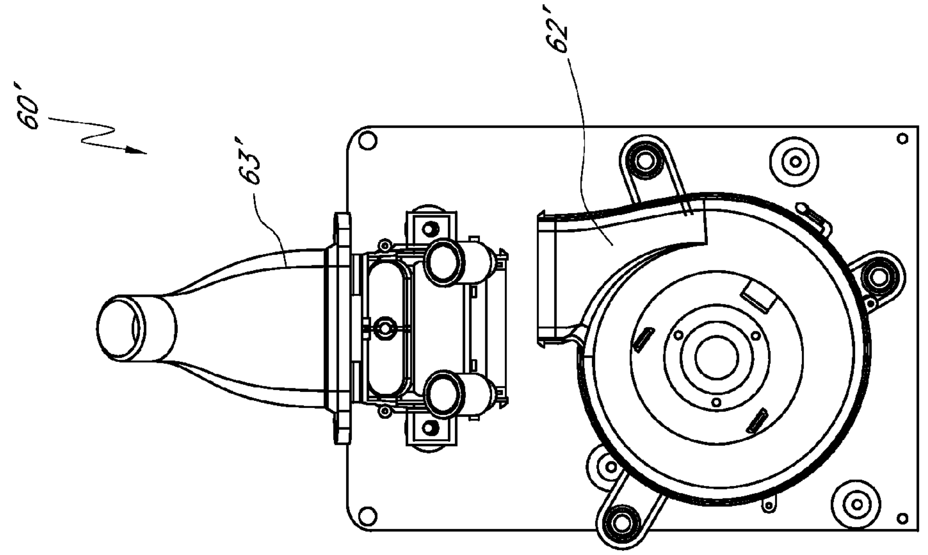
FIG. 23B illustrates a front view of the interior of the box of FIGS. 22 and 23A.
Figure 23A:
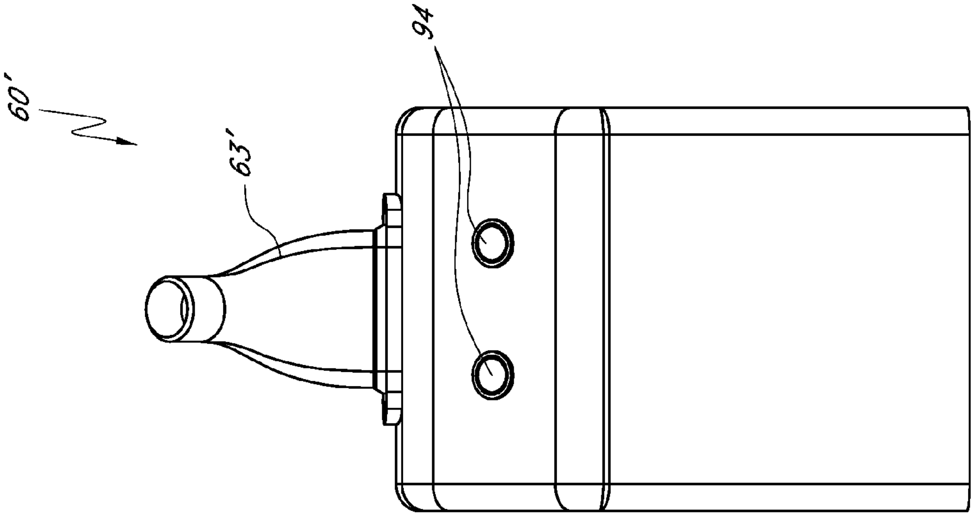
FIG. 23A illustrates a front view of the fluid box of FIG. 22.

Another embodiment of a fluid box 60' is illustrated in FIGS. 22, 23A and 23B. The depicted fluid box 60' is generally smaller than the box 60 of FIGS. 19A and 19B. As illustrated in FIG. 23B, the fluid box 60' includes only a single fluid module 62'. Thus, such a smaller fluid box 60' can be utilized when the fluid demand for a conditioner mat or topper member is relatively small. The fluid box 60' can include one or more buttons 94 or other controllers that help regulate the operation of the fluid module(s) positioned therein. For example, in one embodiment, the box 60' includes a red button or other controller, which the user presses or otherwise manipulates to direct relatively warm air to the topper member, and a blue button or other controller, which the user presses or otherwise manipulates to direct relatively cool air to the topper member. A fluid box (or a separate controller or control panel) can include additional buttons, knobs, dials, keypads, touchscreens and/or other controllers, as desired.

With continued reference to FIG. 22, a channel 96 or other hooking device located along the rear surface of the fluid box 60' can help mount the box 60' to a headboard, footboard, a side rail, a side panel, a frame or other support structure and/or any other portion of a bed (e.g., hospital or medical bed, conventional bed, other type of bed, other seating assembly, etc.) and/or any other surface or location (e.g., wall, floor, an adjacent medical device, other hospital equipment, etc.).

Figure 24:
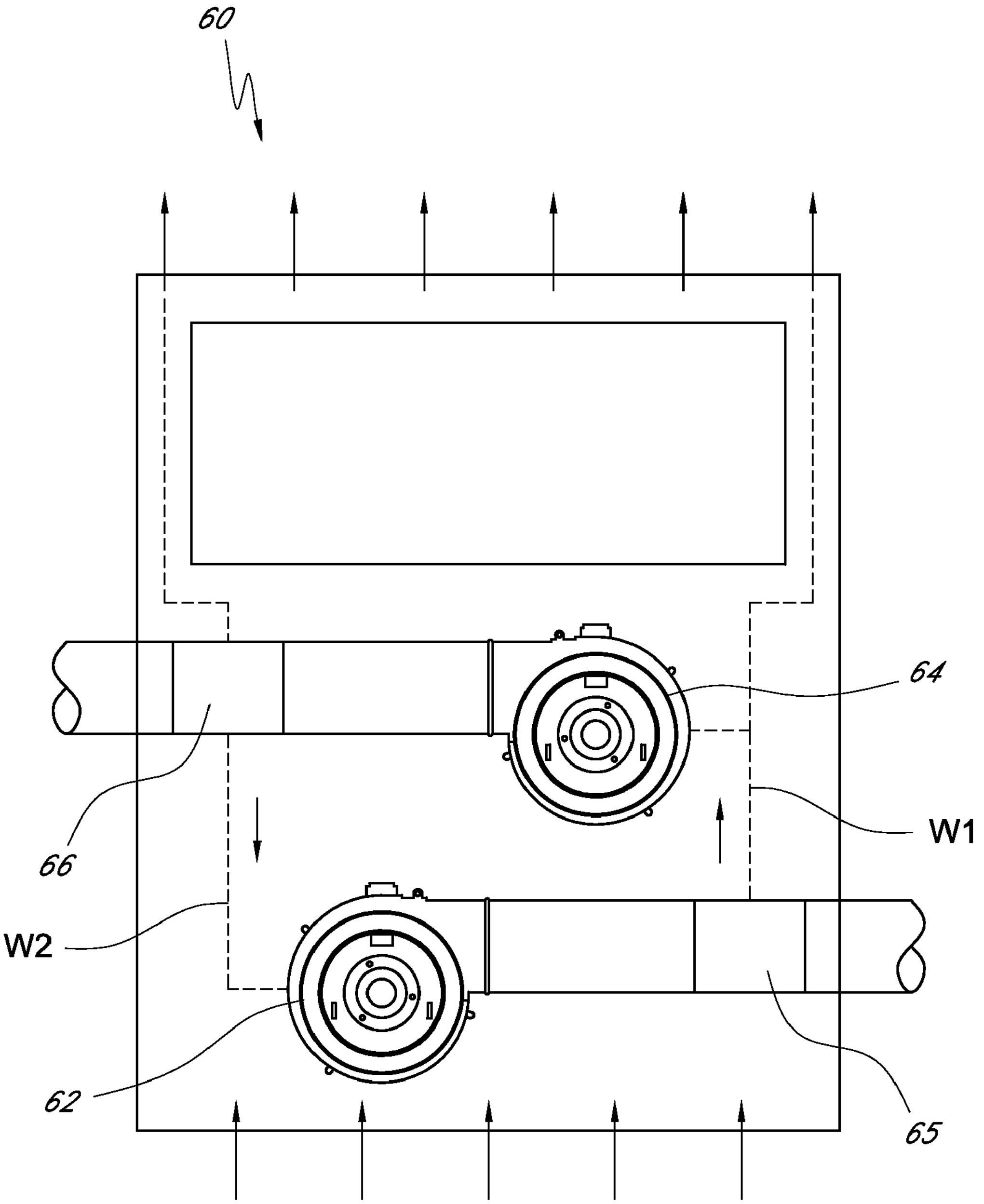
FIG. 24 schematically illustrates fluid diagram within a fluid box comprising two fluid modules, in accordance with one embodiment.
Figure 25:
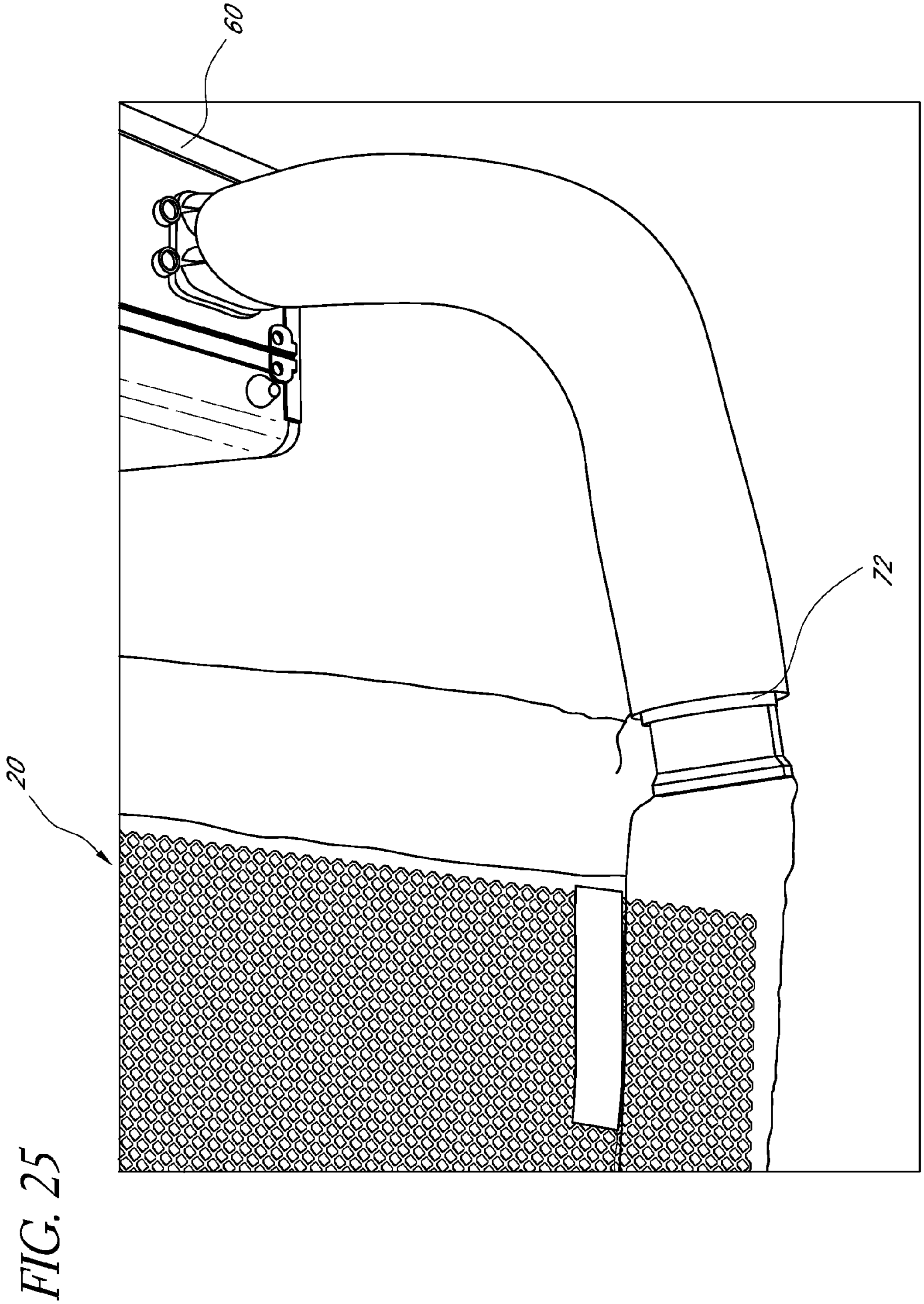
FIG. 25 illustrates a plan view of an insulated conduit in fluid communication with a conditioner mat or topper member according to one embodiment.

In certain embodiments where fluid modules 62, 64 located within a single fluid box 60 are configured to both heat and cool a fluid being delivered to a conditioner mat, the waste streams of the respective thermoelectric devices 65, 66 can be used to help improve the overall thermal-conditioning efficiency of the system. For example, assuming that the first fluid module 62 schematically illustrated in FIG. 24 is operating in a cooling mode, the waste fluid W1 exiting the first thermoelectric device 65 will be warm relative to ambient air. Thus, at least a portion of this relatively “warm” fluid stream can be directed into the inlet of the second fluid module 64, which is operating in a heating mode. Thus, it will be generally easier and more cost effective to heat the air exiting the second fluid module 64 under such a scheme (e.g., because the starting temperature of the fluid to be heated is generally higher than ambient air). Likewise, the efficiency of the first fluid module 62 can be improved if a portion of the relatively cool waste fluid W2 exiting the second thermoelectric device 66 is directed to the inlet of the first fluid module 62.

As noted above and illustrated in FIG. 25, a conduit 72 that delivers thermally-conditioned fluid from the fluid modules (e.g., located within a fluid box) to a conditioner mat or topper member 20 can be partially or completed covered with one or more layers of thermal insulation 73. Such a configuration, which may be incorporated into any of the embodiments disclosed herein or equivalents thereof, can help reduce or prevent undesirable heat transfer (e.g., either to or from the fluid being delivered to the mat). As a result, the temperature of the fluids being delivered to the fluid zones of a mat or topper member can be more accurately maintained within the desired range.

Figure 26:
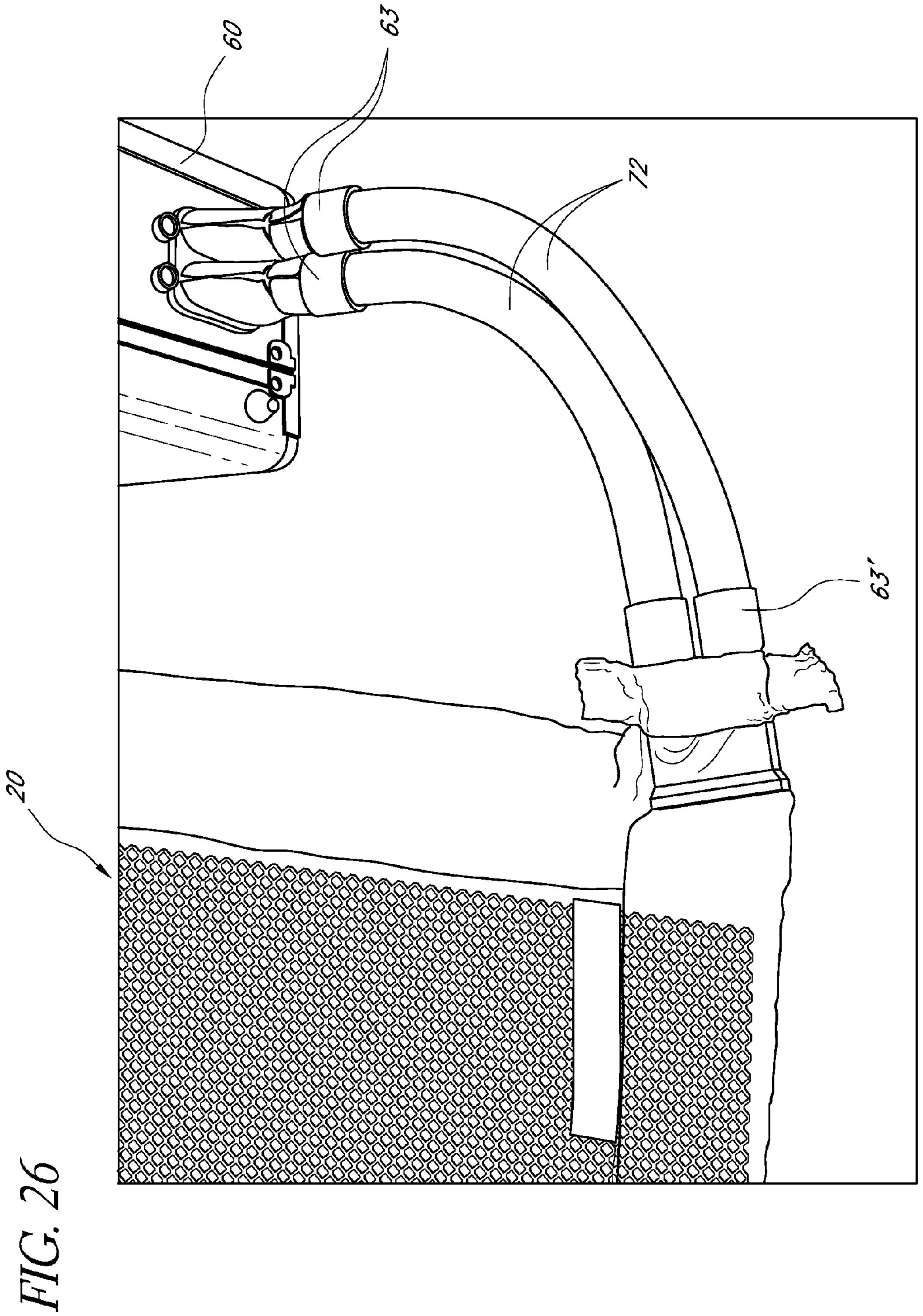
FIG. 26 illustrates a plan view of a conduit system in fluid communication with a conditioner mat or topper member according to another embodiment.
Figure 27:
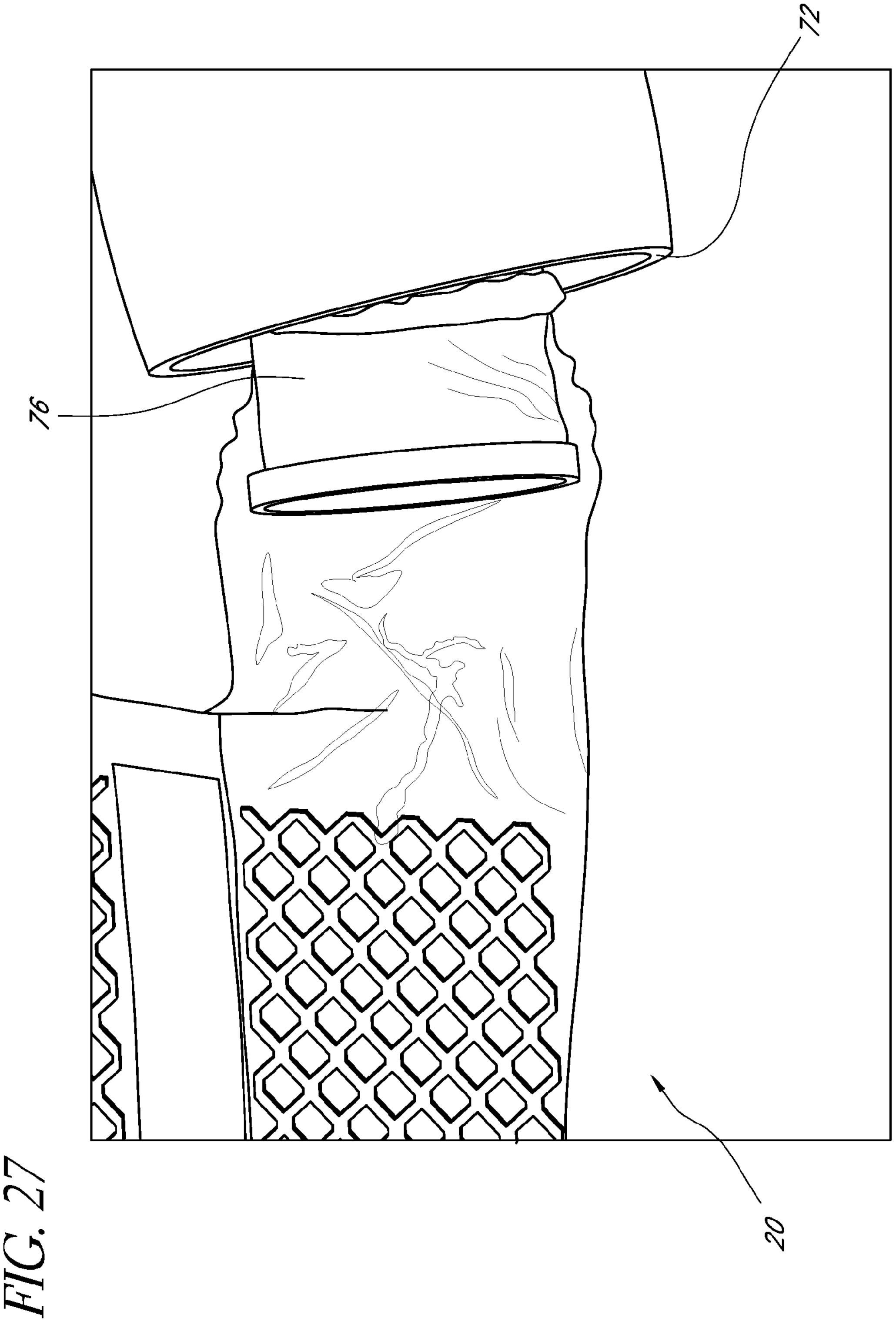
FIG. 27 illustrates a plan view of the interface of a fluid inlet and a conditioner mat or topper member according to one embodiment.

In certain arrangements, two or more outlet fittings 63 can be used to deliver ambient and/or conditioned fluid from one or more fluid modules to an inlet of a conditioner mat 20. With reference to FIG. 26, such a dual conduit design can help reduce fluid headlosses through the system, thereby lowering the backpressure experienced by the blowers and other components of the fluid modules. With reference to FIG. 27, a fitting 76 can be used at the inlets of a conditioner mat or topper member 20. Such a fitting 76 can help prevent or reduce the likelihood of leaks as air or other fluid is transferred from the upstream conduit 72 to the mat 20. In addition, such a fitting 76 can make it easier for a user to connect (or disconnect) a mat from the upstream fluid delivery system (e.g., conduit 72). Such features can be incorporated into any of the mat or topper member embodiments disclosed herein, or equivalents thereof.

Figure 28A:
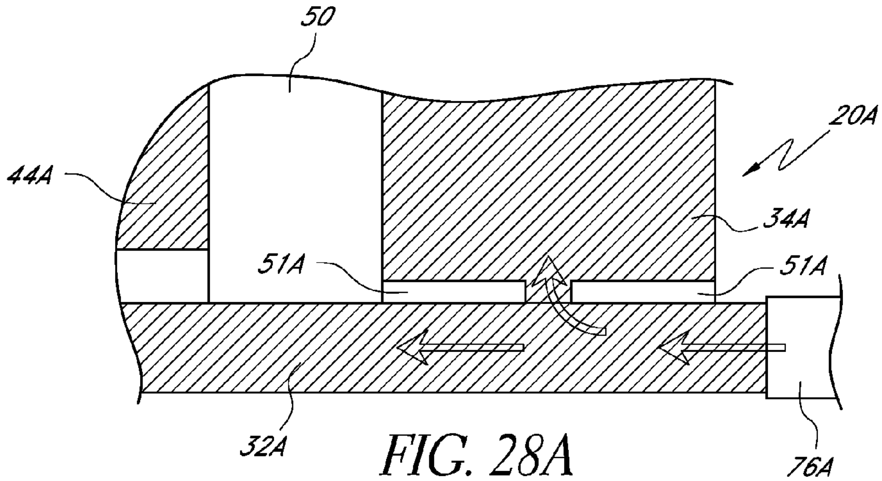
FIGS. 28A-28C illustrates flow diagrams representing various methods of balancing airflow into the various fluid zones of a conditioner mat or topper member, in accordance with one embodiment.
Figure 28B:
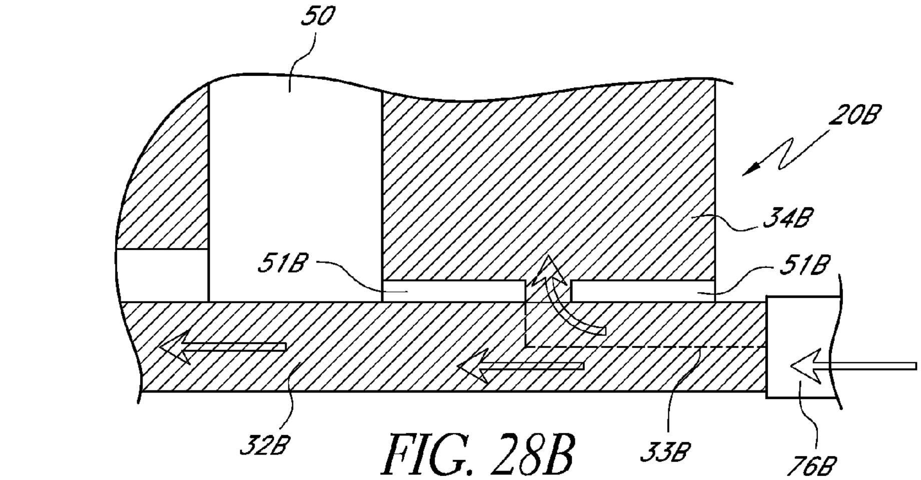
Figure 28C:
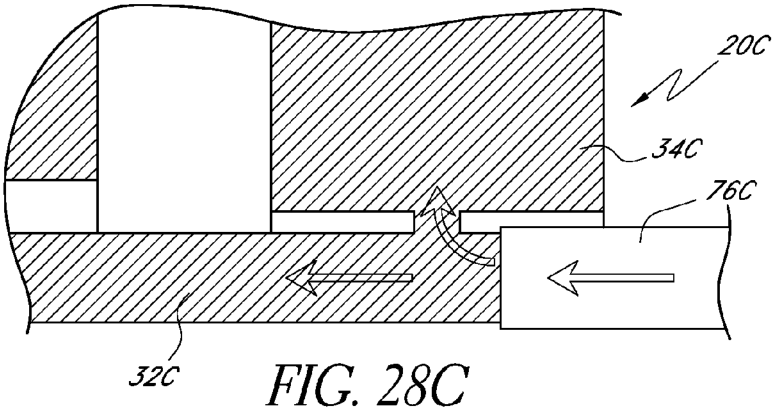

FIGS. 28A-28C illustrate different embodiments of ensuring that the desired volume or flowrate of fluid is delivered to each fluid zone of a conditioner mat or topper member. For example, in the arrangement depicted in FIG. 28A, the upstream fluid zone 34A (e.g., the fluid zone closest to the inlet fitting 76A) comprises a gate 51A at or near the interface of the fluid zone 34A and the main passage 32A. According to some embodiments, the gate 51A comprises one or more foam pieces or any other flow blocking or diversion members that can regulate the rate of fluid flowrate from the passage 32A to the upstream fluid zone 34A. The gate can include one or more other materials other than foam, such as, for example, other polymeric or elastomeric materials, paper or wood-based materials, metals, alloys, composites, textiles, fabrics, other natural or synthetic materials and/or the like. In other embodiments, the gates are created by strategically attaching the upper and lower portions (e.g., using stitching, adhesives, hot melting, crimping, other fasteners, any other connection method or device) to each other, either in lieu of or in addition to including flow blocking or diverting members (e.g., foam or other materials, etc.). Thus, regardless of how the gates are configured, as flow into the upstream fluid zone 34A becomes restricted, more fluid will be delivered to downstream fluid zones (zone 36, see, e.g., FIGS. 1, 2, 4 and 5).

In FIG. 28B, the main passage 32B includes one or more fluid boundaries 33B that help ensure that a particular portion of the fluid entering the conditioner mat 20B enters the upstream fluid zone 34B. As discussed in greater detail herein, such fluid boundaries or nodes can be created using various devices or methods, such as, for example, hot melting, gluing or otherwise joining the upper and lower sheets of the mat together. Alternatively, in order to ensure more accurate flow balancing between the various fluid zones, separate passages (e.g., in the form of conduits) can be used to feed individual fluid zones.

Another embodiment of improving or enhancing flow balancing into the various fluid zones is illustrated in FIG. 28C. As shown, the inlet fitting 76C can be positioned further into the passage 32C or conduit of the conditioner mat 20C or topper member. Such a feature can help direct additional fluid past the upstream fluid zone 34C and into downstream fluid zones, as fluid is less likely, hydraulically, to enter into the most upstream zone 34C. One or more additional ways of balancing fluid flow into the various fluid zones can also be used, either in lieu of or in addition to those specifically disclosed herein. For example, the quantity, size, shape, density, spacing and other details of the outlet openings located within each fluid zone can affect how well fluid flows are balanced. In some embodiments, the size (e.g., width, length, height, cross-sectional area, etc.), location and other details of the gates or other inlets into each of the gates can be adjustable, allowing a user to modify flow distribution according to a desired or required scheme. For example, in one embodiment, the length of a blocking member that helps define a gate 51A, 51B can be shortened or lengthened (e.g., using a telescoping design, by removing or adding portions, etc.).

Figure 29A:
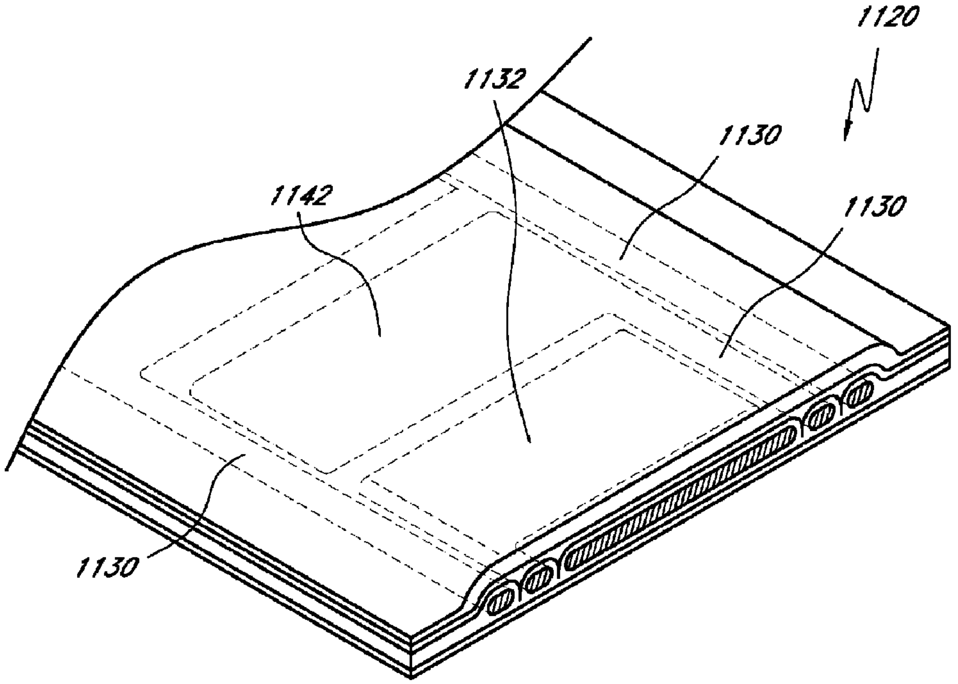
FIGS. 29A and 29B illustrate different perspective views of a conditioner mat or topper member according to another embodiment.
Figure 29B:
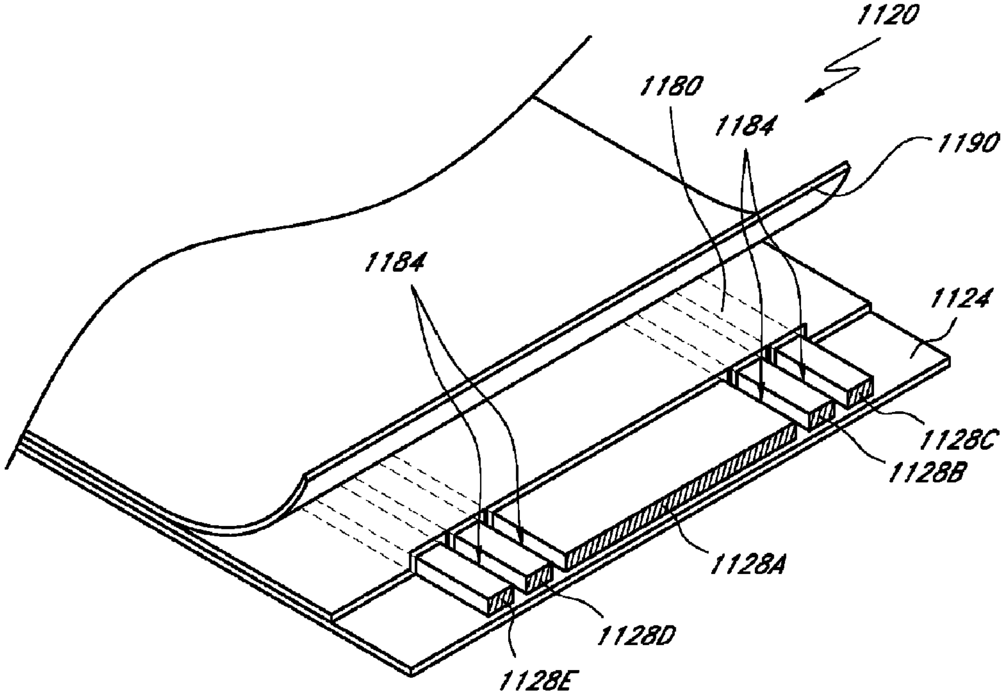

FIGS. 29A and 29B illustrate another embodiment of a conditioner mat or topper member 1120 that is configured to be positioned, at least partially, along an upper portion of a medical bed, other type of bed or other seating assembly. As with other embodiments disclosed herein, the depicted conditioner mat 1120 comprises one or more fluid zones 1132, 1142 that are configured to selectively receive thermally or environmentally conditioned and/or unconditioned fluid (e.g., ambient, heated and/or cooled air from one or more fluid modules).

As illustrated in the partial perspective view of FIG. 29B, the conditioner mat 1120 can include one or more spacer material portions 1128A-1128E positioned between a generally fluid impermeable bottom layer 1124 (e.g., vinyl sheet or layer, tight-woven fabric, lining, etc.) and an upper scrim layer 1180. For clarity, at least some of the layers and other components of the mat 1120 are shown separated from each other in FIG. 29B. The generally fluid impermeable bottom layer 1124 and an upper scrim layer 1180 can be selectively and strategically attached to each other to form continuous or intermittent fluid barriers 1184 or borders that prevent or reduce the likelihood of fluid flow thereacross. Consequently, fluid zones, non-fluid zones, chambers, passages and other features can be advantageously provided within a conditioner mat 1120. According to certain arrangements, the barriers 1184 can be formed using stitching, fusion, adhesives, heat staking, other bonding agents or techniques and/or any other attachment method or device. Such fluid barriers 1184 can help direct fluid into targeted fluid zones, through specific passages or openings and/or as otherwise desired or required. For example, in the arrangement illustrated in FIGS. 29A and 29B, fluid barriers 1184 are used to create a plurality of passages 1128B-1128E located along the sides of the mat 1120.

With continued reference to FIGS. 29A and 29B, as with any other embodiments disclosed herein, the conditioner mat 1120 can additionally include a comfort layer 1190 and/or any other layer generally above (and/or or below) the scrim layer 1180. Such an air permeable comfort layer 1190 (e.g., quilt layer, soft air permeable or perforated foam, etc.) can further enhance the comfort level of an occupant positioned along the top of the conditioner mat 1120. In some arrangements, the scrim layer 1180, and/or any other layers or components positioned between the upper comfort layer 1190 and the spacer material 1128A-1128E (e.g., spacer fabric, air permeable structure, woven polyester or other material, etc.) or other fluid distribution member, are configured to help distribute the air or other fluid being delivered to the mat or topper member 1120. The use of heat staking, stitching, fusion, other types of bonding and/or any other attachment method or device can be incorporated into any embodiments of a conditioner mat or topper member disclosed herein or equivalents thereof, including those illustrated in FIGS. 1-33.

Figure 30:
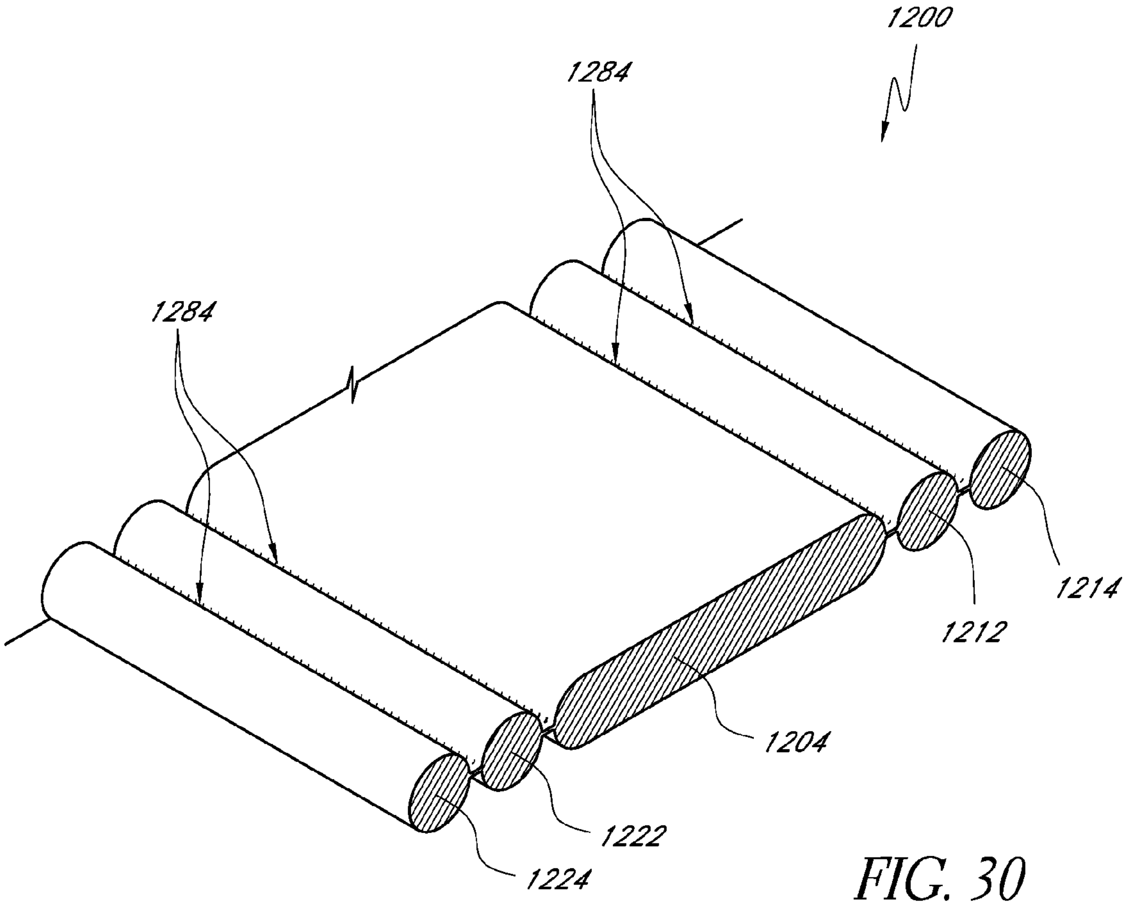
FIG. 30 illustrates a perspective view of a spacer material or other fluid distribution member configured for use within a conditioner mat or topper member according to one embodiment.

A partial perspective view of one embodiment of a spacer material 1200 configured for use in a conditioner mat or topper member is illustrated in FIG. 30. As shown, the spacer material 1200 can comprise one or more fluid permeable materials and/or structures. For example, the spacer material can include a spacer fabric, a porous foam, a honeycomb or other porous structure, other materials or members that are generally air permeable or that have an open structure through which fluids may pass and/or the like. As with the arrangement of FIGS. 29A and 29B, the spacer material or member 1200 depicted in FIG. 30 can include one or more fluid barriers 1284 that are continuously or intermittently positioned so as to create separate fluid passageways 1212, 1214, 1222, 1224, fluid zones 1204, non-fluid zones and/or other fluid boundaries, as desired or required. The barriers 1284 can be formed using stitching, heat staking, adhesives, crimping, clips, other fasteners, bonding or other fusion techniques and/or the like. In some embodiments, as illustrated in FIG. 30, a mat comprises a spacer 1200 that includes generally tubular spacer members 1212, 1214, 1222, 1224 and/or generally flat spacer members 1204. The tubular spacer members, which in some arrangements serve as main conduits, can be positioned along the sides of the mat (as illustrated in FIG. 30) and/or any other mat portion (e.g., middle, away from the sides, etc.), as desired or required.

Figure 31:
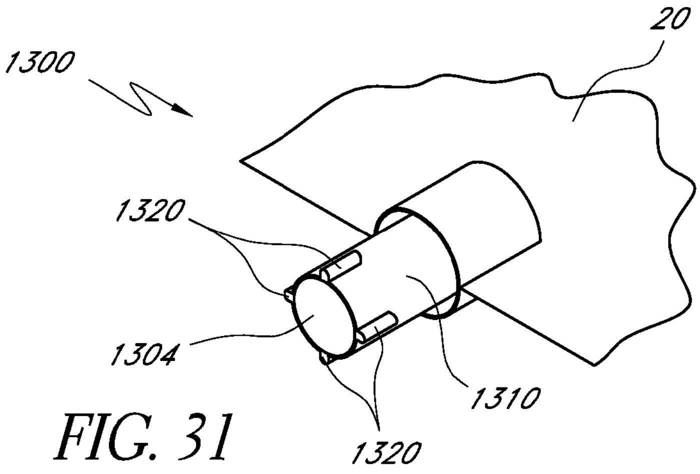
FIG. 31 illustrates a perspective view of a fluid nozzle or other inlet of a conditioner mat or topper member according to one embodiment.

One embodiment of a fluid nozzle or other inlet 1300 configured to be used on a conditioner mat is illustrated in FIG. 31. As shown, the nozzle 1300 can extend along an edge (e.g., side) of a conditioner mat or topper member 20 so as to facilitate connection to (or disconnection from) a conduit (not shown) that places the mat 20 in fluid communication with one or more fluid modules. The nozzle 1300 can include a main portion 1310, which in some embodiments, includes a generally cylindrical shape defining an interior space 1304. Along it exterior surface, the main portion 1310 can comprise one or more alignment and/or quick-connect features 1320 (e.g., tabs, other protrusions, slots, other recesses, etc.) that are shaped, sized and otherwise configured to generally mate with corresponding mating or engaging features on the conduit (not shown) to which the fluid nozzle 1300 can be selectively connected or disconnected.

Figure 32:
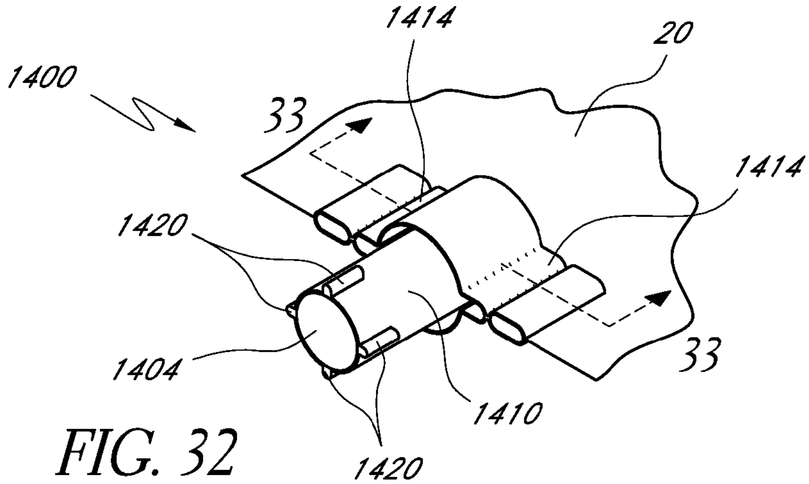
FIG. 32 illustrates a perspective view of a fluid nozzle or other inlet of a conditioner mat or topper member according to another embodiment.
Figure 33:
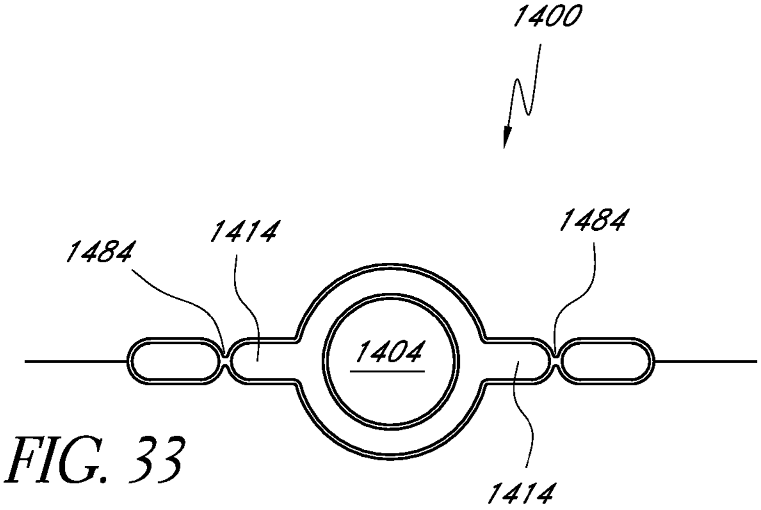
FIG. 33 illustrates a cross-sectional view of the fluid nozzle of FIG. 32.

Other embodiments of a fluid nozzle 1400 for a conditioner mat or topper member 20 are illustrated in FIGS. 32 and 33. As with the nozzle of FIG. 31, the depicted arrangements comprise a main portion 1410 which generally extends from an edge of the mat 20 and which comprises one or more alignment and/or quick-connect features 1420. In addition, as illustrated in the cross-sectional view of FIG. 33, the layers and/or other components of the conditioner mat 20 that define an interior space through which air is selectively delivered can be configured to properly locate and secure the nozzle 1400 thereon. For example, fluid boundaries or barriers 1484 (e.g., stitching, heat staking, bonding, etc.) can be used to form the opening through which the nozzle 1400 can extend.

As discussed herein, control of the fluid modules and/or any other components of a conditioner mat or topper member can be based, at least partially, on feedback received from one or more sensors. For example, a mat or topper member can include one or more thermal sensors, humidity sensors, condensation sensors, optical sensors, motion sensors, audible sensors, occupant detection sensors, other pressure sensors and/or the like. In some embodiments, such sensors can be positioned on or near a surface of the mat or topper member to determine whether cooling and/or heating of the assembly is required or desired. For instance, thermal sensors can help determine if the temperature at a surface of the mat is above or below a desired level. Alternatively, one or more thermal sensors and/or humidity sensors can be positioned in or near a fluid module, a fluid conduit (e.g., fluid passageway) and/or a layer of the upper portion of the topper member (e.g., fluid distribution member, comfort layer, etc.) to detect the temperature and/or humidity of the discharged fluid. Likewise, pressure sensors can be configured to detect when a user has been in contact with a surface of the bed for a prolonged time period. Depending on their type, sensors can contact a portion of the mat or the adjacent portion of the bed assembly on which the mat has been situated. As discussed herein, in some embodiments, sensors are located within and/or on the surface of the mat or topper member. However, in other arrangements, the sensors are configured so they do not contact any portion of the mat at all. Such operational schemes can help detect conditions that are likely to result in pressure ulcers. In addition, such schemes can help conserve power, enhance comfort and provide other advantages. For additional details regarding the use of sensors, timers, control schemes and the like for climate controlled assemblies, refer to U.S. patent application Ser. No. 12/208,254, filed Sep. 10, 2008, titled OPERATIONAL CONTROL SCHEMES FOR VENTILATED SEAT OR BED ASSEMBLIES and published on Mar. 12, 2009 as U.S. Publication No. 2009/0064411, and U.S. patent application Ser. No. 12/505,355, filed Jul. 17, 2009, titled CLIMATE CONTROLLED BED ASSEMBLY and published on Jan. 21, 2010 as U.S. Publication No. 2010/0011502, the entireties of both of which are hereby incorporated by reference herein.

To assist in the description of the disclosed embodiments, words such as upward, upper, downward, lower, vertical, horizontal, upstream, downstream, top, bottom, soft, rigid, simple, complex and others have and used above to discuss various embodiments and to describe the accompanying figures. It will be appreciated, however, that the illustrated embodiments, or equivalents thereof, can be located and oriented in a variety of desired positions, and thus, should not be limited by the use of such relative terms.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while the number of variations of the inventions have been shown and described in detail, other modifications, which are within the scope of these inventions, will be readily apparent to those of skill in the art based upon this disclosure. It is also contemplated that various combinations or subcombinations of the specific features and aspects of the embodiments may be made and still fall within the scope of the inventions. Accordingly, it should be understood that various features and aspects of the disclosed embodiments can be combined with, or substituted for, one another in order to perform varying modes of the disclosed inventions. Thus, it is intended that the scope of the present inventions herein disclosed should not be limited by the particular disclosed embodiments described above, but should be determined only by a fair reading of the claims.

What is claimed is:

1. A conditioner mat for use with a bed assembly, comprising:

an upper layer having a plurality of openings;

a lower layer being substantially fluid impermeable;

wherein the upper layer is attached to the lower layer along a periphery of the conditioner mat;

an interior chamber defined between the upper layer and the lower layer;

a spacer material positioned within the interior chamber, said spacer material configured to maintain a shape of the interior chamber and configured to help with the passage of fluids within at least a portion of the interior chamber;

at least one inlet in fluid communication with the interior chamber;

at least one fluid module comprising a fluid transfer device;

a conduit connecting an outlet of the at least one fluid module with the at least one inlet;

at least one fluid impermeable member positioned within the interior chamber, said at least one fluid impermeable member forming at least one non-fluid zone; and a control module for regulating at least one operational parameter of the at least one fluid module;

a user input device configured to receive at least one climate control setting of the bed assembly; and at least one power supply adapted to selectively provide electrical power to the at least one fluid module;

wherein the at least one fluid module selectively delivers fluids to the interior chamber through the conduit and the at least one inlet;

wherein fluids entering the interior chamber through the at least one inlet are generally distributed by the spacer material within at least a portion of the interior chamber before exiting through the plurality of openings along the upper layer;

wherein fluids entering the interior chamber are generally not permitted to flow through the at least one non-fluid zone;

wherein a thickness of the conditioner mat along the at least one non-fluid zone is generally equal to a thickness of the conditioner mat along a portion of the conditioner mat that comprises a spacer material; and wherein the conditioner mat is configured to be removably placed on top of a bed assembly to selectively deliver fluids to an occupant positioned thereon.

2. The conditioner mat of claim 1, wherein the upper layer and the lower layer comprise a unitary structure.

3. The conditioner mat of claim 1, wherein the upper layer and the lower layer comprise separate members.

4. The conditioner mat of claim 1, wherein the at least one fluid impermeable member comprises foam.

5. The conditioner mat of claim 1, wherein the at least one non-fluid zone generally separates at least two areas of the conditioner mat that comprise spacer material.

6. The conditioner mat of claim 1, wherein the at least one fluid module is configured to thermally condition fluid being transferred from the fluid transfer device to the interior chamber of the conditioner mat.

7. The conditioner mat of claim 1, wherein the at least one fluid module comprises a thermoelectric device configured to selectively heat or cool fluid being transferred to the interior chamber of the conditioner mat.

8. The conditioner mat of claim 1, further comprising at least one securement device for securing the conditioner mat to a bed assembly.

9. The conditioner mat of claim 1, further comprising at least one moisture sensor configured to detect a presence of liquid or other moisture on or within the conditioner mat.

10. The conditioner mat of claim 1, further comprising at least one fluid distribution member positioned on top of the upper layer, said at least one fluid distribution member being configured to help distribute fluid flow exiting the plurality of openings of the upper layer.

11. A topper member for use with a medical bed, comprising:

an enclosure defining at least one interior chamber and having substantially fluid impermeable upper and lower layers; said upper layer comprising a plurality of openings through which fluid from the at least one interior chamber can exit;

at least one fluid passage formed within the enclosure by selectively attaching the upper layer to the lower layer along at least a portion of the enclosure;

at least two fluid zones formed within the enclosure, at least one of said at least two fluid zones being in fluid communication with the at least one fluid passage;

at least one non-fluid zone within the enclosure, said at least one non-fluid zone comprising at least one fluid impermeable member, wherein said at least one fluid impermeable member is configured to generally prevent fluid flow through the at least one non-fluid zone;

a spacer material positioned within the enclosure of each of the at least two fluid zones, said spacer material configured to maintain a desired separation between the upper and lower layers and to help distribute fluid within the at least one interior chamber;

at least one fluid module comprising a fluid transfer device;

a conduit placing an outlet of the at least one fluid module in fluid communication with the at least one fluid passage;

wherein the at least one fluid module selectively delivers fluid to at least one of the at least two fluid zones through the conduit and the passage;

wherein fluids entering the at least two fluid zones are generally distributed within the at least one interior chamber by the spacer material before exiting through the plurality of openings along the upper layer;

wherein the at least one non-fluid zone is positioned generally between the at least two fluid zones; and wherein a thickness of the topper member along the at least one non-fluid zone is generally equal to a thickness of the topper member along portions of the topper member that comprise a spacer material.

12. The topper member of claim 11, wherein the at least two fluid zones comprises a first fluid zone and a second fluid zone, said first and second fluid zones being configured to receive fluid from the same at least one fluid module.

13. The topper member of claim 11, wherein the at least two fluid zones comprises a first fluid zone and a second fluid zone, said first fluid zone being configured to selectively receive fluid from a first fluid module and said second fluid zone being configured to selectively receive fluid from a second fluid module.

14. The topper member of claim 11, wherein the upper and lower layers comprise a unitary structure.

15. The topper member of claim 11, wherein the upper and lower layers are separate members that are attached to each other.

16. The topper member of claim 11, wherein the at least one fluid impermeable member comprises foam.

17. The topper member of claim 11, wherein the at least one fluid module comprises a thermoelectric device configured to selectively heat or cool fluid being delivered to the topper member.

18. The topper member of claim 11, further comprising at least one moisture sensor configured to detect a presence of moisture on, within or near the topper member.

19. The topper member of claim 11, further comprising at least one fluid distribution member positioned on top of the upper layer, said at least one fluid distribution member being configured to help distribute fluid flow exiting the plurality of openings of the upper layer.

20. The topper member of claim 13, wherein the first fluid zone is configured to receive fluid having a first temperature, and wherein the second fluid zone is configured to receive fluid having a second temperature, wherein the first temperature is greater than the second temperature.

* * * * *